US009580506B2

(12) United States Patent
Gerarda Havenith et al.

(10) Patent No.: US 9,580,506 B2
(45) Date of Patent: Feb. 28, 2017

(54) POTENCY ASSAYS FOR ANTIBODY DRUG SUBSTANCE BINDING TO AN FC RECEPTOR

(75) Inventors: Catharina Emanuele Gerarda Havenith, Bodegraven (NL); Tom Vink, Alphen aan den Rijn (NL); Patrick Van Berkel, Utrecht (NL); Paul Parren, Odijk (NL)

(73) Assignee: GENMAB A/S, Copenhagen (DK)

( * ) Notice: Subject to any disclaimer, the term of this patent is extended or adjusted under 35 U.S.C. 154(b) by 1135 days.

(21) Appl. No.: 11/989,064

(22) PCT Filed: Jul. 21, 2006

(86) PCT No.: PCT/DK2006/000426
§ 371 (c)(1),
(2), (4) Date: Sep. 25, 2009

(87) PCT Pub. No.: WO2007/009469
PCT Pub. Date: Jan. 25, 2007

(65) Prior Publication Data
US 2010/0015644 A1    Jan. 21, 2010

Related U.S. Application Data

(60) Provisional application No. 60/701,656, filed on Jul. 21, 2005, provisional application No. 60/752,923, filed on Dec. 21, 2005.

(51) Int. Cl.
*G01N 33/53* (2006.01)
*C07K 16/28* (2006.01)
*G01N 33/566* (2006.01)
*C07K 16/00* (2006.01)

(52) U.S. Cl.
CPC ...... *C07K 16/2812* (2013.01); *C07K 16/2863* (2013.01); *G01N 33/566* (2013.01); *C07K 2317/21* (2013.01); *C07K 2317/34* (2013.01); *C07K 2317/41* (2013.01); *C07K 2317/732* (2013.01); *C07K 2317/76* (2013.01); *G01N 2333/70535* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,495,285 A | 1/1985 | Shimizu et al. |
| 4,609,546 A | 9/1986 | Hiratani |
| 4,766,106 A | 8/1988 | Katre et al. |
| 4,894,442 A | 1/1990 | Toyama et al. |
| 5,624,821 A | 4/1997 | Winter et al. |
| 5,648,260 A | 7/1997 | Winter et al. |
| 6,121,022 A | 9/2000 | Presta et al. |
| 6,737,056 B1 | 5/2004 | Presta |
| 7,084,260 B1* | 8/2006 | Lonberg et al. ........ 530/388.75 |
| 2003/0157108 A1* | 8/2003 | Presta ........................ 424/145.1 |
| 2004/0110226 A1* | 6/2004 | Lazar et al. .................. 435/7.1 |
| 2010/0015644 A1* | 1/2010 | Gerarda Havenith et al. ........................ 435/7.92 |

FOREIGN PATENT DOCUMENTS

| | | |
|---|---|---|
| EP | 0125023 A1 | 11/1984 |
| EP | 0171496 A2 | 2/1986 |
| EP | 0173494 A2 | 3/1986 |
| EP | 0184187 A2 | 6/1986 |
| WO | WO-86/01533 A1 | 3/1986 |
| WO | WO-87/02671 A1 | 5/1987 |
| WO | WO-89/11490 A1 | 11/1989 |
| WO | WO-94/11026 A2 | 5/1994 |
| WO | WO-94/29351 A2 | 12/1994 |
| WO | WO-96/40210 A1 | 12/1996 |
| WO | WO-97/13852 A1 | 4/1997 |
| WO | WO-99/54342 A1 | 10/1999 |
| WO | WO 00/42072 * | 7/2000 |
| WO | WO-00/42072 A2 | 7/2000 |
| WO | WO-02/100348 A2 | 12/2002 |
| WO | WO-03/011878 A2 | 2/2003 |
| WO | WO-03/085119 A1 | 10/2003 |
| WO | WO-2004/029207 A2 | 4/2004 |

(Continued)

OTHER PUBLICATIONS

Statement on a Nonproprietary Name Adopted by the USAN Council. May 23, 2012, p. 1.*
Ferrara et al. JBC 2006, 281;8:5032-5036.*
FDA: Points to Consider in the Manufacture and Testing of Monoclonal Antibody Products for Human Use, Feb. 28, 1997. pp. 1-50.*
Shapiro. Regulatory Perspectives and Expectation of Fc effector Function Assessment, 2010 pp. 1-31.*
Takahashi et al. Glycobiology 2002, 12;8:507-515.*
Galon et al. Eur. J. Immunol. 1997, 27:1928-1932.*

(Continued)

*Primary Examiner* — Chun Dahle
(74) *Attorney, Agent, or Firm* — Nelson Mullins Riley & Scarborough LLP; Jane E. Remillard, Esq.; Christopher L. Frank

(57) ABSTRACT

The invention relates to a method of characterizing an antibody, which method is suitable as a potency assay for batch release of a pharmaceutical composition comprising an antibody, specifically for use when applying for marketing authorization for said pharmaceutical composition. The assay provided is a method for determining the potency of a drug product comprising an FcR binding peptide, wherein at least one mechanism of action of the FcR binding peptide of the drug product is mediated through the binding of the FcR binding peptide of the drug product to a Fc receptor, wherein said method comprises determining the binding of the FcR binding peptide of the drug product to an Fc receptor.

104 Claims, 26 Drawing Sheets

(56) References Cited

FOREIGN PATENT DOCUMENTS

| WO | WO-2004/035607 A2 | 4/2004 |
|----|-------------------|--------|
| WO | WO-2004/056847 A2 | 7/2004 |
| WO | WO-2004/063351 A2 | 7/2004 |
| WO | WO-2004/065540 A2 | 8/2004 |
| WO | WO-2004/099249 A2 | 11/2004 |
| WO | WO-2005/018669 A1 | 3/2005 |
| WO | WO-2005/044859 A2 | 5/2005 |
| WO | WO-2005/063815 A2 | 7/2005 |

OTHER PUBLICATIONS

Bleeker, Wim K. et al., "Dual Mode of Action of a Human Anti-Epidermal Growth Factor Receptor Monoclonal Antibody for Cancer Therapy," *The Journal of Immunology*, vol. 173:4699-4707 (2004).

Cabilly, Shmuel et al., "Generation of antibody activity from immunoglobulin polypeptide chains produced in *Escherichia coli*," *Proc. Natl. Acad. Sci. USA*, vol. 81:3273-3277 (1984).

Cooper, Helen M. et al., "Determination of Specific Antibody Titer and Isotype," *Current Protocols in Molecular Biology*, pp. 11.17.1-11.17-13 (2000).

Debets, Joop M.H. et al., "Cross-linking of Both FcγRI and FcγRII Induces Secretion of Tumor Necrosis Factor by Human Monocytes, Requiring High Affinity Fc-FcγR Interactions," *The Journal of Immunology*, vol. 144(4):1304-1310 (1990).

Glennie, Martin J. et al., "Renaissance of cancer therapeutic antibodies," *DDT*, vol. 8(11):503-510 (2003).

Koene, Harry R. et al., "FcγRIIIa-158V/F Polymorphism Influences the Binding of IgG by Natural Killer Cell FcγRIIIa, Independently of the FcγRIIIa-48L/R/H Phenotype," *Blood*, vol. 90(3):1109-1114 (1997).

Maloney, David G., "Concepts of Radiotherapy and Immunotherapy: Anti-CD20 Mechanisms of Action and Targets," *Seminars in Oncology*, vol. 32(Suppl. 1):S19-S26 (2005).

Margulies, D.H., "Enzyme-Linked Immunosorbent Assays," *Current Protocols in Immunology*, pp. 2.1.2-2.1.22 (1991).

Miraglia, Sheri et al., "Homogeneous Cell- and Bead-Based Assays for High Throughput Screening Using Fluorometric Microvolume Assay Technology," *Journal of Biomolecular Screening*, vol. 4(4):193-204 (1999).

Murano, G., "FDA Perspective on Specifications for Biotechnology Products from IND to PLA," *Development for Specifications for Biotechnology Pharmaceutical Products*, vol. 91:3-13 (1997).

Niwa, Rinpei et al., "Enhancement of the Antibody-Dependent Cellular Cytotoxicity of Low-Fucose IgG1 Is Independent of FcγRIIIa Functional Polymorphism," *Clinical Cancer Research*, vol. 10:6248-6255 (2004).

Presta, Leonard G., "Antibody engineering," *Current Biology in Structural Biology*, vol. 2:593-596 (1992).

Shields, Robert L. et al., "High Resolution Mapping of the Binding Site on Human IgG1 for FcγRII, FcγRIII, and FcRn and Design of IgG1 Variants with Improved Binding to the FcγR," *The Journal of Biological Chemistry*, vol. 276(9):6591-6604 (2001).

Shields, Robert L. et al., "Lack of Fucose on Human IgG1 N-Linked Oligosaccharide Improves Binding to Human FcDRIII and Antibody-dependent Cellular Toxicity," *The Journal of Biological Chemistry*, vol. 277(30):26733-26740 (2002).

van Sorge, N.M. et al., "FcγR polymorphisms: Implications for function, disease susceptibility and immunotherapy," *Tissue Antigens*, vol. 61:189-202 (2003).

Wang, Yaning et al., "Biological activity of bevacizumab, a humanized anti-VEGF antibody in vitro," *Angiogenesis*, vol. 7:335-345 (2005).

Zoon, Kathryn C., "Points to Consider in the Manufacture and Testing of Monoclonal Antibody Products for Human Use," U.S. Department of Health and Human Services, Food and Drug Administration, Center for Biologics Evaluation and Research, 50 pages (1997).

Parren, P. et al., "On the Interaction of IgG Subclasses with the Low Affinity FcγRIIa (CD32) on Human Monocytes, Neutrophils, and Platelets, Analysis of a Functional Polymorphism to Human IgG2," J. Clin. Invest, vol. 90: 1537-1546 (1992).

Schneider-Merck, T. et al., "Human IgG2 Antibodies against Epidermal Growth Factor Receptor Effectively Trigger Antibody-Dependent Cellular Cytotoxicity but, in Contrast to IgG1, Only by Cells of Myeloid Lineage," The Journal of Immunology, vol. 184:512-520 (2009).

Tax, W.J.M., "Polymorphism in Mitogenic Effect of IgG1 Monoclonal Antibodies Against T3 Antigen on Human T Cells," Nature, vol. 304:445-447 (1983).

* cited by examiner

Non-reduced SDS-PAGE analysis of various HuMax-CD4 batches on 4-12% NuPAGE Bis-Tris gels. Lane 1, Internal Assay Control; Lane 2, MRS-CD4-001; Lane 3, MEV005; Lane 4, BN078; Lane 5, SO118; Lane 6, UNG-MRS-CD4; Lane 7, MOCK-MRS-CD4; Lane 8, M90-MRS-CD4; Lane 9, M50-MRS-CD4; Lane 10, MEV001. Migration of the markers (KDa) is indicated on the left.

Reduced SDS-PAGE analysis of various HuMax-CD4 batches on 10% NuPAGE Bis-Tris gels. Lane 1, Internal Assay Control; Lane 2, MRS-CD4-001; Lane 3, UNG-MRS-CD4; Lane 4, MEV004; Lane 5, MEV005; Lane 6, MEV001; Lane 7, BN078; Lane 8, BO118. Migration of the markers (KDa) is indicated on the left.

Binding to purified FcγRIIIaECD176VHis measured by ELISA

FcγRIIIaECD176VHis binding by control batches of Zanolimumab

- ○ MRS-CD4-001 curve 1
- × MRS-CD4-001 curve 2
- □ MOCK-GMP#3-CD4
- ▲ M50-GMP#3-CD4
- ▼ M70-GMP#3-CD4
- ○ M90-GMP#3-CD4

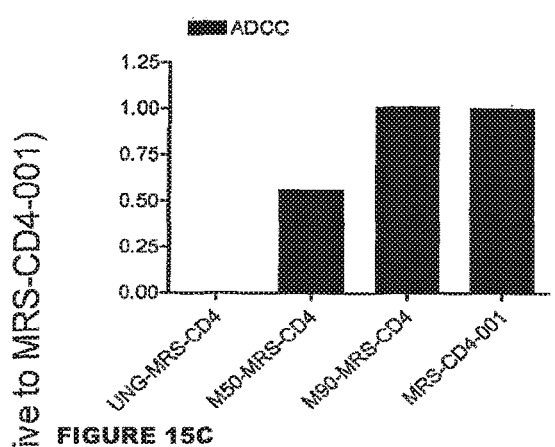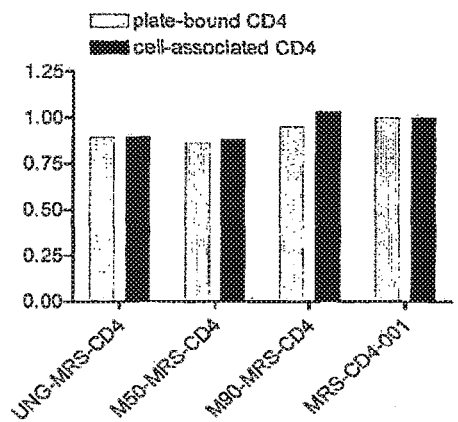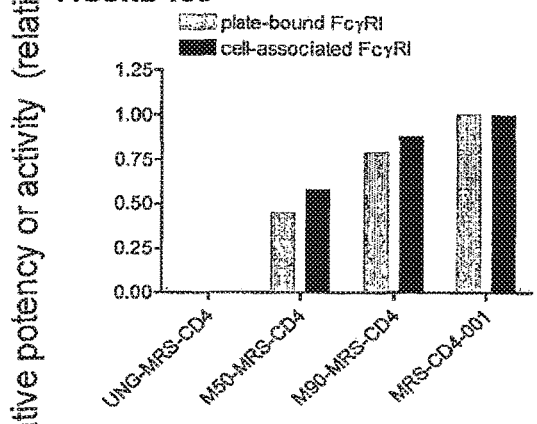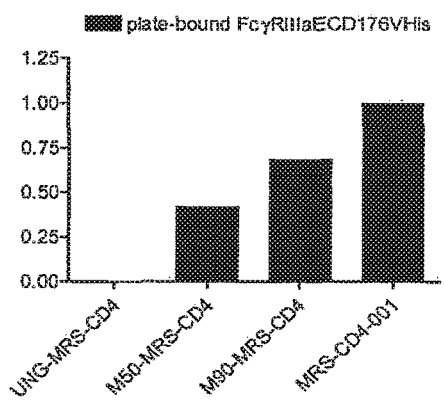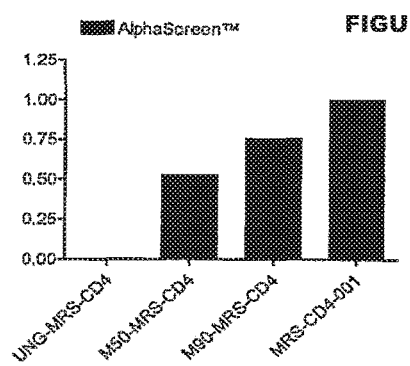

FIGURE 25

Sequence listing

SEQ ID No: 1

```
  1 MWFLTTLLLW VPVDGQVDTT KAVITLQPPW VSVFQEETVT LHCEVLHLPG SSSTQWFLNG
 61 TATQTSTPSY RITSASVNDS GEYRCQRGLS GRSDPIQLEI HRGWLLLQVS SRVFTEGEPL
121 ALRCHAWKDK LVYNVLYYRN GKAFKFFHWN SNLTILKTNI SHNGTYHCSG MGKHRYTSAG
181 ISVTVKELFP APVLNASVTS PLLEGNLVTL SCETKLLLQR PGLQLYFSFY MGSKTLRGRN
241 TSSEYQILTA RREDSGLYWC EAATEDGNVL KRSPELELQV LGLQLPTPVW FHHHHHH
```

SEQ ID No: 2

```
  1 MWQLLLPTAL LLLVSAGMRT EDLPKAVVFL EPQWYRVLEK DSVTLKCQGA YSPEDNSTQW
 61 FHNESLISSQ ASSYFIDAAT VDDSGEYRCQ TNLSTLSDPV QLEVHIGWLL LQAPRWVFKE
121 EDPIHLRCHS WKNTALHKVT YLQNGKGRKY FHHNSDFYIP KATLKDSGSY FCRGLVGSKN
181 VSSETVNITI TQGLAVSTIS HHHHHH
```

SEQ ID No: 3

```
  1 MWQLLLPTAL LLLVSAGMRT EDLPKAVVFL EPQWYRVLEK DSVTLKCQGA YSPEDNSTQW
 61 FHNESLISSQ ASSYFIDAAT VDDSGEYRCQ TNLSTLSDPV QLEVHIGWLL LQAPRWVFKE
121 EDPIHLRCHS WKNTALHKVT YLQNGKGRKY FHHNSDFYIP KATLKDSGSY FCRGLFGSKN
181 VSSETVNITI TQGLAVSTIS HHHHHH
```

SEQ ID No: 4

```
  1 GATCCCGGGG CCGCCACCAT GTGGTTCTTG ACAACTCTGC
```

SEQ ID No: 5

```
  1 CCGTACGTTA GTGATGGTGA TGGTGATGAT GAAACCAGAC AGGAGTTGG
```

SEQ ID No: 6

```
  1 GAAGACTTAA GGCAGCGGCA GAA
```

SEQ ID No: 7

```
  1 TCGGACATCT CATGACTTTC TTT
```

SEQ ID No: 8

```
  1 GATCCCGGGG CCGCCACCAT GTGGCAGCTG CTCCTCCCAA
```

SEQ ID No: 9

```
  1 CGAATTCTTA GTGATGGTGA TGGTGATGTG AGATGGTTGA CACTGCCAA
```

SEQ ID No: 10

```
  1 TACTTCTGCA GGGGGCTTTT CGGGAGTAAA AATGTGTCT
```

FIGURE 25 (Cont'd)

SEQ ID No: 11

1 AGACACATTT TTACTCCCGA AAAGCCCCCT GCAGAAGTA

SEQUENCE LISTING

```
<160> NUMBER OF SEQ ID NOS: 11

<210> SEQ ID NO 1
<211> LENGTH: 298
<212> TYPE: PRT
<213> ORGANISM: Homo Sapiens
<220> FEATURE:
<221> NAME/KEY: MISC_FEATURE
<223> OTHER INFORMATION: FcyRIaECDHis

<400> SEQUENCE: 1

Met Trp Phe Leu Thr Thr Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
```

```
            225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
                260                 265                 270

Ser Pro Glu Leu Glu Leu Gln Val Leu Gly Leu Gln Leu Pro Thr Pro
                275                 280                 285

Val Trp Phe His His His His His His
                290                 295

<210> SEQ ID NO 2
<211> LENGTH: 206
<212> TYPE: PRT
<213> ORGANISM: Homo Sapiens
<220> FEATURE:
<221> NAME/KEY: MISC_FEATURE
<223> OTHER INFORMATION: FcγRII
<220> FEATURE:
<221> NAME/KEY: MISC_FEATURE
<223> OTHER INFORMATION: FcγRIIIaECD176VHis

<400> SEQUENCE: 2

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
                35                  40                  45

Gly Ala Tyr Ser Pro Glu Asp Asn Ser Thr Gln Trp Phe His Asn Glu
            50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
                115                 120                 125

His Ser Trp Lys Asn Thr Ala Leu His Lys Val Thr Tyr Leu Gln Asn
            130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
                180                 185                 190

Gly Leu Ala Val Ser Thr Ile Ser His His His His His His
                195                 200                 205

<210> SEQ ID NO 3
<211> LENGTH: 206
<212> TYPE: PRT
<213> ORGANISM: Homo Sapiens
<220> FEATURE:
<221> NAME/KEY: MISC_FEATURE
<223> OTHER INFORMATION: FcγRIIIaECD176FHis

<400> SEQUENCE: 3

Met Trp Gln Leu Leu Leu Pro Thr Ala Leu Leu Leu Leu Val Ser Ala
```

```
                1               5                      10                       15
            Gly Met Arg Thr Glu Asp Leu Pro Lys Ala Val Val Phe Leu Glu Pro
                            20                      25                      30

Gln Trp Tyr Arg Val Leu Glu Lys Asp Ser Val Thr Leu Lys Cys Gln
                        35                      40                      45

Gly Ala Tyr Ser Pro Glu Asp Asn Ser Thr Gln Trp Phe His Asn Glu
                    50                      55                      60

Ser Leu Ile Ser Ser Gln Ala Ser Ser Tyr Phe Ile Asp Ala Ala Thr
            65                      70                      75                      80

Val Asp Asp Ser Gly Glu Tyr Arg Cys Gln Thr Asn Leu Ser Thr Leu
                                85                      90                      95

Ser Asp Pro Val Gln Leu Glu Val His Ile Gly Trp Leu Leu Leu Gln
                            100                     105                     110

Ala Pro Arg Trp Val Phe Lys Glu Glu Asp Pro Ile His Leu Arg Cys
                        115                     120                     125

His Ser Trp Lys Asn Thr Ala Leu His Lys Val Thr Tyr Leu Gln Asn
                    130                     135                     140

Gly Lys Gly Arg Lys Tyr Phe His His Asn Ser Asp Phe Tyr Ile Pro
            145                     150                     155                     160

Lys Ala Thr Leu Lys Asp Ser Gly Ser Tyr Phe Cys Arg Gly Leu Phe
                                165                     170                     175

Gly Ser Lys Asn Val Ser Ser Glu Thr Val Asn Ile Thr Ile Thr Gln
                            180                     185                     190

Gly Leu Ala Val Ser Thr Ile Ser His His His His His
                        195                     200                     205

<210> SEQ ID NO 4
<211> LENGTH: 40
<212> TYPE: DNA
<213> ORGANISM: Artificial
<220> FEATURE:
<223> OTHER INFORMATION: PCR primer sequence

<400> SEQUENCE: 4
gatcccgggg ccgccaccat gtggttcttg acaactctgc                                40

<210> SEQ ID NO 5
<211> LENGTH: 49
<212> TYPE: DNA
<213> ORGANISM: Artificial
<220> FEATURE:
<223> OTHER INFORMATION: PCR primer sequence

<400> SEQUENCE: 5
ccgtacgtta gtgatggtga tggtgatgat gaaaccagac aggagttgg                      49

<210> SEQ ID NO 6
<211> LENGTH: 23
<212> TYPE: DNA
<213> ORGANISM: Artificial
<220> FEATURE:
<223> OTHER INFORMATION: PCR primer sequence

<400> SEQUENCE: 6
gaagacttaa ggcagcggca gaa                                                  23

<210> SEQ ID NO 7
<211> LENGTH: 23
<212> TYPE: DNA
<213> ORGANISM: Artificial
```

```
<220> FEATURE:
<223> OTHER INFORMATION: PCR primer sequence

<400> SEQUENCE: 7
tcggacatct catgactttc ttt                                          23

<210> SEQ ID NO 8
<211> LENGTH: 40
<212> TYPE: DNA
<213> ORGANISM: Artificial
<220> FEATURE:
<223> OTHER INFORMATION: PCR primer sequence

<400> SEQUENCE: 8
gatcccgggg ccgccaccat gtggcagctg ctcctcccaa                        40

<210> SEQ ID NO 9
<211> LENGTH: 49
<212> TYPE: DNA
<213> ORGANISM: Artificial
<220> FEATURE:
<223> OTHER INFORMATION: PCR primer sequence

<400> SEQUENCE: 9
cgaattctta gtgatggtga tggtgatgtg agatggttga cactgccaa              49

<210> SEQ ID NO 10
<211> LENGTH: 39
<212> TYPE: DNA
<213> ORGANISM: Artificial
<220> FEATURE:
<223> OTHER INFORMATION: PCR primer sequence

<400> SEQUENCE: 10
tacttctgca gggggctttt cgggagtaaa aatgtgtct                         39

<210> SEQ ID NO 11
<211> LENGTH: 39
<212> TYPE: DNA
<213> ORGANISM: Artificial
<220> FEATURE:
<223> OTHER INFORMATION: PCR primer sequence

<400> SEQUENCE: 11
agacacattt ttactcccga aaagcccccct gcagaagta                        39
```

US 9,580,506 B2

POTENCY ASSAYS FOR ANTIBODY DRUG SUBSTANCE BINDING TO AN FC RECEPTOR

FIELD OF THE INVENTION

The invention relates to a method of characterizing an antibody, which method is suitable as a potency assay for batch release of a pharmaceutical composition comprising an antibody, specifically for use when applying for marketing authorization for said pharmaceutical composition.

BACKGROUND OF THE INVENTION

When producing a pharmaceutical composition, it is not enough to formulate the drug substance into the drug product, it is also vital that the resulting drug product is approved by the regulatory body in the country in which the pharmaceutical composition is to be used. In the United States, the appropriate regulatory body is the United States Food and Drug Administration (FDA) (www.fda.gov/), and in Europe, it is for instance the European Agency for the Evaluation of Medicinal Products (EMEA) (www.emea.eu.int/).

The approval process is intensely regulated and the drug developers will be required to submit a substantial amount of information regarding the drug product to the regulatory authorities in order to obtain approval. This may include information regarding the potency of the drug product and assays to determine this potency.

Such a potency assay serves to characterize the product, to monitor lot-to-lot consistency and to assure stability of the product, and should therefore be sufficiently sensitive to detect differences which may impact mechanism of action and function of the product and are thereby of potential clinical importance. In addition, it is desirable that the potency assay bears the closest possible relationship to the putative physiological/pharmacological activity of the product.

A suitable potency assay should meet the following primary criteria:
  ability to measure potency value within the product specifications.
  high sensitivity for detection of differences of potential clinical importance.
  close relationship with the mechanism of action and putative physiological/pharmacological activity of the product.

A potency assay selected on basis of the primary criteria should also meet the following secondary criteria:
  sufficiently low intra- and inter-assay variation (to obtain precision needed to support product specifications).
  sufficient robustness
  amendable to high-throughput analysis.

The development of techniques to produce recombinant monoclonal antibodies has prompted a significant amount of research into the therapeutic use of monoclonal antibodies directed against disease targets. Several pharmaceutical compositions comprising monoclonal antibodies have subsequently been approved for marketing or are in clinical development all over the world. The therapeutic utility of an antibody as a drug depends on the ability of the antibody to bind the antigen, but often antibody Fc-mediated activities also play a critical role in the mechanism of action. Indeed, whereas the effect of some antibody drug products are achieved by simply binding of the antibody to the antigen resulting in for instance blocking the access of ligands to the antigen, the performance of certain antibody drug products may in addition depend on effector functions, such as for instance binding of Fc receptors and/or induction of complement activation.

Zanolimumab (also referred to as HuMax-CD4) is a fully human monoclonal antibody with an IgG1 heavy chain and a light chain of the kappa-type (IgG1,κ) directed against human CD4 (EP0854917). Zanolimumab is manufactured in a mammalian cell (CHO) culture and purified by affinity, ion exchange and size exclusion chromatography. The zanolimumab drug substance is formulated at 20 mg/ml in a phosphate buffered saline, pH 7.4 to become the zanolimumab drug product. One mechanism of zanolimumab is to deplete and/or inactivate $CD4^+$ T cells. This may occur via for instance antibody dependent cell-mediated cytotoxicity (ADCC), down-modulation of CD4 expression on the T cell surface, and/or interference with CD4 signal transduction, T cell activation, and T cell proliferation. All these categories of mechanisms of action depend on binding of CD4 antigen by the antigen-binding moiety of zanolimumab located in the Fab fragment. In addition, ADCC and CD4-downregulation require binding of the Fc region of zanolimumab to an Fc receptor. The induction of ADCC has been identified as an important mechanism of action for Zanolimumab.

Zalutumumab (also referred to as HuMax-EGFr) is a human antibody directed against human EGFr with a heavy chain of the IgG1 isotype and a light chain of the kappa type (IgG1,κ) (WO02/100348). Zalutumumab is currently manufactured in a mammalian cell (CHO) suspension culture, expressing Zalutumumab using the GS vector system, and purified by affinity and ion exchange procedures, including specific viral inactivation and removal procedures. The drug product Zalutumumab (20 mg/mL) is formulated by diluting the Zalutumumab drug substance (25 mg/mL) in a buffer containing 50 mM sodium phosphate, 50 mM sodium chloride, 3% (w/v) mannitol, 0.02% (w/v) polysorbate 80 and 0.01% (w/v) EDTA and adjustment to pH 6.0.

Anti-tumor effect in mice was also observed at low HuMax-EGFr-receptor occupancy, which is likely based on the engagement of immune effector mechanisms, in particular ADCC. So, one mechanism of action of HuMax-EGFr, ADCC, is through Fc-FcR interactions.

The potency of antibodies for which Fc binding to Fc receptor plays a critical role for the mechanism of action are traditionally measured by use of biological assays in which the effect assessed is dependent on Fc-Fc receptor binding. Such assays may include ADCC, induction or inhibition of T cell activation requiring antibody cross-linking or the induction or inhibition of cytokine production such as production of interleukin 2 (IL-2). However, such assays are relatively cumbersome, are highly variable because of expected variations due to cell culture or because primary cells are often required. The latter in particular introduces variability because of variations in donor immune status, polymorphisms in expressed genes and variations in cell-type purity. Such biological assays therefore may be less optimal for batch release purposes. There is thus a need for fast, efficient and sensitive potency assays showing a close relationship to the mechanism of action and putative physiological/pharmacological activity of the antibody drug product for use in the production of pharmaceutical compositions particularly comprising antibodies in which mechanism of action is dependent on binding to Fc receptors.

SUMMARY OF THE INVENTION

The present invention provides a method for determining the potency of a drug product comprising an FcR binding peptide, wherein at least one mechanism of action of the FcR binding peptide of the drug product is mediated through the binding of the FcR binding peptide of the drug product to a Fc receptor, wherein said method comprises determining the binding of the FcR binding peptide of the drug product to an Fc receptor.

BRIEF DESCRIPTION OF THE FIGURES

FIG. 4A: The curve fitting was performed using 4 parameter logistic fitting, with the bottom fixed to a common value. FIG. 4B: The curve fitting was performed using 4 parameter logistic fitting with constraints on bottom level, top level, and hill slope. GMP#3 is the patent batch.

FIGS. 15A-15E: Correlation of ability to induce ADCC by zanolimumab batches with relative potencies in several assays. The zanolimumab batches were ranked according to the level of glycosylated heavy chains present and the potential correlation with the results of the several indicated assays are presented. FIG. 15A: ADCC assay (FIG. 3). FIG. 15B: CD4 binding assays (FIG. 9). FIG. 15C: FcγRI binding assays (FIGS. 13 and 14). FIG. 15D: FcγRIIIaECD176VHis binding (FIG. 5). FIG. 15E. sCD4 and FcγRIIIaECD176VHis binding (FIG. 12).

FIG. 24A—Dose-response plots of CD4 expression carried out using purified blood CD4+ T cells incubated with soluble zanolimumab in the presence or absence of monocytes incubated with or without IFNy for 18 hours. FIG. 24B—Dose-response plots of CD4 expression carried out using CD4+ CEM-NKr cells incubated with soluble zanolimumab, F(ab')2 fragments of zanolimumab or the control antibody HuMab-KLH in the presence or absence of THP-1 cells for 18 h. The CD4 expression was measured using a non-competing anti-CD4 antibody MT-477.

FIG. 25, Sequence list:

BRIEF DESCRIPTION OF SEQUENCE LISTING

Figure 1:
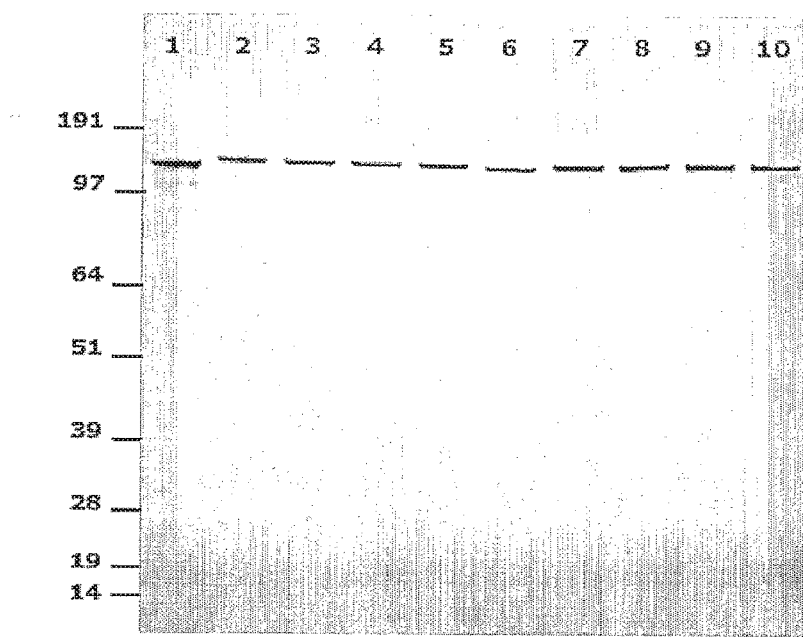
FIG. 1: Non-reduced SDS-PAGE of zanolimumab batches. MEV001, MEV005, MRS-CD4-001, BN078 and BO118 are zanolimumab batches with differences in heavy chain glycosylation. UNG-MRS-CD4 is a de-glycosylated zanolimumab batch (lacking the carbohydrate usually attached to Asn 297 in the antibody Fc), MOCK-MRS-CD4 is a sham-deglycosylated batch, and M90-MRS-CD4 and M50-MRS-CD4 are mixed batches (mix of de-glycosylated and fully glycosylated reference batch) with 90% of heavy chains glycosylated and 50% of heavy chains glycosylated, respectively.

SEQ ID No:1—FcγRIaECDHis
SEQ ID No:2—FcγRIIIaECD176VHis
SEQ ID No:3—FcγRIIIaECD176FHis
SEQ ID No:4—Primer P1
SEQ ID No:5—Primer P2
SEQ ID No:6—Primer P3
SEQ ID No:7—Primer P4
SEQ ID No:8—Primer P5
SEQ ID No:9—Primer P6
SEQ ID No:10—Primer P7
SEQ ID No:11—Primer P8

LIST OF ABBREVIATIONS

ADCC antibody-dependent cellular cytotoxicity
CHO Chinese hamster ovary
ELISA enzyme-linked immunosorbent assay
F(ab')$_2$ dimer of variable domain of an antibody
Fc constant domain of antibody
FcR Fc receptor
FcγRIa Immunoglobulin gamma Fc receptor I-A
FcγRIaECDHis The extracellular domain of FcγRIa with a C-terminal His6 tag
FcγRIIIa Immunoglobulin gamma Fc region receptor III-A
FcγRIIIa176V FcγRIIIa having a Val in position 176, also termed FcγRIII158V, when numbered from the expected start of the matured, processed protein
FcγRIIIaECD176FHis The extracellular domain of FcγRIIIa with a C-terminal His6 tag and the 176F polymorphism
FcγRIIIaECD176VHis The extracellular domain of FcγRIIIa with a c-terminal His6 tag and the 176V polymorphism
FcγRIII158V See above under FcγRIIIa176V
Fv variable (antigen-specific) domain of an antibody
IgG1,κ immunoglobulin G with kappa light chain
IL interleukin
NK natural killer
PBMC peripheral blood mononuclear cell(s)
PBS phosphate-buffered saline
PBSC PBS containing 2% (v/v) chicken serum
PBST PBS containing 0.05% (v/v) Tween-20

PBSTC PBS containing 0.05% (v/v) Tween-20 and 2% (v/v) chicken serum
PMN polymorphonuclear leukocytes
RT room temperature
RZPD Deutsches Resourcenzentrum für Genomforschung
SDS-PAGE SDS polyacrylamide gel electrophoresis
TNF tumor necrosis factor

DETAILED DESCRIPTION OF THE INVENTION

The present invention provides a method which is suitable as a potency assay for batch release of a pharmaceutical composition comprising a peptide capable of binding to the Fc binding region of an Fc receptor. In the context of this application, such a peptide may be termed an "Fc receptor binding peptide" or "FcR binding peptide".

The present invention provides a method for determining the potency of a drug product comprising an FcR binding peptide, wherein at least one mechanism of action of the FcR binding peptide of the drug product is mediated through the binding of the FcR binding peptide of the drug product to a Fc receptor, wherein said method comprises determining the binding of the FcR binding peptide of the drug product to an Fc receptor.

The term peptide in this context includes any suitable peptide and can be used synonymously with the terms polypeptide and protein, unless otherwise stated or contradicted by context; provided that the reader recognize that each type of respective amino acid polymer-containing molecule can be associated with significant differences and thereby form individual embodiments of the present invention (for example, a peptide such as an antibody, which is composed of multiple polypeptide chains, is significantly different from, for example, a single chain antibody, a peptide immunoadhesin, or single chain immunogenic peptide). Therefore, the term peptide herein should generally be understood as referring to any suitable peptide of any suitable size and composition (with respect to the number of amino acids and number of associated chains in a protein molecule), which are capable of binding an Fc receptor. Moreover, peptides in the context of the inventive methods described herein may comprise non-naturally occurring and/or non-L amino acid residues, unless otherwise stated or contradicted by context.

Unless otherwise stated or contradicted by context, the term peptide (and if discussed as individual embodiments of the term(s) polypeptide and/or protein) also encompasses derivatized peptide molecules. Briefly, in the context of the present invention, a derivative is a peptide in which one or more of the amino acid residues of the peptide have been chemically modified (for instance by alkylation, acylation, ester formation, or amide formation) or associated with one or more non-amino acid organic and/or inorganic atomic or molecular substituents (for instance a polyethylene glycol (PEG) group, a lipophilic substituent (which optionally may be linked to the amino acid sequence of the peptide by a spacer residue or group such as β-alanine, γ-aminobutyric acid (GABA), L/D-glutamic acid, succinic acid, and the like), a fluorophore, biotin, a radionuclide, etc.), see for instance U.S. Pat. No. 4,766,106, U.S. Pat. No. 4,179,337, U.S. Pat. No. 4,495,285 and U.S. Pat. No. 4,609,546. An FcR binding peptide may also or alternatively comprise non-essential, non-naturally occurring, and/or non-L amino acid residues, unless otherwise stated or contradicted by context. Non-limiting examples of such amino acid residues include for instance 2-aminoadipic acid, 3-aminoadipic acid, β-alanine, β-aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allohydroxylysine, 3-hydroxyproline, 4-hydroxyproline, isodesmosine, alloisoleucine, N-methylglycine, N-methylisoleucine, 6-N-methyllysine, N-methylvaline, norvaline, norleucine, ornithine, and statine halogenated amino acids.

The term FcR binding peptide in this context thus also includes fusion proteins, which may comprise any suitable amino acid sequence or combination of sequences, which confers binding to the Fc binding region of Fc receptors and at least one nonhomologous and typically substantially amino acid sequence that imparts a detectable biological function and/or characteristic to the fusion protein that cannot solely be attributed to the Fc receptor specific sequence (which may for instance be an antibody as described herein), such as for instance increased in vivo half-life, fluorescence, addition of an epitope tag, increased targeting to a particular type of cell, etc. Functional sequences of such fusion proteins may be separated by flexible linker(s). Secondary sequence(s) may also be derived from cytotoxic or apoptotic peptides. Secondary sequences may also confer diagnostic properties. Examples of such sequences include those derived from easily visualized enzymes such as horseradish peroxidase.

An FcR binding peptide also covers a peptide capable of binding to the Fc binding part of an Fc receptor, which peptide is conjugated to a therapeutic moiety. For instance, such a therapeutic moiety could be a cytotoxin, a chemotherapeutic drug, an immunosuppressant, or a radioisotope. The therapeutic moiety need not be construed as limited to classical chemical therapeutic agents, but may also include a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors and apoptotic inducing protein isolated from mitochondria. It could also be an agent active at the cell surface, such as phospholipase enzymes, e.g. phospholipase C.

An FcR binding peptide also covers an FcR binding peptide conjugated to for instance a radioisotope, a radionuclide, an enzyme (such as for instance an enzyme useful for detection, such as horseradish peroxidase, β-galactosidase, luciferase, alkaline phosphatase, glucose oxidase, and the like), an enzyme substrate, a cofactor, a fluorescent marker (such as for instance fluorescein, fluorescein isothiocyanate, rhodamine, 5-dimethylamine-1-napthalenesulfonyl chloride, lanthanide phosphors, and the like as well as a $^{125}Eu$ label, an isothiocyanate label, a phycoerythrin label, a phycocyanin label, an allophycocyanin label, an o-phthaldehyde label, or a fluorescamine label or the like), a chemiluminescent marker (such as for instance luminal labels, isoluminal labels, aromatic acridinium ester labels, imidazole labels, acridinium salt labels, oxalate ester labels, a luciferin labels, luciferase labels, aequorin labels, and the like), a peptide tag (such as for instance a predetermined polypeptide epitopes recognized by a secondary reporter, such as leucine zipper pair sequences, binding sites for secondary antibodies, metal binding domains, epitope tags, etc.), a magnetic particle, nucleic acids or nucleic acid-associated molecule (such as a cytotoxic ribonuclease, an antisense nucleic acid, an inhibitory RNA molecule (e.g., a siRNA molecule), an aptamer, a ribozyme, a triplex forming molecule, an external guide sequence, an immunostimulatory nucleic acid, an expression cassette coding for expression of for instance a tumor suppressor gene, anti-cancer vaccine, anti-cancer cytokine, apoptotic agent or one or more cytotoxic proteins), nucleases, hormones, immunomodulators, chelators, boron compounds, photoactive agents, dyes, and the like.

An FcR binding peptide also covers an FcR binding peptide comprising one or more radiolabeled amino acids or spin-labeled molecules are provided. Nonlimiting examples of radio-labels for polypeptides include, but are not limited to $^{3}H$, $^{14}C$, $^{15}N$, $^{35}S$, $^{90}Y$, $^{99}Tc$, $^{125}I$, $^{131}I$, and $^{186}Re$.

An FcR binding peptide also covers cross-linked FcR binding peptide derivatives. For example, such a cross-linked derivative may be produced by crosslinking two or more antibodies, at least one of which is capable of binding to the Fc binding region of an Fc receptor (of the same type or of different types, e.g., to create bispecific antibodies).

The methods of the present invention can also be used to determine the potency if peptide mimetics capable of binding the Fc binding region of Fc receptors. These are thus also included in the term FcR binding peptides.

A drug product is a composition comprising the therapeutically interesting drug, which composition is to be administered to patients in need of treatment with the drug. In one embodiment, the drug product is a drug product comprising an antibody, such as a recombinantly produced antibody drug. In the case of a recombinant antibody drug, the antibody drug product is produced by first producing the antibody in a host cell either generated by cell fusion of recombinant DNA techniques, followed by harvesting, purification and formulation of the antibody resulting in the drug product. The selection of the cell type for antibody production, co-transfection of modifying enzymes such as carbohydrate transferases and differences in culture and/or process conditions may affect the potency of the resulting antibody as it is well known in the art. Likewise for the production of a recombinantly produced peptide. Methods for harvesting, purification and formulation of recombinant antibodies are known in the art and may include one or more steps of for instance clarification, concentration, filtration, and chromatography (such as for instance size exclusion and ion-exchange chromatography). The drug product may, in addition to the drug, contain any number of components, which may be added for instance during the process of purification, which components should be acceptable for pharmaceutical use, such as carriers, diluents, adjuvants and excipients. Examples of pharmaceutically acceptable carriers or diluents as well as any other known adjuvants and excipients are Well known in the art and may be such as those disclosed in Remington: The Science and Practice of Pharmacy, 19th Edition, Gennaro, Ed., Mack Publishing Co., Easton, Pa., 1995.

The term antibody in the context of the present invention refers to an immunoglobulin molecule, a fragment of an immunoglobulin molecule, or a derivative of either thereof, which has the ability to specifically bind to an antigen under typical physiological conditions for significant periods of time such as with a half-life of at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen) and the ability to bind Fc receptors.

The term immunoglobulin refers to a class of structurally related glycoproteins consisting of two pairs of polypeptide chains, one pair of light (L) low molecular weight chains and one pair of heavy (H) chains, typically all four are interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$) and a heavy chain constant region. The heavy chain constant region typically is comprised of three domains, $C_H1$, $C_H2$, and $C_H3$. Each light chain typically is comprised of a light chain variable region (abbreviated herein as $V_L$) and a light chain constant region. The light chain constant region typically is comprised of one domain, $C_L$. The $V_H$ and $V_L$ regions can be further subdivided into regions of hypervariability (or hypervariable regions which can be hypervariable in sequence and/or form of structurally defined loops), also termed complementarity determining regions (CDRs), interspersed with regions that are more conserved, termed framework regions (FRs).

Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases such as variable domain residue numbering as in Kabat or according to Kabat herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$ CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

In an antibody, the variable regions of the heavy and light chains of the immunoglobulin molecule contain a binding domain that interacts with an antigen (the Fv fragment). The constant regions of the antibodies (Abs) may mediate the binding of the immunoglobulin to host tissues or factors, including various cells of the immune system (such as effector cells) via Fc receptors and the first component (Clq) of the classical complement system.

An antibody for use in the present invention may be a bispecific antibody or similar molecule. Indeed, bispecific antibodies and the like may bind any suitable target in addition to a portion of the original antigen as long as they retain a part capable of binding to an Fc receptor.

As indicated above, the term antibody herein, unless otherwise stated or clearly contradicted by context, includes fragments, derivatives, variants (incl. deletion variants) of an antibody that retain the ability to specifically bind to an antigen and to an Fc receptor. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Other forms of single chain antibodies, such as molecules described in WO2005037989, are included within the term antibody. Although such fragments are generally included within the meaning of antibody, they collectively and each independently are unique features of the present invention, exhibiting different biological properties and utility.

It also should be understood that the term antibody also generally includes polyclonal antibodies, monoclonal antibodies, such as chimeric antibodies, humanized antibodies and human antibodies as well as antibody-like polypeptides, An antibody can be of a specific isotype referring to the immunoglobulin class that is encoded by heavy chain constant region genes, for instance IgG1, IgG2, IgG3, IgG4, IgD, IgA, IgE, or IgM. Each isotype has a unique amino acid sequence and possesses a unique set of isotype epitopes distinguishing them from each other.

A therapeutic effect of an antibody is achieved through the binding of the hypervariable region of the antibody to the antigen and the binding of the Fc region of the antibody to an Fc receptor. A therapeutic peptide may also provide its therapeutic effect through the binding to an Fc receptor.

Fc receptors belong to a family of receptors specific for certain amino acids in the constant region of immunoglobulins. Their expression on individual cells depends on the type of receptor. Receptors for almost all immunoglobulin classes have been described. They are referred to as FcγR (for the IgG class), FcαR (for IgA class) and FcεR (for IgE class). Multiple FcγRS have been identified which differ in their affinity to bind IgG and relative affinity to bind IgG isotypes; for more information on the FcγR receptors, please see van Sorge N M et al., Tissue Antigens. 61(3), 189-202 (2003). Fc receptors for use in the present invention may be full-length Fc receptors or fragments thereof which fragment retains the ability to bind an Fc region, for instance the extracellular domain. An Fc receptor for use in the present invention may also be a wildtype Fc receptor of any allotype or a mutant variant thereof, the function of which correlates with the function of an Fc receptor, to which the FcR binding peptide binds in vivo. An Fc receptor for use in the present invention may also be a peptide, which are not a naturally occurring Fc receptor (or a fragment or derivate thereof), which peptide is capable of binding the FcR binding region of the Fc part of an antibody and wherein the binding of the FcR binding peptide to the Fc binding peptide correlates with the function of a Fc receptor, to which the FcR binding peptide binds in vivo.

Fc receptors for use in the present invention may for instance be produced by transient expression in host cells as described, in the examples section, or may be produced in stably transfected cell lines or in any other way known in the art. They may also be present on the surface of a cell, such as a eukaryotic cell, for instance a yeast cell or a mammalian cell, transfected with nucleic acid enabling expression of an Fc receptor comprising a transmembrane domain. The term "host cell" (or recombinant "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, NS/0 cells, and lymphocytic cells.

As shown herein, there is a strong correlation between the ability of a drug product containing a peptide, which is dependent for its mechanism of action on the recruitment of cells expressing the Fc receptor, to bind an Fc receptor, and the therapeutic effect of the peptide drug product when administered to a patient in need thereof.

The potency of a drug product is a measure of the activity in a specific assay relative to the activity of a reference standard of the drug product for which therapeutic efficacy may have been assessed. For peptides, such as antibodies, inter alia acting by binding an Fc receptor, a method according to the present invention is suitable for use in determining the potency of the peptide drug product as the binding of the peptide to the Fc receptor is a direct indication of a mechanism of action of the peptide. Use of a method according to the invention thus enables determining the potency of an FcR binding peptide without the use of cumbersome bioassays, such as determination of the production of IL-2 or the induction of ADCC, where the determination of the potency depends on measurements of the effects of the binding of the FcR binding peptide to the Fc receptor in a cell-based assay, whereas the use of a method according to the present invention enables determination of the potency by simply measuring the binding of the FcR binding peptide to the Fc receptor.

The present invention also provides a method for determining the potency of a drug product comprising an FcR binding peptide, which method comprises
  i) determining the binding of a reference standard FcR binding peptide to an Fc receptor;
  ii) determining the binding of the FcR binding peptide of the drug product to said Fc receptor; and
  iii) comparing the FcR binding in step ii) to the FcR binding in step i) and using the information obtained by the comparison to assess the potency of the drug substance,
wherein
  a) the binding to the Fc receptor in step ii) is determined in the same manner as the binding to the Fc receptor in step i),
  b) at least one mechanism of action of the FcR binding peptide of the drug product is mediated through the binding of the FcR binding peptide to a Fc receptor, and
  c) wherein the reference standard FcR binding peptide and the FcR binding peptide of the drug product are two different preparations of the same FcR binding molecule.

This method is useful for analyzing different batches from for instance the production of a given FcR binding peptide. The binding of the FcR binding peptide of the drug product to the Fc receptor is compared to the binding of reference standard FcR binding peptide to the Fc receptor, and the therapeutic efficacy of the FcR binding peptide of the drug product is assessed from its ability to bind the Fc receptor to the same or substantially the same degree as the reference standard FcR binding peptide. The potency of the reference standard FcR binding peptide may for instance also be established through the use of other methods such as cell-based methods or inhibition of IL-2 production to establish that the reference standard FcR binding peptide does indeed have the desired therapeutic activity. According to the present invention, the FcR binding profile of the reference standard FcR binding peptide is a suitable indicator for the potency of the reference standard FcR binding peptide and any FcR binding peptide showing the same or substantially the same FcR binding profile as the reference standard FcR binding peptide is deemed to have the same or substantially the same therapeutic activity as the reference standard FcR binding peptide. The degree to which the FcR binding profile of the FcR binding peptide of the drug product and the FcR binding profile of the reference standard FcR binding peptide may differ may be established on a case-to-case basis and may for instance be determined in cooperation with the appropriate regulatory body.

To be able to determine FcR binding in a reliable and consistent manner, the FcR binding of the FcR binding peptide of the drug product and the reference standard FcR binding peptide should be performed using the same assay, for instance assays as described elsewhere herein. The determination of the binding of the reference standard FcR binding peptide will typically be performed first to establish a standard that any following batches of the FcR binding peptide can be compared with. However, the determination of the binding of the reference standard FcR binding peptide may also be performed at the same time or after the determination of the FcR binding of the FcR binding peptide of the drug product.

The present invention also provides a method of producing a pharmaceutical composition comprising an FcR binding peptide, which method comprises
a) the production of a drug product comprising said FcR binding peptide;
b) subjecting said drug product to a method as described above for determining the potency of a drug product comprising an FcR binding peptide; and
c) using the information obtained in step b) as part of an assessment of whether the drug product may be used as a pharmaceutical composition.

The production of the drug product may be performed in any manner as desired and/or suitable for the drug product and/or peptide in question. The drug product should then be subjected to a method for assaying the binding of the peptide of the drug product to an Fc receptor. The result of said method should then be taken as an indication of whether the drug product may be used as a pharmaceutical composition, i.e. whether the drug product lives up the criteria to be injected into a patient as agreed with the regulatory authorities in a country, where an injection of the drug product may take place.

The present invention also provides a method as described above, wherein said method is part of an application for marketing authorization for selling said drug product as a pharmaceutical composition.

The present invention also provides a method for applying for marketing authorization for a drug product comprising an FcR binding peptide, which method comprises describing a method as described above for determining the potency of the FcR binding peptide of the drug product.

In one embodiment, the method according to the present invention for determining the potency of a drug product comprising an FcR binding peptide is used as a potency assay for batch release.

Any continuing production of drug products will result in the production of different batches of product to be released as pharmaceuticals. A key feature in the production is to ensure that the different batches live up to the same standard. This standard is typically set in cooperation with the regulatory bodies. Typically, each batch will be tested and examined by a number of different assays to ensure that the batch is of sufficient quality to be approved for the market. One of such assays may be, and often is, a potency assay to determine that the drug product has the required potency. In the case of drug products comprising recombinant peptides, such as recombinant antibodies, such potency is often dependent of the quality of the recombinantly produced peptide. In the case of antibodies mediating their effect through binding of an Fc receptor, the quality of the antibody in this respect is often dependent on the glycosylation of the Fc part of the antibody. However, determining the glycosylation of the Fc part of the antibody, and other known methods of determining the potency, such as methods measuring the ability of the drug product to initiate ADCC or measuring the inhibition of T cell signal transduction (for instance measuring the up-regulation of activation markers and/or proliferation and production of autocrine factors) directly or indirectly are often to cumbersome or variable for efficient and reliable use in a production process. However, as described elsewhere herein, a method according to the present invention is suitable for use in determining the potency of the antibody drug product and is therefore a suitable assay for use as potency assay for batch release.

In one embodiment, the binding of the FcR binding peptide to the Fc receptor is determined by use of a method comprising
(i) bringing a sample of the drug product into contact with an Fc receptor for a time period sufficient for allowing the FcR binding peptide to bind to the Fc receptor, and
(ii) detecting the amount of FcR binding peptide bound to the Fc receptor.

In a further embodiment, the detection is performed by use of a detecting antibody directed at the FcR binding peptide. In a further embodiment, the detecting antibody is a labeled antibody.

In one embodiment, the binding of the FcR binding peptide, such as an antibody, to the Fc receptor is determined by use of an ELISA (enzyme-linked immunosorbent assay); see for instance Margulies D. H. 199. Induction of immune responses. In Current Protocols in Immunology (Coligan, J. E., Kruisbeek, A. M., Margulies, D. H., Shevach, E. M., Strober, W., eds. pp. 2.1.2-2.1.20 John Wiley & Sons, New York).

In one embodiment, the binding of the FcR binding peptide, such as an antibody, to the Fc receptor is determined by use of an AlphaScreen™ assay. Briefly, acceptor beads are used to immobilize the FcR protein, the donor beads will be coated with the antigen of interest (for instance sCD4). Different coating systems may be used and the acceptor and donor beads may be interchanged. The acceptor and donor beads will come into proximity (approximately <200 nm) as a result of biological binding of the test antibody to an Fc receptor and to antigen. Upon excitation at 680 nm, a photosensitizer in the donor bead will convert ambient oxygen to a singlet state. Singlet oxygen molecules diffuse across to react with a thioxene derivate in the acceptor bead resulting in chemiluminescence. This chemiluminescence will activate fluorophores in the acceptor bead which causes light emission at 520-620 nm (www.perkinelmer.co.jp/tech/tech_ls/protocol_collection/asc-001-.pdf).

In one embodiment, the binding of the FcR binding peptide, such as an antibody, to the Fc receptor is determined by use of a radioimmunoassay (Cooper, H. M., and Paterson, Y. Determination of the specific antibody titer. In Current Protocols in Molecular Biology (Ausubel, F. M., Brent, R., Kingston, R. E., Moore, D. D., Seidman, J. G., Smith, J. A, and Struhl, K, eds.) pp. 11.17.1-11.17.13 John Wiley & Sons, New York, 1993)

In one embodiment, the binding of the FcR binding peptide, such as an antibody, to the Fc receptor is determined by use of a BIAcore assay. The BIAcore works by the principle of surface plasmon resonance (SPR), which allows for measurements of changes in refractive index at a surface. Briefly, one interactant (the ligand eg an Fc receptor) is immobilized to the surface of a sensor chip. A solution containing potential binding partner(s) (the antibody of the drug product) is passed over the immobilized surface, and binding is visualized as a change in refractive index at the surface (response units (RU)) over time (D. G. Myszka and R. L. Rich, Implementing surface plasmon resonance biosensors in drug discovery, Pharm. Sci. Technol. Today 3, 310-317 (2000). In one embodiment, the binding of the FcR binding peptide such as an antibody, to the Fc receptor is determined by an acoustic biosensor such as the Akubio (for information: www.akubio.com/).

In one embodiment, the binding of the FcR binding peptide, such as an antibody, to the Fc receptor is determined by use of an (fluorometric microvolume assay technology) FMAT, e.g. FLISA (fluorescent-linked immunosorbent assay). Briefly, beads are used to immobilize the FcR protein (e.g. streptavidin beads with biotinylated-FcR), the antibody is added, and detected with Cy5-conjugated anti-IgG, which will be read in by the FMAT. Different coating and detection systems may be used (Miraglia, S. et al, J Biomol Screen. 4, 193-204 (1999).

In one embodiment, the binding of the FcR binding peptide, such as an antibody, to the Fc receptor is determined by use of a (dissociation-enhanced lanthanide fluorescent immunoassay) DELFIA. Briefly in the DELFIA assay, also known as time-resolved fluorescence immunoassay, the antibody is captured (for instance using anti-human IgG) to a microtiter plate, and binding of FcR is measured by adding biotinylated FcR, which is detected with for instance Eu-(europium) labeled streptavidin. An enhancement step with enhancement solution is employed before counting on Delfia Fluorometer, eg a VICTOR apparatus. The VICTOR apparatus operates with a broad array of technologies including fluorescence, luminescence, time-resolved fluorescence, fluorescence polarization and UV absorbance necessary for direct quantification of proteins. Many options and combinations may be used. VICTOR3 multilabel microplate reader for quantitative detection of light emitting or light absorbing markers for cell and microbiology assays, binding studies and DELFIA assays (www.gmi-inc.com/BioTechLab/Wallac%20Delfia%201234%20Fluorometer.htm).

In one embodiment of the present invention, a mechanism of action of the FcR binding peptide of the drug product, such as an antibody, is to induce antibody dependent cell-mediated cytotoxicity (ADCC). ADCC is an immune response in which FcR binding peptides, such as antibodies, by coating target cells, makes them vulnerable to induction of lysis by immune cells, including but not limited to NK cells, PMN or monocyte/macrophages.

In one embodiment of the present invention, a mechanism of action of the FcR binding peptide of the drug product, such as an antibody, is to induce down modulation of the target receptors via i.e. internalization, stripping, capping or other forms of changing receptors rearrangements on the cell surface that influences FcR crosslinking.

In one embodiment of the present invention, a mechanism of action of the FcR binding peptide of the drug product, such as an antibody, is mediated through the recruitment of natural killer cells. Natural killer cells (NK cells) are cells which can react against and destroy another cell without prior sensitization to it and may under certain circumstances not need to recognize a specific antigen. However, NK cells may also be activated to induce ADCC by an antibody Fc region of which the antigen binding domain is bound to an antigen on the target cell.

In one embodiment of the present invention, a mechanism of action of the FcR binding peptide of the drug product, such as an antibody, is mediated through the induction of ADCC through NK cells.

In one embodiment of the present invention, at least one of the Fc receptors to which the FcR binding peptide of the drug product, such as an antibody, binds in vivo is expressed on NK cells.

In one embodiment of the present invention, a mechanism of action of the FcR binding peptide of the drug product, such as an antibody, is mediated through the recruitment of polymorphonuclear leukocytes (PMN).

In one embodiment of the present invention, a mechanism of action of the FcR binding peptide of the drug product, such as an antibody, is mediated through the induction of ADCC through PMNs.

In one embodiment of the present invention, a mechanism of action of the FcR binding peptide of the drug product, such as an antibody, is mediated through the induction of PMN degranulation.

In one embodiment of the present invention, a mechanism of action of the FcR binding peptide of the drug product, such as an antibody, is mediated through the induction of phagocytosis through PMN.

In one embodiment of the present invention, at least one of the Fc receptors to which the FcR binding peptide of the drug product, such as an antibody, binds in vivo is expressed on PMNs.

In one embodiment of the present invention, a mechanism of action of the FcR binding peptide of the drug product, such as an antibody, is to induce platelet aggregation.

In one embodiment of the present invention, a mechanism of action of the FcR binding peptide is mediated through the recruitment of platelets.

In one embodiment of the present invention, at least one of the Fc receptors to which the FcR binding peptide of the drug product, such as an antibody, binds in vivo is expressed on platelets.

In one embodiment of the present invention, a mechanism of action of the FcR binding peptide of the drug product, such as an antibody, is to induce cytokine production.

In one embodiment, a therapeutic activity of the FcR binding peptide of the drug product, such as an antibody, is mediated through the recruitment of natural killer cells and/or T cells.

In one embodiment, at least one of the Fc receptors to which the FcR binding peptide of the drug product, such as an antibody, binds in vivo is expressed on natural killer cells and/or T cells.

In one embodiment of the present invention, a mechanism of action of the FcR binding peptide of the drug product, such as an antibody, is to induce clearance of immune complexes.

In one embodiment, a mechanism action of the FcR binding peptide of the drug product, such as an antibody, is mediated through the recruitment of monocytes or macrophages.

In one embodiment, at least one of the Fc receptors to which the FcR binding peptide of the drug product, such as an antibody, binds in vivo is expressed on monocytes or macrophages.

In one embodiment of the present invention, a mechanism of action of the FcR binding peptide of the drug product, such as an antibody, is to induce down-regulation of antibody responses.

In one embodiment, a mechanism of action of the FcR binding peptide of the drug product, such as an antibody, is mediated through the recruitment of B cells.

In one embodiment, at least one of the Fc receptors to which the FcR binding peptide of the drug product, such as an antibody, binds in vivo is expressed on B cells.

In one embodiment of the present invention, a mechanism of action of the FcR binding peptide of the drug product, such as an antibody, is to induce monocyte and macrophage effector function inhibition.

In one embodiment, a mechanism of action of the FcR binding peptide of the drug product, such as an antibody, FcR binding peptide of the drug product, such as an antibody, is mediated through the recruitment of monocytes and/or macrophages.

In one embodiment, at least one of the Fc receptors to which the FcR binding peptide of the drug product, such as an antibody, binds in vivo is expressed on monocytes and/or macrophages.

In one embodiment of the present invention, a mechanism of action of the FcR binding peptide of the drug product, such as an antibody, is mediated through the induction of ADCC by monocytes or macrophages.

In one embodiment, at least one of the Fc receptors to which the FcR binding peptide binds in vivo is expressed on monocytes and/or macrophages.

In one embodiment of the present invention, a mechanism of action of the FcR binding peptide of the drug product, such as an antibody, is to induce phagocytosis.

In one embodiment, a mechanism of action of the FcR binding peptide of the drug product, such as an antibody, is mediated through the recruitment of polymorphonuclear leukocytes, macrophages and/or dendritic cells.

In one embodiment, at least one of the Fc receptors to which the FcR binding peptide of the drug product, such as an antibody, binds in vivo is expressed on polymorphonuclear leukocytes, macrophages and/or dendritic cells.

In one embodiment of the present invention, a mechanism of action of the FcR binding peptide of the drug product, such as an antibody, is mediated through the induction of phagocytosis by monocytes or macrophages.

In one embodiment, at least one of the Fc receptors to which the FcR binding peptide of the drug product, such as an antibody, binds in vivo is expressed on monocytes or macrophages.

In one embodiment of the present invention, a mechanism of action of the FcR binding peptide of the drug product, such as an antibody, is to induce crosslinking.

In one embodiment of the present invention, a mechanism of action of the FcR binding peptide of the drug product, such as an antibody, is mediated through cross-linking of cells and/or antibodies.

In one embodiment of the present invention, a mechanism of action of the FcR binding peptide of the drug product, such as an antibody, is to induce positive signaling via an immunoreceptor tyrosine-based activation motif.

In one embodiment of the present invention, a mechanism of action of the FcR binding peptide of the drug product, such as an antibody, is mediated through the recruitment of myeloid cells, T cells and/or platelets.

In one embodiment, at least one of the Fc receptors to which the FcR binding peptide of the drug product, such as an antibody, binds in vivo is expressed on myeloid cells, T cells and/or platelets.

In one embodiment of the present invention, a mechanism of action of the FcR binding peptide of the drug product, such as an antibody, is to induce positive signaling via common γ, β, ζ chains.

In one embodiment of the present invention, a mechanism of action of the FcR binding peptide of the drug product, such as an antibody, is mediated through the recruitment of myeloid cells, polymorphonuclear leukocytes, natural killer cells or T cells.

In one embodiment, at least one of the Fc receptors to which the FcR binding peptide of the drug product, such as an antibody, binds in vivo is expressed on myeloid cells, polymorphonuclear leukocytes, natural killer cells or T cells.

In one embodiment of the present invention, a mechanism of action of the FcR binding peptide of the drug product, such as an antibody, is to induce negative signaling through an immunoreceptor tyrosine-based inhibition motif.

In one embodiment of the present invention, a mechanism of action of the FcR binding peptide of the drug product, such as an antibody, is mediated through the recruitment of B cells, macrophages and/or monocytes.

In one embodiment, at least one of the Fc receptors to which the FcR binding peptide of the drug product, such as an antibody, binds in vivo is expressed on B cells, macrophages and/or monocytes.

In one embodiment, the Fc receptor is an FcγRIa receptor or a fragment thereof which fragment retains the ability to bind an Fc region, for instance the extracellular domain. The FcγRIa receptor is constitutively expressed on cells of the reticuloendothelium system and on mononuclear phagocytes, including monocytes, macrophages and dendritic cells and can be induced on polymorphofic neutrophils.

In one embodiment, the Fc receptor is an FcγRIIa receptor or a fragment thereof which fragment retains the ability to bind an Fc region, for instance the extracellular domain. The FcγRIIa receptor is one of the several known isoforms of the FcγRII receptor. FcγRIIa is the most widely distributed isotypes and is expressed on virtually all myeloid cells, including platelets.

In one embodiment, the Fc receptor is an FcγRIIb receptor or a fragment thereof which fragment retains the ability to bind an Fc region, for instance the extracellular domain. The expression of the FcγRIIb receptor is restricted to phagocytes and B cells.

In one embodiment, the Fc receptor is an FcγRIIc receptor or a fragment thereof which fragment retains the ability to bind an Fc region, for instance the extracellular domain. The FcγRIIc receptor is expressed on NK cells.

In one embodiment, the Fc receptor is an FcγRIIIa receptor or a fragment thereof which fragment retains the ability to bind an Fc region, for instance the extracellular domain. In a further embodiment, the FcγRIII receptor is an FcγRIIIa176V receptor or a fragment thereof which fragment retains the ability to bind an Fc region, for instance the extracellular domain. The FcγRIIIa receptor is one of the two known isoforms of the FcγRIII receptor. FcγRIIIa is present on monocytes, macrophages, NK cells and γ/δ T cells. A genetic polymorphism of FcγRIIIa is present in position 176 (Phe or Val). This variant, FcγRIIIa176V (also termed FcγRIII158V, when numbered from the expected start of the matured, processed protein), is described in Koene H R et al., Blood 90, 1109-1114 (1997) and in Wu J, et al., J Clin Invest. 100, 1059-1070 (1997).

In one embodiment, the Fc receptor is an FcγRIIIb NA1 receptor or a fragment thereof which fragment retains the ability to bind an Fc region, for instance the extracellular domain. In one embodiment, the Fc receptor is an FcγRIIIb NA2 receptor or a fragment thereof which fragment retains the ability to bind an Fc region, for instance the extracellular domain. The FcγRIIIb receptor is constitutively expressed on neutrophils and can be induced on eosinophils.

In one embodiment, the Fc receptor is an FcγRn receptor or a fragment thereof which fragment retains the ability to bind an Fc region, for instance the extracellular domain. The FcγRn receptor is widely distributed and is expressed on endothelial cells.

In one embodiment of the present invention, the Fc receptor for use in a method according to the invention has been prepared by a preparation method, which preparation method comprises a step, which step results in the Fc receptor having a reduced amount of sialic acid on the N-linked glycosylation as compared to a similar Fc receptor prepared by a preparation method not including such a step.

Such desialylation may be achieved in a number of ways. The Fc receptor may for instance be prepared by recombinant expression in a host cell defective in the mechanisms responsible for sialylation. Expression of polypeptides, which polypeptides would normally possess a certain degree of sialic acid glycosylation, in such sialylation-defective cell cells will result in polypeptide product which have less sialic acid on the N-linked glycosylation than a polypeptide expressed in a non-sialylation defective cell (a cell with non-defective sialylation mechanisms) of otherwise the same type. Examples of sialylation-defective cells include for instance cells defective in expression of sialyltransferases (examples are CHO Lec2 cells), cells defective in expression of the acceptor monosaccharide for sialylation such as galactose (for example CHO Lec1 and CHO Lec19 cells), or cells defective in the expression of enzymes involved in the synthesis of sialic acid such as UDP-GlcNAc-2 epimerase (for example CHO Lec3 cells). Other interference techniques such as RNAi can also be used to generate cells defective in the expression of enzymes involved in the synthesis of sialic acid (for example UDP-GlcNAc-2 epimerase), the sialylation itself (for example α2,3-sialyltransferase or α2,6-sialyltransferase) or in the synthesis of complex type N-linked glycans containing the sialic acid acceptor galactose (for example N-acetylglucosamine transferase I). Such techniques have been applied to a variety of cells, including SP2/0, CHO, BHK, HEK-293, NS0, JURKAT and the like. Alternatively, the protein can be expressed in bacterial, yeast or fungal cells, which cells do not add N-linked glycans (bacteria) or sialic acids to the N-linked glycans, such is the case with fungal or yeast expression.

An Fc receptor with sialic acid on its N-linked glycosylation, for instance resulting from recombinant expression in a non-sialylation defective cell, may also be desialylated by use of methods, which reduce the amount of sialic acid, such as for instance by treatment with a sialidase prior to use in said method. Examples of such sialidases are for instance neuraminidases from *Arhrobacter ureafaciens, Salmonella typhimurium, Vibrio Cholera*, Newcastle disease virus, Hitchner B1 Strain, *Streptococcus pneumoniae* or *Clostridium perfringens*. Such enzymes may be obtained from their endogenous source or after recombinant expression in other hosts such as *E. coli*. The desialylation step may be performed straight after expression of the receptor in the non-desialylation defective cells, i.e. before purification. Alternatively, desialylation may be done when the receptor is bound to the resin used for purification or after purification of the receptor. Alternatively, an expression plasmid containing the DNA sequence of the sialidase may be cotransfected with the expression plasmid encoding the receptor, in which case the transfected cells will secrete both high levels of neuraminidase and of receptor, yielding desialylation of the receptor in situ by the recombinantly produced sialidase.

An Fc receptor resulting from recombinant expression in a non-sialylation defective cell may also be separated during purification into a fraction containing sialic acid and into a fraction lacking sialic acid. Such separations may be performed using lectins specific for sialic acid, such as MAA (*Maackia amurensis* agglutinin) and SNA (*Sambucus nigra* I agglutinin) Separation might also be based on anionic exchange chromatography using for example DAEA sepharose, Sepharose Q or Resource Q.

An Fc receptor may also be desialylated by culturing the cell expressing the receptor and adding an alkanoic acid, such as sodium butyrate to the cell culture as described in WO 9639488.

In one embodiment of the present invention, the FcR binding peptide is an antibody.

In one embodiment of the present invention, the FcR binding peptide is a monoclonal antibody.

In one embodiment of the present invention, the antibody is a bi-specific antibody.

In one embodiment of the present invention, the antibody is an IgG-like molecule which at least contains an Fc-binding moiety.

A monoclonal antibody as used herein refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell.

In one embodiment, the antibody of the drug product is a human antibody.

A human antibody, as used herein, is intended to include antibodies having variable and constant regions derived from human germ line immunoglobulin sequences. The human antibodies of the present invention may include amino acid residues not encoded by human germ line immunoglobulin sequences (for instance mutations introduced by random or site-specific mutagenesis in vitro or by somatic mutation in vivo). However, the term "human antibody", as used herein, is not intended to include antibodies in which CDR sequences derived from the germ line of another mammalian species, such as a mouse, have been grafted onto human framework sequences.

As used herein, a human antibody is "derived from" a particular germ line sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germ line $V_H$ of $V_L$ variable region gene segment. Typically, a human antibody derived from a particular human germ line $V_H$ or $V_L$ variable region gene segment sequence will display no more than 10 amino acid differences, such as no more than 5, for instance no more than 4, 3, 2, or 1 amino acid difference from the amino acid sequence encoded by the germ line immunoglobulin gene.

In one embodiment, the antibody of the drug product is a humanized antibody.

A humanized antibody is an antibody that is derived from a non-human species, in which certain amino acids in the framework and constant domains of the heavy and light chains have been mutated so as to avoid or abrogate an immune response in humans. Humanized forms of non-human (for instance murine) antibodies contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired antigen-binding characteristics such as specificity, and affinity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further optimize antigen binding. In general, a humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. A humanized antibody optionally also will comprise at least a portion of an immunoglobulin constant region (Fc), typically that of a human immunoglobulin. For further details, see Jones et al., Nature 321, 522-525 (1986), Riechmann et al., Nature 332, 323-329 (1988) and Presta, Curr. Op. Struct. Biol. 2, 593-596 (1992).

Humanized antibodies also comprise such antibodies in which CDR grafting of non-human-derived CDRs into a human FR has been performed using CDR repair (Mark Dennis, Genentech, presented at the Twelfth International conference on Human Antibodies and Hybridomas, 10-12 May 2006, San Diego, USA).

In one embodiment, the antibody of the drug product is a chimeric antibody.

Typically, a chimeric antibody refers to an antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see for instance U.S. Pat. No. 4,816,567 and Morrison et al., PNAS USA 81, 6851-6855 (1984)). Chimeric antibodies are produced by recombinant processes well known in the art (see for instance Cabilly et al., PNAS USA 81, 3273-3277 (1984), Morrison et al., PNAS USA 81, 6851-6855 (1984), Boulianne et al., Nature 312, 643-646 (1984), EP125023, Neuberger et al., Nature 314, 268-270 (1985), EP171496, EP173494, WO86/01533, EP184187, Sahagan et al., J. Immunol. 137, 1066-1074 (1986), WO87/02671, Liu et al., PNAS USA 84, 3439-3443 (1987), Sun et al., PNAS USA 84, 214-218 (1987), Better et al., Science 240, 1041-1043 (1988) and Harlow et al., Antibodies: A Laboratory Manual, Cold Spring Harbor Laboratory Press, Cold Spring Harbor, N.Y., (1988)).

In one embodiment, the antibody comprises a monovalent or polyvalent antibody format. This antibody format can be monomeric meaning is a dimer (HL) formed by an H chain associated through disulfide bridges with an L chain. A regular antibody is bivalent and is tetramer ($H_2L_2$) formed by two HL dimers associated through at least one disulfide bridge. A polyvalent antibody may also be produced, for example, by employing a CH region that aggregates (for instance from an IgM H chain, or μ chain). Such antibody could be chimeric or derived from one species.

In one embodiment, the antibody comprises framework alterations in the Fc region, which alterations may be associated with advantageous properties, such as changing the functional or pharmacokinetic properties of the antibodies. For example, a substitution or other modification (insertion, deletion, terminal sequence additions or combination of any thereof) in a framework region or constant domain may be associated with an increase in the half-life of the variant antibody with respect to the parent antibody, or may be made to alter the immunogenicity of the variant antibody with respect to the parent antibody, to provide a site for covalent or non-covalent binding to another molecule, or to alter such properties as complement fixation, for instance resulting in a decrease or increase of C1q binding and CDC or of FcγR binding and antibody-dependent cell-mediated cytotoxicity (ADCC). Substitutions may for example be made in one or more of the amino acid residues 234, 235, 236, 237, 297, 318, 320, and 322 of the heavy chain constant region, thereby causing an alteration in an effector function while retaining binding to antigen as compared with the unmodified antibody, cf. U.S. Pat. No. 5,624,821 and U.S. Pat. No. 5,648,260. Further reference may be had to WO 94/29351, WO 99/54342, WO 00/42072, WO 03/011878, WO 03/085119, WO 04/29207, WO 04/063351, WO 04/065540, WO 04/99249, WO 05/018669, WO 05/044859, U.S. Pat. No. 6,121,022, and to U.S. Pat. No. 6,737,056. Furthermore, Shields et al., J. Biol. Chem. 276, 6591-6604 (2001) teaches combination variants, that improve FcγRIII binding, for instance T256A/S298A, S298A/E333A, and S298A/E333A/K334A.

In one embodiment, the antibody comprises a mutated Fc region which has been optimized for binding to Fc receptor to enhance certain effector function.

In one embodiment, the antibody comprises an Fc carbohydrate which has been produced in a cell line modified to lack or to have reduced activity of certain carbohydrate transferases (such as FUT-8) or to contain additional or overexpress certain carbohydrate transferases.

In one embodiment of the present invention, the antibody of the drug product is an IgG1 antibody. In one embodiment, the antibody is an IgG1,κ antibody. In one embodiment, the antibody is an IgG1,λ antibody.

In one embodiment of the present invention, the peptide is an antibody and the determination of the binding of the antibody of the drug product to an Fc receptor is combined with a method determining the binding of the antibody of the drug product to its antigen.

In one embodiment, said binding of the antibody of the drug product to the antigen is determined by use of a method comprising (i) bringing a sample of the drug product into contact with the antigen for a time period sufficient for allowing the antibody to bind to the antigen, and (ii) detecting the amount of antibody bound to the antigen.

In a further embodiment, said detection is performed by use of a detecting antibody directed at antibody of the drug product. In a further embodiment, said detecting antibody is a labeled antibody.

In one embodiment, the binding of the antibody to its antigen is determined by use of an ELISA. In one embodiment, the ELISA used for determining the binding of the antibody to an Fc receptor is also used for determining the binding of the antibody to its antigen.

In one embodiment, the binding of the antibody to its antigen is determined by use of an AlphaScreen™ assay. In one embodiment, the AlphaScreen™ assay used for determining the binding of the antibody to an Fc receptor is also used for determining the binding of the antibody to its antigen.

In one embodiment, the binding of the antibody to its antigen is determined by use of a radioimmunoassay. In one embodiment, the radioimmunoassay used for determining the binding of the antibody to an Fc receptor is also used for determining the binding of the antibody to its antigen. In a further embodiment, the radioimmunoassay uses beads conjugated with Fc receptor and soluble radioiodonated antigen.

As stated earlier, the antigen specificity of an antibody for use in a method according to the present invention does not influence the ability of the antibody to bind an Fc receptor. The methods of the present invention is thus useful for all antibodies (and other FcR binding peptides), wherein at least one mechanism of action of the antibody is mediated through the binding of the antibody to an Fc receptor, regardless of the antigen specificity of the antibody. However, some embodiments are directed at antibodies having specific antigen specificity.

In one embodiment of the present invention, the antibody of the drug product is an antibody binding to human CD4. In one embodiment, the antibody is an antibody binding to human CD4 as described in WO9713852. In one embodiment, the antibody is an antibody binding to human CD4 as described in U.S. Pat. No. 5,871,732. In one embodiment, the antibody is an antibody binding to human CD4 as described in U.S. Pat. No. 6,309,880 or WO9012868. In one embodiment, the antibody is an antibody binding to human CD4 as described in WO02102853. In one embodiment, the antibody is an antibody binding to human CD4 as described in US2001051709 or WO9110722. In one embodiment, the antibody is an antibody binding to human CD4 as described in U.S. Pat. No. 6,056,956 or U.S. Pat. No. 5,670,150. In one embodiment, the antibody is zanolimumab. In one embodiment, the antibody is kelixamab (IDEC-CE9.1, Biogen IDEC). In one embodiment, the antibody is clenoliximab (IDEC-151, Biogen IDEC). In one embodiment, the antibody is TNX-355 (Hu-5A8, Tanox/Biogen IDEC). In one embodiment, the antibody is TRX-1 (TolerRx/Genentech. In one embodiment, the antibody is IOT4a (13B8.2, Immunotech), priliximab (cM-T412, Centocor). In one embodiment, the antibody is 4162W94 (Glaxo Wellcome).

In one embodiment of the present invention, the antibody of the drug product is an antibody binding to human EGFR. In one embodiment, the antibody is an antibody binding to human EGFR as described in WO9640210. In one embodiment, the antibody is an antibody binding to human EGFR as described in WO04056847 or WO02100348. In one embodiment, the antibody is cetuximab (Erbitux®). In one embodiment, the antibody is Zalutumumab (HuMax-EGFR®) (Genmab A/S).

In one embodiment of the present invention, the antibody of the drug product is an antibody binding to human CD20. In one embodiment, the antibody is an antibody binding to human CD20 as described in WO 94/11026. In one embodiment, the antibody is an antibody binding to human CD20 as described in WO 04/035607 or in WO application PCT/DK2005/00270. In a further embodiment, the antibody is rituximab (Rituxan®, MabThera®). In one embodiment, the antibody is ibritumomab tiuxetan (Zevalin®). In one embodiment, the antibody is tositumomab (Bexxar®). In one embodiment, the antibody is HuMax-CD20® (ofatumumab) (Genmab A/S).

In one embodiment of the present invention, the antibody of the drug product is an antibody binding to human TAC (CD25). In one embodiment, the antibody is an antibody binding to human TAC as described in WO 04/045512. In one embodiment, the antibody is HuMax-TAC® (AB12).

In one embodiment of the present invention, the antibody of the drug product is an antibody binding to human CD3. In one embodiment, the antibody is muromonab (Orthoclone OKT®3)

In one embodiment of the present invention, the antibody of the drug product is an antibody binding to human GPIIb/IIIa.

In one embodiment of the present invention, the antibody of the drug product is an antibody binding to human CD25 (IL-2R). In one embodiment, the antibody is daclizumab (Zenapax®). In one embodiment, the antibody is basiliximab (Simulect®).

In one embodiment of the present invention, the antibody of the drug product is an antibody binding to human TNF-α. In one embodiment, the antibody is infliximab (Remicade®). In one embodiment, the antibody is adalimumab (Humira®).

In one embodiment of the present invention, the antibody of the drug product is an antibody binding to human RSV. In one embodiment, the antibody is palivizumab (Synagis®).

In one embodiment of the present invention, the antibody of the drug product is an antibody binding to human HER-2/neu. In one embodiment, the antibody is trastuzumab (Herceptin®). In one embodiment, the antibody is pertuzumab (Omnitarg™).

In one embodiment of the present invention, the antibody of the drug product is an antibody binding to human CD33.

In one embodiment of the present invention, the antibody of the drug product is an antibody binding to human CD52. In one embodiment, the antibody is alemtuzumab (Campath-1H®).

In one embodiment of the present invention, the antibody of the drug product is an antibody binding to human VEGF. In one embodiment, the antibody is bevacizumab (Avastin®).

In one embodiment of the present invention, the antibody of the drug product is an antibody binding to human CTLA4. In one embodiment, the antibody is MDX-010 (ipilimumab; Medarex, Inc.).

The present invention also provides a method for preparation of an Fc receptor for use in a method for determining the binding of an FcR binding peptide to said Fc receptor, wherein said Fc receptor has been prepared by a method including a step, which step results in the Fc receptor having a reduced amount of sialic acid on the N-linked glycosylation as compared to a similar Fc receptor prepared by a method not including said step.

In one embodiment, the binding of the FcR binding peptide to the Fc receptor is determined by use of a method comprising
(i) bringing the FcR binding peptide into contact with an Fc receptor for a time period sufficient for allowing the FcR binding peptide to bind to the Fc receptor, and
(ii) detecting the amount of FcR binding peptide bound to the Fc receptor.

In one embodiment, the detection is performed by use of a detecting antibody directed at the FcR binding peptide. In a further embodiment, the detecting antibody is a labeled antibody.

In one embodiment, the binding of the FcR binding peptide to the Fc receptor is determined by use of an ELISA.

In one embodiment, the binding of the FcR binding peptide to the Fc receptor is determined by use of an AlphaScreen™ assay.

In one embodiment, the binding of the FcR binding peptide to the Fc receptor is determined by use of a radioimmunoassay.

In one embodiment, the binding of the FcR binding peptide to the Fc receptor is determined by use of a BIAcore™ assay.

In one embodiment, the binding of the FcR binding peptide to the Fc receptor is determined by use of an FMAT.

In one embodiment, the binding of the FcR binding peptide to the Fc receptor is determined by use of a DELFIA.

The present invention also provides a plastic member suitable for coating with polypeptide molecules, wherein the adhesion of the polypeptide molecules to the surface of the plastic member at least in part depends on electrostatic interactions between the polypeptide molecules and the surface of the plastic member, wherein the surface of the plastic member has been coated with a desialylated polypeptide.

In one embodiment, the polypeptide molecule is an Fc receptor. Examples of Fc receptors are described elsewhere herein.

In one embodiment, the plastic member is a microtiter plate, such as a 96 well microtiter plate or similar plates, which are well known in the art, such as for instance a Greiner plate.

In one embodiment, the coated plastic member is suitable for use in a method according to the present invention for determining the potency of a drug product comprising an FcR binding peptide.

In one embodiment, the coated plastic member is to be used in a method according to the present invention for determining the potency of a drug product comprising an FcR binding peptide.

The following is a list of selected embodiments of the present invention.

Embodiment 1

A method for determining the potency of a drug product comprising an FcR binding peptide, wherein at least one mechanism of action of the FcR binding peptide of the drug product is mediated through the binding of the FcR binding peptide of the drug product to a Fc receptor, wherein said method comprises determining the binding of the FcR binding peptide of the drug product to an Fc receptor.

Embodiment 2

A method according embodiment 1 for determining the potency of a drug product comprising an FcR binding peptide, which method comprises
i) determining the binding of a reference standard FcR binding peptide to an Fc receptor;
ii) determining the binding of the FcR binding peptide of the drug product to said Fc receptor; and
iii) comparing the FcR binding in step ii) to the FcR binding in step i) and using the information obtained by the comparison to assess the potency of the drug substance,
wherein
a) the binding to the Fc receptor in step ii) is determined in the same manner as the binding to the Fc receptor in step i),
b) at least one mechanism of action of the FcR binding peptide of the drug product is mediated through the binding of the FcR binding peptide to a Fc receptor, and
c) wherein the reference standard FcR binding peptide and the FcR binding peptide of the drug product are two different preparations of the same FcR binding molecule.

Embodiment 3

A method of producing a pharmaceutical composition comprising an FcR binding peptide, which method comprises
a) the production of a drug product comprising said FcR binding peptide;
b) subjecting said drug product to a method according to embodiment 1 or embodiment 2 for determining the potency of a drug product comprising an FcR binding peptide; and
c) using the information obtained in step b) as part of an assessment of whether the drug product may be used as a pharmaceutical composition.

Embodiment 4

A method according to any of embodiments 1 to 3, wherein said method is part of an application for marketing authorization for selling said drug product as a pharmaceutical composition.

Embodiment 5

A method for applying for marketing authorization for a drug product comprising an FcR binding peptide, which method comprises describing a method according to any of embodiments 1 to 4 for determining the potency of the FcR binding peptide of the drug product.

Embodiment 6

A method according to any of embodiments 1 to 5, where the method for determining the potency of a drug product comprising an FcR binding peptide is used as a potency assay for batch release.

Embodiment 7

A method according to any of embodiments 1 to 6, wherein the binding of the FcR binding peptide to the Fc receptor is determined by use of a method comprising
(i) bringing a sample of the drug product into contact with an Fc receptor for a time period sufficient for allowing the FcR binding peptide to bind to the Fc receptor, and (ii) detecting the amount of FcR binding peptide bound to the Fc receptor.

Embodiment 8

A method according to embodiment 7, wherein the detection is performed by use of a detecting antibody directed at the FcR binding peptide.

Embodiment 9

A method according to embodiment 8, wherein the detecting antibody is a labeled antibody.

Embodiment 10

A method according to any of embodiments 1 to 9, wherein the binding of the FcR binding peptide to the Fc receptor is determined by use of an ELISA.

Embodiment 11

A method according to any of embodiments 1 to 6, wherein the binding of the FcR binding peptide to the Fc receptor is determined by use of an AlphaScreen™ assay.

Embodiment 12

A method according to any of embodiments 1 to 6, wherein the binding of the FcR binding peptide to the Fc receptor is determined by use of a radioimmunoassay.

Embodiment 13

A method according to any of embodiments 1 to 6, wherein the binding of the FcR binding peptide to the Fc receptor is determined by use of a BIAcore™ assay.

Embodiment 14

A method according to any of embodiments 1 to 6, wherein the binding of the FcR binding peptide to the Fc receptor is determined by use of an FMAT.

Embodiment 15

A method according to any of embodiments 1 to 6, wherein the binding of the FcR binding peptide to the Fc receptor is determined by use of a DELFIA.

Embodiment 16

A method according to any of embodiments 1 to 15, wherein a mechanism of action of the FcR binding peptide is to induce antibody dependent cell-mediated cytotoxicity (ADCC), or by downmodulation of target receptors.

Embodiment 17

A method according to any of embodiments 1 to 15, wherein a mechanism of action of the FcR binding peptide is mediated through the induction of ADCC.

Embodiment 18

A method according to any of embodiments 1 to 17, wherein a mechanism of action of the FcR binding peptide is mediated through the recruitment of natural killer cells.

Embodiment 19

A method according to any of embodiments 1 to 18, wherein a mechanism of action of the FcR binding peptide is mediated through the induction of ADCC by natural killer cells.

Embodiment 20

A method according to any of embodiments 1 to 19, wherein at least one of the Fc receptors to which the FcR binding peptide binds in vivo is expressed on natural killer cells.

Embodiment 21

A method according to any of embodiments 17 to 20, wherein the Fc receptor is an FcγRIIIa receptor or a fragment thereof which fragment retains the ability to bind an Fc region.

Embodiment 22

A method according to embodiment 21, wherein the FcγRIII receptor is an FcγRIIIa176V receptor or a fragment thereof which fragment retains the ability to bind an Fc region, for instance the extracellular domain.

Embodiment 23

A method according to any of embodiments 1 to 17, wherein a mechanism of action of the FcR binding peptide is mediated through the recruitment of polymorphonuclear leukocytes.

Embodiment 24

A method according to any of embodiments 1 to 23, wherein a mechanism of action of the FcR binding peptide is mediated through the induction of ADCC by polymorphonuclear leukocytes.

Embodiment 25

A method according to any of embodiments 1 to 24, wherein a mechanism of action of the FcR binding peptide is mediated through the induction of PMN degranulation.

Embodiment 26

A method according to any of embodiments 1 to 25, wherein a mechanism of action of the FcR binding peptide is mediated through the induction of phagocytosis by polymorphonuclear leukocytes.

Embodiment 27

A method according to any of embodiments 1 to 17 or any of embodiments 23 to 26, wherein at least one of the Fc receptors to which the FcR binding peptide binds in vivo is expressed on polymorphonuclear leukocytes.

Embodiment 28

A method according to any of embodiments 23 to 27, wherein the Fc receptor is an FcγRIIa receptor or a fragment thereof which fragment retains the ability to bind an Fc region.

Embodiment 29

A method according to any of embodiments 1 to 17, wherein a mechanism of action of the FcR binding peptide is mediated through the induction of ADCC by monocytes or macrophages.

Embodiment 30

A method according to any of embodiments 1 to 17, or embodiment 29, wherein at least one of the Fc receptors to which the FcR binding peptide binds in vivo is expressed on monocytes and/or macrophages.

Embodiment 31

A method according to any of embodiments 1 to 17, embodiment 29 or embodiment 30, wherein the Fc receptor is an FcγRIIb or a fragment thereof which fragment retains the ability to bind an Fc region.

Embodiment 32

A method according to any of embodiments 1 to 17, wherein a mechanism of action of the FcR binding peptide is to induce platelet aggregation.

Embodiment 33

A method according to any of embodiments 1 to 17 or embodiment 32, wherein a mechanism of action of the FcR binding peptide is mediated through the recruitment of platelets.

Embodiment 34

A method according to any of embodiments 1 to 17, embodiment 32 or embodiment 33, wherein at least one of the Fc receptors to which the FcR binding peptide binds in vivo is expressed on platelets.

Embodiment 35

A method according to any of embodiments 1 to 17 or embodiments 32 to 34, wherein the Fc receptor is an FcγRIIa or a fragment thereof which fragment retains the ability to bind an Fc region.

Embodiment 36

A method according to any of embodiments 1 to 17, wherein a mechanism of action of the FcR binding peptide is to induce cytokine production.

Embodiment 37

A method according to any of embodiments 1 to 17 or embodiment 36, wherein a mechanism of action of the FcR binding peptide is mediated through the recruitment of natural killer cells and/or T cells.

Embodiment 38

A method according to any of embodiments 1 to 17, embodiment 36 or embodiment 37, wherein at least one of the Fc receptors to which the FcR binding peptide binds in vivo is expressed on natural killer cells and/or T cells.

Embodiment 39

A method according to any of embodiments 1 to 17 or any of embodiments 36 to 38, wherein the Fc receptor is an FcγRIa or a fragment thereof which fragment retains the ability to bind an Fc region.

Embodiment 40

A method according to any of embodiments 1 to 17 or any of embodiments 36 to 38, wherein the Fc receptor is an FcγRIIIa or a fragment thereof which fragment retains the ability to bind an Fc region.

Embodiment 41

A method according to any of embodiments 1 to 17, wherein a mechanism of action of the FcR binding peptide is to induce clearance of immune complexes.

Embodiment 42

A method according to any of embodiments 1 to 17 or embodiment 41, wherein a mechanism of action of the FcR binding peptide is mediated through the recruitment of monocytes or macrophages.

Embodiment 43

A method according to any of embodiments 1 to 17, embodiment 41 or embodiment 42, wherein at least one of the Fc receptors to which the FcR binding peptide binds in vivo is expressed on monocytes or macrophages.

Embodiment 44

A method according to any of embodiments 1 to 17 or any of embodiments 41 to 43, wherein the Fc receptor is an FcγRIII or a fragment thereof which fragment retains the ability to bind an Fc region.

Embodiment 45

A method according to any of embodiments 1 to 17 or any of embodiments 41 to 43, wherein the Fc receptor is an FcγRIIa or a fragment thereof which fragment retains the ability to bind an Fc region.

Embodiment 46

A method according to any of embodiments 1 to 17 or any of embodiments 41 to 43, wherein the Fc receptor is an FcγRIIIb or a fragment thereof which fragment retains the ability to bind an Fc region.

Embodiment 47

A method according to any of embodiments 1 to 17, wherein a mechanism of action of the FcR binding peptide is to induce down-regulation of antibody responses.

Embodiment 48

A method according to any of embodiments 1 to 17 or embodiment 47, wherein a mechanism of action of the FcR binding peptide is mediated through the recruitment of B cells.

Embodiment 49

A method according to any of embodiments 1 to 17, embodiment 47 or embodiment 48, wherein at least one of the Fc receptors to which the FcR binding peptide binds in vivo is expressed on B cells.

Embodiment 50

A method according to any of embodiments 1 to 17 or any of embodiments 47 to 49, wherein the Fc receptor is an FcγRIIb or a fragment thereof which fragment retains the ability to bind an Fc region.

Embodiment 51

A method according to any of embodiments 1 to 17, wherein a mechanism of action of the FcR binding peptide is to induce monocyte and macrophage effector function inhibition.

Embodiment 52

A method according to any of embodiments 1 to 17 or embodiment 51, wherein a mechanism of action of the FcR binding peptide is mediated through the recruitment of monocytes and/or macrophages.

Embodiment 53

A method according to any of embodiments 1 to 17, embodiment 51 or embodiment 52, wherein at least one of the Fc receptors to which the FcR binding peptide binds in vivo is expressed on monocytes and/or macrophages.

Embodiment 54

A method according to any of embodiments 1 to 17, wherein a mechanism of action of the FcR binding peptide is to induce phagocytosis.

Embodiment 55

A method according to any of embodiments 1 to 17 or embodiment 54, wherein a mechanism of action of the FcR binding peptide is mediated through the recruitment of polymorphonuclear leukocytes, macrophages and/or dendritic cells.

Embodiment 56

A method according to any of embodiments 1 to 17, embodiment 54 or embodiment 55, wherein at least one of the Fc receptors to which the FcR binding peptide binds in vivo is expressed on polymorphonuclear leukocytes, macrophages and/or dendritic cells.

Embodiment 57

A method according to any of embodiments 1 to 17 or any of embodiments 54 to 56, wherein the Fc receptor is an FcγRIIIb or a fragment thereof which fragment retains the ability to bind an Fc region.

Embodiment 58

A method according to any of embodiments 1 to 17 or any of embodiments 54 to 56, wherein the Fc receptor is an FcγRIIa or a fragment thereof which fragment retains the ability to bind an Fc region.

Embodiment 59

A method according to any of embodiments 1 to 17 or embodiment 54, wherein a mechanism of action of the FcR binding peptide is mediated through the induction of phagocytosis by monocytes or macrophages.

Embodiment 60

A method according to any of embodiments 1 to 17, or embodiment 59, wherein at least one of the Fc receptors to which the FcR binding peptide binds in vivo is expressed on monocytes or macrophages.

Embodiment 61

A method according to any of embodiments 1 to 17, embodiment 59 or embodiment 60, wherein the Fc receptor is an FcγRIIb or a fragment thereof which fragment retains the ability to bind an Fc region.

Embodiment 62

A method according to any of embodiments 1 to 17, wherein a mechanism of action of the FcR binding peptide is to induce crosslinking.

Embodiment 63

A method according to any of embodiments 1 to 17 or embodiment 62, wherein a mechanism of action of the FcR binding peptide is mediated through cross-linking of cells and/or antibodies.

Embodiment 64

A method according to any of embodiments 1 to 17, embodiment 54 or embodiment 63, wherein the Fc receptor is an FcγRIa or a fragment thereof which fragment retains the ability to bind an Fc region.

Embodiment 65

A method according to any of embodiments 1 to 17, embodiment 54 or embodiment 63, wherein the Fc receptor is an FcγRII or a fragment thereof which fragment retains the ability to bind an Fc region.

Embodiment 66

A method according to any of embodiments 1 to 17, embodiment 54 or embodiment 63, wherein the Fc receptor is an FcγRIII or a fragment thereof which fragment retains the ability to bind an Fc region.

Embodiment 67

A method according to any of embodiments 1 to 17, wherein a mechanism of action of the FcR binding peptide is to induce positive signaling via a immunoreceptor tyrosine-based activation motif.

Embodiment 68

A method according to any of embodiments 1 to 17 or embodiment 67, wherein a mechanism of action of the FcR binding peptide is mediated through the recruitment of myeloid cells, T cells and/or platelets.

Embodiment 69

A method according to any of embodiments 1 to 17, embodiment 67 or embodiment 68, wherein at least one of the Fc receptors to which the FcR binding peptide binds in vivo is expressed on myeloid cells, T cells and/or platelets.

Embodiment 70

A method according to any of embodiments 1 to 17 or any of embodiments 67 to 69, wherein the FC receptor is an FcγRIIa or a fragment thereof which fragment retains the ability to bind an Fc region.

Embodiment 71

A method according to any of embodiments 1 to 17 or any of embodiments 67 to 69, wherein the Fc receptor is an FcγRIIc or a fragment thereof which fragment retains the ability to bind an Fc region.

Embodiment 72

A method according to any of embodiments 1 to 17, wherein a mechanism of action of the FcR binding peptide is to induce positive signaling via common γ, β, ζ chains.

Embodiment 73

A method according to any of embodiments 1 to 17 or embodiment 72, wherein a mechanism of action of the FcR binding peptide is mediated through the recruitment of myeloid cells, polymorphonuclear leukocytes, natural killer cells or T cells.

Embodiment 74

A method according to any of embodiments 1 to 17, embodiment 72 or embodiment 73, wherein at least one of the Fc receptors to which the FcR binding peptide binds in vivo is expressed on myeloid cells, polymorphonuclear leukocytes, natural killer cells or T cells.

Embodiment 75

A method according to any of embodiments 1 to 17 or any of embodiments 72 to 74, wherein the Fc receptor is an FcγRIa or a fragment thereof which fragment retains the ability to bind an Fc region.

Embodiment 76

A method according to any of embodiments 1 to 17 or any of embodiments 72 to 74, wherein the Fc receptor is an FcγRIIa or a fragment thereof which fragment retains the ability to bind an Fc region.

Embodiment 77

A method according to any of embodiments 1 to 17 or any of embodiments 72 to 74, wherein the Fc receptor is an FcγRIIIa or a fragment thereof which fragment retains the ability to bind an Fc region.

Embodiment 78

A method according to any of embodiments 1 to 17, wherein a mechanism of action of the FcR binding peptide is to induce negative signaling through an immunoreceptor tyrosine-based inhibition motif.

Embodiment 79

A method according to any of embodiments 1 to 17 or embodiment 78, wherein a mechanism of action of the FcR binding peptide is mediated through the recruitment of B cells, macrophages and/or monocytes.

Embodiment 80

A method according to any of embodiments 1 to 17, embodiment 78 or embodiment 79, wherein at least one of the Fc receptors to which the FcR binding peptide binds in vivo is expressed on B cells, macrophages and/or monocytes.

Embodiment 81

A method according to any of embodiments 1 to 17 or any of embodiments 78 to 80, wherein the Fc receptor is an FcγRIIb or a fragment thereof which fragment retains the ability to bind an Fc region.

Embodiment 82

A method according to any of embodiments 1 to 17, wherein the Fc receptor is an FcγRn or a fragment thereof which fragment retains the ability to bind an Fc region.

Embodiment 83

A method according to any of embodiments 1 to 82, wherein the Fc receptor for use in said method has been prepared by a preparation method including a step, which step results in the Fc receptor having a reduced amount of sialic acid on the N-linked glycosylation as compared to a similar Fc receptor prepared by a preparation method not including such a step.

Embodiment 84

A method according to embodiment 83, wherein the Fc receptor has been expressed in a host cell defective in the mechanisms responsible for sialylation.

Embodiment 85

A method according to embodiment 83, wherein the Fc receptor has been treated with sialidase prior to use in said method.

Embodiment 86

A method according to any of embodiments 1 to 85, wherein the FcR binding peptide is an antibody.

Embodiment 87

A method according to embodiment 86, wherein the FcR binding peptide is a monoclonal antibody.

Embodiment 88

A method according to embodiment 86 or embodiment 87, wherein the FcR binding peptide is a human antibody.

Embodiment 89

A method according to embodiment 86 or embodiment 87, wherein the FcR binding peptide is a humanized antibody.

Embodiment 90

A method according to embodiment 86 or embodiment 87, wherein the FcR binding peptide is a chimeric antibody.

Embodiment 91

A method according to any of embodiments 86 to 90, wherein the FcR binding peptide is an antibody fragment containing an Fc-binding moiety.

Embodiment 92

A method according to any of embodiments 86 to 91, wherein the FcR binding peptide is an IgG1 antibody.

Embodiment 93

A method according to embodiment 92, wherein the FcR binding peptide is an IgG1,λ antibody.

Embodiment 94

A method according to embodiment 92, wherein the FcR binding peptide is an IgG1,κ antibody.

Embodiment 95

A method as described in any of embodiments 86 to 94, wherein the determination of the binding of the antibody to an Fc receptor is combined with a method determining the binding of the antibody to its antigen.

Embodiment 96

A method according to embodiment 95, wherein the binding of the antibody to its antigen is determined by use of a method comprising
(i) bringing a sample of the antibody into contact with the antigen for a time period sufficient for allowing the antibody to bind to the antigen, and
(ii) detecting the amount of antibody bound to the antigen.

Embodiment 97

A method according to embodiment 96, wherein the detection is performed by use of a detecting antibody directed at antibody of the drug product.

Embodiment 98

A method according to embodiment 97, wherein the detecting antibody is a labeled antibody.

Embodiment 99

A method according to any of embodiments 95 to 98, wherein the binding of the antibody to its antigen is determined by use of an ELISA.

Embodiment 100

A method according to embodiment 99, wherein the same ELISA is also used to determine the binding of the antibody to the Fc receptor.

Embodiment 101

A method according to embodiment 95, wherein the binding of the antibody to its antigen is determined by use of an AlphaScreen™ assay.

Embodiment 102

A method according to embodiment 101, wherein the AlphaScreen™ assay is also used to determine the binding of the antibody to the Fc receptor.

Embodiment 103

A method according to embodiment 95, wherein the binding of the antibody to its antigen is determined by use of a radioimmunoassay.

Embodiment 104

A method according to embodiment 103, wherein the radioimmunoassay is also used to determine the binding of the antibody to the Fc receptor.

Embodiment 105

A method according to embodiment 104, wherein the radioimmunoassay uses beads conjugated with Fc receptor and radioiodonated antigen.

Embodiment 106

A method according to any of embodiments 86 to 105, wherein the FcR binding peptide is an antibody binding to human CD4.

Embodiment 107

A method according to embodiment 106, wherein the FcR binding peptide is zanolimumab.

Embodiment 108

A method according to embodiment 106, wherein the FcR binding peptide is keliximab.

Embodiment 109

A method according to embodiment 106, wherein the FcR binding peptide is clenoliximab.

Embodiment 110

A method according to embodiment 106, wherein the FcR binding peptide is TNX 355.

Embodiment 111

A method according to embodiment 106, wherein the FcR binding peptide is TRX-1.

Embodiment 112

A method according to embodiment 106, wherein the FcR binding peptide is IOT4a.

Embodiment 113

A method according to embodiment 106, wherein the FcR binding peptide is 4162W94.

Embodiment 114

A method according to any of embodiments 1 to 94, wherein the FcR binding peptide is an antibody binding to human EGFR.

Embodiment 115

A method according to embodiment 114, wherein the FcR binding peptide is cetuximab.

Embodiment 116

A method according to embodiment 114, wherein the FcR binding peptide is HuMax-EGFR, zalutumumab.

Embodiment 117

A method according to any of embodiments 1 to 94, wherein the FcR binding peptide is an antibody binding to human CD20.

Embodiment 118

A method according to embodiment 117, wherein the FcR binding peptide is rituximab.

Embodiment 119

A method according to embodiment 117, wherein the FcR binding peptide is ibritumomab tiuxetan.

Embodiment 120

A method according to embodiment 117, wherein the FcR binding peptide is tositumomab.

Embodiment 121

A method according to embodiment 117, wherein the FcR binding peptide is HuMax-CD20, ofatumumab.

Embodiment 122

A method according to any of embodiments 1 to 94, wherein the FcR binding peptide is an antibody binding to human TAC.

Embodiment 123

A method according to embodiment 122, wherein the FcR binding peptide is HuMax-TAC.

Embodiment 124

A method according to any of embodiments 1 to 94, wherein the FcR binding peptide is an antibody binding to human CD3.

Embodiment 125

A method according to embodiment 124, wherein the FcR binding peptide is muromonab.

Embodiment 126

A method according to any of embodiments 1 to 94, wherein the FcR binding peptide is an antibody binding to human GPIIb/IIIa.

Embodiment 127

A method according to any of embodiments 1 to 94, wherein the FcR binding peptide is an antibody binding to human CD25.

Embodiment 128

A method according to embodiment 127, wherein the FcR binding peptide is daclizumab.

Embodiment 129

A method according to embodiment 127, wherein the FcR binding peptide is basiliximab.

Embodiment 130

A method according to any of embodiments 1 to 94, wherein the FcR binding peptide is an antibody binding to human TNF-α.

Embodiment 131

A method according to embodiment 130, wherein the FcR binding peptide is infliximab.

Embodiment 132

A method according to embodiment 130, wherein the FcR binding peptide is adalimumab.

Embodiment 133

A method according to any of embodiments 1 to 94, wherein the FcR binding peptide is an antibody binding to human RSV.

Embodiment 134

A method according to embodiment 133, wherein the FcR binding peptide is palivizumab.

Embodiment 135

A method according to any of embodiments 1 to 94, wherein the FcR binding peptide is an antibody binding to human HER-2/neu.

Embodiment 136

A method according to embodiment 135, wherein the FcR binding peptide is trastuzumab.

Embodiment 137

A method according to embodiment 135, wherein the FcR binding peptide is pertuzumab.

Embodiment 138

A method according to any of embodiments 1 to 94, wherein the FcR binding peptide is an antibody binding to human CD33.

Embodiment 139

A method according to any of embodiments 1 to 94, wherein the FcR binding peptide is an antibody binding to human CD52.

Embodiment 140

A method according to embodiment 139, wherein the FcR binding peptide is alemtuzumab.

Embodiment 141

A method according to any of embodiments 1 to 94, wherein the FcR binding peptide is an antibody binding to human VEGF.

Embodiment 142

A method according to embodiment 141, wherein the FcR binding peptide is bevacizumab.

Embodiment 143

A method according to any of embodiments 1 to 94, wherein the FcR binding peptide is an antibody binding to human CTLA4.

Embodiment 144

A method according to embodiment 143, wherein the FcR binding peptide is MDX-010.

Embodiment 145

An drug product comprising an FcR binding peptide, which drug product is approved for use as a pharmaceutical composition, and wherein a method according to any of embodiments 1 to 144 forms part of the application for marketing authorization.

Embodiment 146

A method for preparation of an Fc receptor for use in a method for determining the binding of an FcR binding peptide to said Fc receptor, wherein said Fc receptor has been prepared by a method including a step, which step results in the Fc receptor having a reduced amount of sialic acid on the N-linked glycosylation as compared to a similar Fc receptor prepared by a method not including said step.

Embodiment 147

A method according to embodiment 146, wherein the binding of the FcR binding peptide to the Fc receptor is determined by use of a method comprising
(i) bringing the FcR binding peptide into contact with an Fc receptor for a time period sufficient for allowing the FcR binding peptide to bind to the Fc receptor, and
(ii) detecting the amount of FcR binding peptide bound to the Fc receptor.

Embodiment 148

A method according to embodiment 147, wherein the detection is performed by use of a detecting antibody directed at the FcR binding peptide.

Embodiment 149

A method according to embodiment 148, wherein the detecting antibody is a labeled antibody.

Embodiment 150

A method according to any of embodiments 146 to 149, wherein the binding of the FcR binding peptide to the Fc receptor is determined by use of an ELISA.

Embodiment 151

A method according to any of embodiments 146 to 149, wherein the binding of the FcR binding peptide to the Fc receptor is determined by use of an AlphaScreen™ assay.

Embodiment 152

A method according to any of embodiments 146 to 149, wherein the binding of the FcR binding peptide to the Fc receptor is determined by use of a radioimmunoassay.

Embodiment 153

A method according to any of embodiments 146 to 149, wherein the binding of the FcR binding peptide to the Fc receptor is determined by use of a BIAcore™ assay.

Embodiment 154

A method according to any of embodiments any of embodiments 146 to 149, wherein the binding of the FcR binding peptide to the Fc receptor is determined by use of an FMAT.

Embodiment 155

A method according to any of embodiments any of embodiments 146 to 149, wherein the binding of the FcR binding peptide to the Fc receptor is determined by use of a DELFIA.

Embodiment 156

A method according to the invention or any one of embodiments 1-155, wherein a his-capturing antibody coated on the ELISA plate is used to capture his-tagged FcR or FcR fragment.

Embodiment 157

A plastic member suitable for coating with polypeptide molecules, wherein the adhesion of the polypeptide molecules to the surface of the plastic member at least in part depends on electrostatic interactions between the polypeptide molecules and the surface of the plastic member, wherein the surface of the plastic member has been coated with a desialylated polypeptide.

Embodiment 158

A plastic member according to embodiment 157, wherein the polypeptide molecule is an Fc receptor.

Embodiment 159

A plastic member according to embodiment 157 or embodiment 158, wherein the plastic member is a microtiter plate.

Embodiment 160

A plastic member according to any of embodiments 157 to 159, wherein the plastic member is suitable for use in a method according to any of embodiments 1 to 144.

Embodiment 161

A plastic member according to any of embodiments 157 to 159, wherein the plastic member is to be used in a method according to any of embodiments 1 to 144.

The present invention is further illustrated by the following examples which should not be construed as further limiting.

EXAMPLES

Example 1

Oligonucleotide Primers and PCR Amplification

The indicated primers were dissolved in $H_2O$ to 100 pmol/μl and stored at −20° C. For PCR. PfuTurbo® Hotstart DNA polymerase (Stratagene, Amsterdam, The Netherlands; product#600322) was used according to the manufacturers instructions. Each reaction mix contained 200 μM mixed dNTPs (Roche Diagnostics, Almere, The Netherlands; product#1814362), 6.7 pmol of both the forward and reverse primer, approximately 1 ng template DNA and 1 unit of PfuTurbo® Hotstart DNA polymerase in PCR reaction buffer (supplied with polymerase) in a total volume of 20 μl. PCR reactions were carried out with a TGradient Thermocycler 96 (Whatman Biometra, Goettingen, Germany; product#050-801) using a 30-cycle program: denaturing at 95° C. for 2 min; 30 cycles of 95° C. for 30 sec, a 45-65° C. gradient (or another specific annealing temperature) for 30 sec, and 72° C. for 2 min; final extension at 72° C. for 10 min. If appropriate, the PCR mixtures were stored at 4° C. until further analysis or processing.

Example 2

Screening of Bacterial Colonies by PCR

Bacterial colonies were screened for the presence of vectors containing the desired sequences via colony PCR using the HotStarTaq™ Master Mix Kit (Qiagen; product#203445) and the indicated forward and reverse primers. Selected colonies were lightly touched with a 20 μl pipette tip and touched briefly in 2 ml LB (Luria broth) for small scale culture, and then resuspended in the PCR mix. PCR was performed with a TGradient Thermocycler 96 using a 35-cycle program: denaturation at 95° C. for 15 min; 35 cycles of 94° C. for 30 sec, 55° C. for 30 sec and 72° C. for 2 min; followed by a final extension step of 10 min at 72° C. If appropriate, the PCR mixtures were stored at 4° C. until analysis by agarose gel electrophoresis.

Example 3

Production of FcγRIaECDHis

Construction of pEE13.4FcγRIaECDHis

Plasmid DNA from RZPD clone IRATp970F1154D6 (Deutsche Ressourcenzentrum für Genomforschung (RZPD, Berlin, Germany)) was isolated and used as a template in a PCR with primers P1 (SEQ ID No:4) and P2 (SEQ ID No:5) according to the procedure described in example 1 amplifying the extracellular coding domain (aa 1-292) of human FcγRIa and introducing suitable restriction sites for cloning into pEE13.4 (Lonza Biologics, Slough, UK), an ideal Kozak sequence (GCCGCCACC) and a C-terminal $His_6$-tag. The PCR fragment was gel purified and cloned into pEE13.4. For this, the PCR product was digested with Pfl23II and XmaI and purified. The pEE13.4 vector was digested with Pfl23II and XmaI and the vector fragment was purified. The FcγRIa fragment and the pEE13.4Pfl23II-XmaI vector were ligated and transformed into competent DH5α-T1$^R$ cells (Invitrogen). Eight colonies were checked by colony PCR (using primers P3 (SEQ ID No:6) and P4 (SEQ ID No:7) according to the procedure described in example 2, and two colonies contained an insert of the correct size. From the two positive colonies, 2 ml cultures were grown. Plasmid DNA was isolated and one of the constructs was checked by sequence analysis of the insert and found to be correct. The final vector was named pEE13.4FcγRIaECDHis.

Transient Expression of FcγRIaECDHis in Hek-293F Cells

Freestyle™ 293-F (a HEK-293 subclone adapted to suspension growth and chemically defined Freestyle™ medium, e.g. HEK-293F) cells were obtained from Invitrogen and transfected with pEE13.4FcγRIaECDHis according to the manufacturer's protocol using 293Fectin™ (Invitrogen). The transfectants were cultured according to the manufacturer's protocol, and 1 liter of cell supernatant was used for purification as described below.

Purification of FcγRIaECDHis on BD TALONspin™ (0.5 ml) Talon Column

BD TALONspin™ columns were obtained from Clontech (Mountain View, Calif., USA). The beads were removed from the column and, the beads were equilibrated with 1× Equilibration/Wash buffer pH 7.0 (50 mM Sodium Phosphate and 300 mM NaCl). The beads were incubated with the 1 liter cell culture supernatant overnight at 4° C. After the elution of FcγRIaECDHis (with 1× elution buffer (50 mM Sodium Phosphate, 300 mM NaCl and 150 mM Imidazole) at pH 5.0), the resin was re-equilibrated and added to the flow through of the earlier purification. After another overnight incubation, FcγRIaECDHis was again eluted. The eluted fractions of run 1 and run 2 were pooled and the pooled FcγRIaECDHis was desalted on a PD-10 column exchanging the buffer to PBS. The volume of the end product was 3.7 ml. The concentration was measured by determining the absorbance at 280 nm and was found to be 117 μg/ml yielding 433 μg FcγRIaECDHis (SEQ ID No:1). The end product was about 95% pure as judged by SDS-PAGE.

Example 4

Production of FcγRIIIaECD176VHis

Construction of pEE13.4FcγRIIIaECD176VHis

Plasmid DNA from RZPD clone IRAKp961H1749Q2 (Deutsche Ressourcenzentrum für Genomforschung (RZPD, Berlin, Germany)) was isolated and used as a template in a PCR with primers P5 (SEQ ID No:8) and P6 (SEQ ID No:9) according to the procedure described in example 1 amplifying the extracellular coding domain (aa 1-200) of human FcγRIIIa and introducing suitable restriction sites for cloning into pEE13.4, an ideal Kozak sequence (GCCGCCACC) and a C-terminal His$_6$-tag. The PCR fragment was gel purified and cloned into pEE13.4. For this, the PCR product was digested with EcoRI and XmaI and purified. The pEE13.4 vector was digested with EcoRI and XmaI and the vector fragment was purified. The FcγRIIIa fragment and the pEE13.4 EcoRI-XmaI vector were ligated and transformed into competent DH5α-T1$^R$ cells. Four colonies were checked by colony PCR (using primers P3 and P4) according to the procedure described in example 2, and two colonies contained an insert of the correct size. From the two positive colonies, 2 ml cultures were grown. Plasmid DNA was isolated and one of the constructs was checked by sequence analysis of the insert and found to be correct. The insert was the 176V allotype of FcγRIIIa. The final vector was named pEE13.4FcγRIIIaECD176VHis.

Transient Expression of FcγRIIIaECD176VHis in Hek-293F Cells

Freestyle™ 293-F (a HEK-293 subclone adapted to suspension growth and chemically defined Freestyle™ medium, e.g. HEK-293F) cells were obtained from Invitrogen and transfected with pEE13.4FcγRIIIaECD176VHis according to the manufacturer's protocol using 293Fectin™ (Invitrogen). The transfectants were cultured according to the manufacturer's protocol, and 200 ml of cell supernatant was used for purification as described below.

Purification of FcγRIIIaECD176VHis on BD TALONspin™ (0.5 ml) Talon Column

BD TALONspin™ columns were obtained from Clontech. The beads were removed from the column and equilibrated with 1× Equilibration/Wash buffer pH 7.0 (50 mM sodium phosphate and 300 mM NaCl), and incubated with 200 ml cell culture supernatant. The beads were washed with 1× Equilibration/Wash buffer to remove a specific bound proteins, and the His-tagged protein was eluted with 1× elution buffer (50 mM sodium phosphate, 300 mM NaCl and 150 mM Imidazole) at pH 5.0. After the elution of FcγRIIIaECD176VHis (with 1× elution buffer (50 mM Sodium Phosphate, 300 mM NaCl and 150 mM Imidazole) at pH 5.0), the resin was re-equilibrated and added to the flow through of the earlier purification. The eluted fractions of run 1 and run 2 were pooled. The pooled fractions were desalted on a PD-10 column to PBS. The yield of purified protein was determined by measuring the absorbance at 280 nm using the theoretic absorbance coefficient as calculated from the amino acid sequence of FcγRIIIaECD176VHis (SEQ ID No:2). Yield after purification was 2.5 mg per 200 ml in a concentration of 771 μg/ml. On SDS-PAGE, the protein migrated as one broad band (this indicates a heavily heterogeneously glycosylated protein) and two smaller bands of a higher MW. Purity was estimated to be about 90%.

Example 5

Production of FcγRIIIaECD176FHis

Mutagenesis of pEE13.4FcγRIIIaECD176VHis to Construct pEE13.4FcγRIIIaECD176FHis

Site directed mutagenesis was used to change the codon for Val176 of FcγRIIIa176V in the pEE13.4FcγRIIIaECD176VHis vector into Phe. A site-directed mutagenesis reaction was performed using the Quick-Change® II XL Site-Directed Mutagenesis Kit (Stratagene, Amsterdam, The Netherlands) according to the manufacturer's instructions. This method included the introduction of a silent extra Hpy188III site to screen for successful mutagenesis. Briefly, 5 μl 10× reaction buffer, 1.25 μl oligonucleotide P7 (100 ng/μl) (SEQ ID No:10), 1.25 μl oligonucleotide P8 (125 ng/μl) (SEQ ID No:11), 1 μl dNTP mix, 3 μl Quicksolution, 1 μl plasmid pEE13.4FcγRIIIaECD176VHis (50 ng/μl) and 1 μl PfuUltra HF DNA polymerase were mixed in a total volume of 50 μl and amplified with a TGradient Thermocycler 96 (Whatman Biometra, Goettingen, Germany; product#050-801) using an 18-cycle program: denaturing at 95° C. for 1 min; 18 cycles of 95° C. for 50 sec, 60° C. for 50 sec, and 68° C. for 10 min. PCR mixtures were stored at 4° C. until further processing. Next, PCR mixtures were incubated with 1 μl DpnI for 60 min at 37° C. to digest the vector and were stored at 4° C. until further processing. 2 μl of the reaction mixture was transformed into One Shot DH5α-T1$^R$ competent E. coli cells according to the manufacturer's instructions (Invitrogen).

Sixteen colonies were screened by colony PCR and Hpy188III digestion (a silent extra Hpy188III site was introduced during mutagenesis) and 15 out of 16 colonies appeared to contain the correct nucleotide changes. Two positive colonies were grown overnight, plasmid DNA was isolated and sequenced to confirm that the correct mutation was introduced. Both did contain the correct sequence and one was chosen for further propagation and named pEE13.4FcγRIIIaECD176FHis. To exclude introduction of additional mutations during the mutagenesis process, the whole FcγRIIIa coding region of pEE13.4FcγRIIIaECD176FHis was resequenced and no additional mutations were found. The final vector was named pEE13.4FcγRIIIaECD176FHis.

Transient Expression of FcγRIIIaECD176FHis in Hek-293F Cells

Freestyle™ 293-F (a HEK-293 subclone adapted to suspension growth and chemically defined Freestyle™ medium, e.g. HEK-293F) cells were obtained from Invitrogen and transfected with pEE13.4FcγRIIIaECD176FHis according to the manufacturer's protocol using 293Fectin™ (Invitrogen). The transfectants were cultured according to the manufacturer's protocol, and 200 ml of cell culture supernatant was used for purification as described below.

Purification of FcγRIIIaECD176FHis on BD TALONspin™ (0.5 ml) Talon Column

BD TALONspin™ columns were obtained from Clontech. The beads were removed from the column and equilibrated with 1× Equilibration/Wash buffer pH7.0 (50 mM sodium phosphate and 300 mM NaCl) and incubated with the 200 ml cell culture supernatant. The beads were washed with 1× Equilibration/Wash buffer to remove a specific bound proteins and the His-tagged protein was eluted with 1× elution buffer (50 mM sodium phosphate, 300 mM NaCl and 150 mM Imidazole) at pH 5.0. After the elution of FcγRIIIaECD176VHis (with 1× elution buffer), the resin was re-equilibrated and added to the flow through of the earlier purification. The pooled fractions were desalted on a PD-10 column to PBS. The yield of purified protein was determined by measuring the absorbance at 280 nm using the theoretic absorbance coefficient as calculated from the amino acid sequence of FcγRIIIaECD176FHis (SEQ ID No:3). Yield after purification was 1.5 mg per 200 ml, resulting in a concentration of 613 µg/ml. On SDS-PAGE, one broad band was seen, indicating a single, pure, glycosylated protein.

Example 6

Glycosylation Levels of Different Zanolimumab Batches

Level of Heavy Chain Glycosylation

To study the presence of N-linked glycosylation groups in the $CH_2$ domain of the heavy chain, several batches of zanolimumab (MEV001, MEV004, MEV005, MRS-CD4-001, BN078, BO118) with potential differences in heavy chain glycosylation were analyzed by SDS-PAGE and High pH Anion Exchange-Pulsed Amperometric Detection (HPAEC-PAD;). For comparison, control batches were prepared: de-glycosylated zanolimumab batch UNG-MRS-CD4, sham-deglycosylated batch MOCK-MRS-CD4 (directly derived from MRS-CD4-001), and mixed batches (mix of de-glycosylated and fully glycosylated reference batch) M90-MRS-CD4 [90% of heavy chains glycosylated] and M50-MRS-CD4 [50% of heavy chains glycosylated]).

Figure 2:
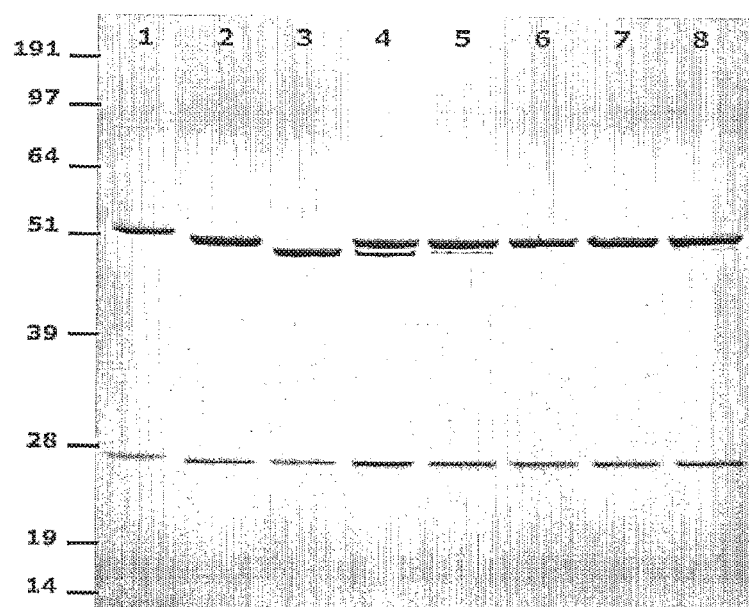
FIG. 2: Reduced SDS-PAGE of zanolimumab batches. MEV001, MEV004, MEV005, MRS-CD4-001, BN078 and BO118 are zanolimumab batches with differences in heavy chain glycosylation. UNG-MRS-CD4 is de-glycosylated zanolimumab batch, MOCK-MRS-CD4 is a sham-deglycosylated batch, and M90-MRS-CD4 and M50-MRS-CD4 are mixed batches (mix of de-glycosylated and fully glycosylated reference batch) with 90% of heavy chains glycosylated and 50% of heavy chains glycosylated, respectively.

All batches, including UNG-MRS-CD4 appeared intact as determined by non-reduced SDS-PAGE (FIG. 1). Batch UNG-MRS-CD4 was confirmed to be completely deglycosylated, as determined by reduced SDS-PAGE (FIG. 2).

Batches MRS-CD4-001 and BN078 contained low amounts of unglycosylated heavy chain (<10%), batch BO118 contained about 10% unglycosylated heavy chain. MEV001 also contained a low amount of unglycosylated heavy chains. Batches MEV004 and MEV005 contained unglycosylated heavy chains with MEV004 containing the highest amount (about 30%), followed by MEV005 (about 15%).

Type of Heavy Chain Glycosylation

To study the type of heavy chain glycosylation, the zanolimumab batches were analyzed by HPAEC-PAD (Table 1). None of the batches contained significant amounts of charged glycans. Complex type glycans with two galactoses (G2 or G2F) were almost undetectable.

MRS-CD4-001 (which was set as reference batch) and batch MEV005 contained a similar amount of oligomannose-5 type glycans (M5), but MEV005 contained less non core-fucosylated glycans compared to MRS-CD4-001. Batch MEV005 also contained the highest percentage of core-fucosylated glycans without galactose (G0F) of all batches, approximately 20% more than reference batch MRS-CD4-001.

Batch BN078 was comparable to reference batch MRS-CD4-001, with similar amounts of G0F, core-fucosylated glycans with one galactose (G1F) and non core-fucosylated glycans, although batch BN078 contained more M5. Batch BO118 was characterized by an increased amount of G0F and a decreased amount of non core-fucosylated glycans compared to MRS-CD4-001.

MRS-CD4-001 and MOCK-MRS-CD4 were highly comparable, as expected (MOCK-MRS-CD4 is directly derived from the reference batch MRS-CD4-001). Batch UNG-MRS-CD4 was confirmed to contain no glycans (data not shown).

TABLE 1

Overview of glycan profiles of zanolimumab batches determined by HPAEC-PAD.

| Zanolimumab batch | A | B | C | D | E |
|---|---|---|---|---|---|
| MRS-CD4-001 | >99% | 46.3 | 22.2 | 5.7 | 14.0 |
| MEV001 | Nt | Nt | Nt | Nt | Nt |
| MEV005 | >99% | 65.0 | 16.3 | 5.8 | 8.7 |
| BN078 | >99% | 43.7 | 20.2 | 8.1 | 16.6 |
| BO118 | >99% | 56.0 | 18.9 | 4.8 | 11.0 |
| UNG-MRS-CD4 | Ns | Ns | Ns | Ns | Ns |
| MOCK-MRS-CD4 | >99% | 44.5 | 21.2 | 5.8 | 15.4 |
| M50-MRS-CD4 | Nt | Nt | Nt | Nt | Nt |
| M90-MRS-CD4 | Nt | Nt | Nt | Nt | Nt |

A: Percentage neutral glycans
B: Percentage core-fucosylated glycans without galactose (G0F; percentage of total peak area)
C: Percentage core-fucosylated glycans with one galactose (G1F; percentage of total peak area)
D: Percentage oligo-mannose type 5 structure (M5, percentage of total peak area)
E: Percentage non core-fucosylated glycans (percentage of total peak area). Non core-fucosylated glycans were calculated according to formula: G0/[G0 + G0F'])*100 in which G0 is the percentage of non core-fucosylated glycans, and G0F' is the percentage of core-fucosylated glycans after β-galactosidase treatment (G0F + G1F)
Ns not shown
Nt not tested Example 7

Correlation of Glycosylation Differences with ADCC Activity I

Figure 3:
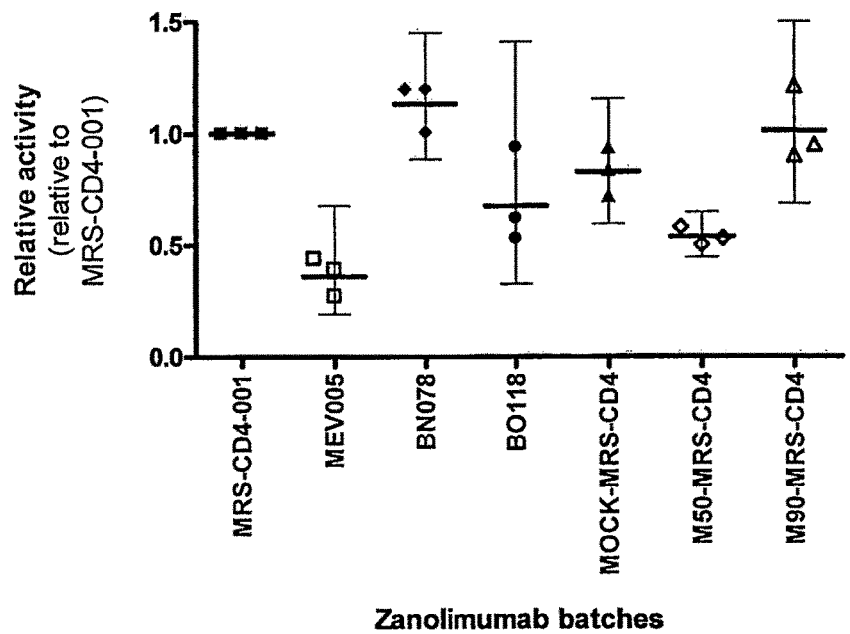
FIG. 3: Ability of zanolimumab batches to induce ADCC. The relative activity (derived from $EC_{50}$ values of bottom-fixed curves) of the batches relative to reference batch MRS-CD4-001 and geometric means with 95% confidence intervals are shown.

The ability of the several zanolimumab batches (see example 6) to induce NK-cell-mediated ADCC of primary CD4+ T cells was studied by flow cytometry (FIG. 3).

Peripheral human blood was collected from healthy volunteers (after informed consent) by vena puncture and provided in the form of a buffy coat (Sanquin, Utrecht, The Netherlands). Sterile PBS was added to the human blood, and peripheral blood mononuclear cells (PBMC) separated by lymphoprep density centrifugation (Lymphocyte Separation Medium; BioWhittaker, via Cambrex Verviers, Belgium; product#17-829E) at 800×g for 20 min (brake 0) for 20 minutes. PBMC at the gradient interface were removed and washed 3 times in PBS (400×g for 7 min, brake 3) before resuspension in RPMI. CD4+ T cells were isolated by negative selection using Dynal® CD4+ T-Cell Negative Isolation Kit (Dynal Biotech GmbH, Hamburg, Germany; product#113.11) according to the manufacturer's protocol. NK-cells were isolated by negative selection using Dynal® CD4+ T-Cell Negative Isolation Kit (Dynal Biotech GmbH, Hamburg, Germany; product#113.15) according to the manufacturer's protocol. The isolated CD4+ T-cells were labeled with the fluorescent cell membrane label PKH26 (PKH26 labeling kit, Sigma-Aldrich Chemie, Zwijndrecht, The Netherlands; product# PKH26-GL) according to manufacturer's protocol. PKH26-labeled CD4+ T-cells were then transferred to 96-well round-bottom plates at $2.5\text{-}5*10^4$ cells/well in 50 µl (depending on the NK-cell yield after isolation, the amount of T cells per well was adjusted to obtain a 10:1 effector cell:target cell ratio). Next, the diluted zanolimumab batches (dilution ranges in graphs indicated) were added in 50 µl and incubated at 4° C. for 10 min. Subsequently, 100 µl NK cells was added at $2.5\text{-}5*10^5$ cells/well, and cells were spun down, after which the pelleted cells were incubated at 37° C. for 4 hr. For spontaneous lysis, target cells were incubated with culture medium in the absence of NK cells. Next, cells were stained with TO-PRO®-3 (stains permeable cells; Molecular Probes, Leiden, The Netherlands; product# T3605; 1:100,000 final dilution) just before analysis. Cell-associated fluorescence was assessed by flow cytometry using a FACSCalibur™ and CellQuest™ Pro software (Becton Dickinson) with appropriate compensation settings. The percentage lysis of cells was calculated by dividing the number of TO-PRO®-3+ cells within the PKH26+ cell population by the total number of PKH26+ cells.

As four parameter logistic analysis allowing variable top levels showed that not all curves reached a similar top level, activity and relative activity of batches was calculated (instead of potency) using the $EC_{50}$ values of bottom-fixed curves.

Batches BN078, BO118, MOCK-MRS-CD4 and M90-MRS-CD4 appeared comparable to MRS-CD4-001 (which was used as the reference batch) regarding their ADCC-inducing activity. Batches MEV005, M50-MRS-CD4 appeared to induce NK cell-mediated ADCC with a lesser efficiency than reference batch MRS-CD4-001.

When studying the results with the reference and control batches, a clear correlation appeared to exist between the level of glycosylated heavy chains and the ability to induce ADCC. The fully glycosylated reference batch showed maximum ADCC activity, whereas batch M50-MRS-CD4 (containing 50% non-glycosylated zanolimumab) showed a much reduced activity in ADCC induction. Batch M90-MRS-CD4 (containing 10% non-glycosylated zanolimumab) had a similar ability to induce ADCC as the reference.

The results with test batches fit into this, in that batches MEV005 and BO118 that contain a certain amount of unglycosylated heavy chains showed a reduced ability to induce ADCC.

The analysis of batches MEV005 and BO118 showed that these batches possess also an increased level of fucosylation, which may suggest that fucosylation contributes to the reduced ability of these batches to induce ADCC (Shields, R. L. et al., J Biol Chem 277, 26733 (2002), and Okazaki, A. et al., J Mol Biol 336, 1239 (2004)).

Example 8

Correlation of Glycosylation Differences with ADCC Activity II

Figure 4A:
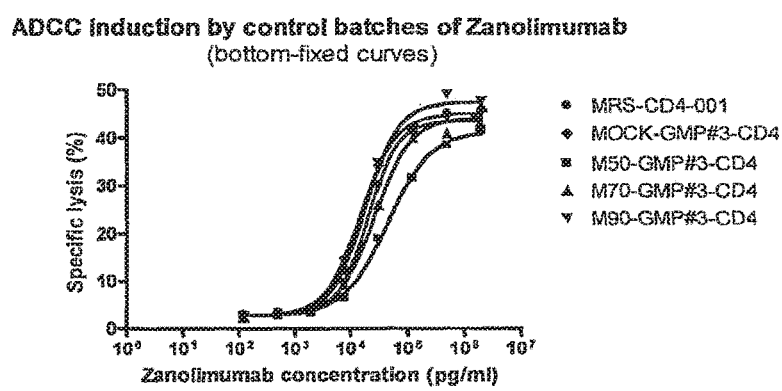
FIGS. 4A and 4B: Ability of de-glycosylated mix batches to induce ADCC. Reference batch MRS-CD4-001, MOCK-MRS-CD4, a sham-de-glycosylated batch, and mixed batches (mix of de-glycosylated and glycosylated GMP#3 batch) M50-GMP#3-CD4 (50% deglycosylated GMP#3), M70-GMP#3-CD4 (30% deglycosylated GMP#3), and M90-GMP#3 (10% deglycosylated GMP#3). The results of one representative of 3 experiments (see also data Table 2) are shown as the specific lysis of CD4+ T cells in the presence of a concentration range of the (partly) de-glycosylated batches (single data points).
Figure 4B:
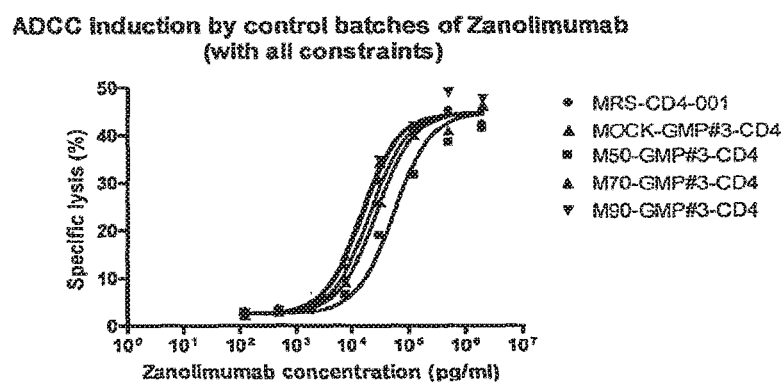

The ability of several de-glycosylated mix batches to induce NK-mediated ADCC of primary CD4+ T cells was studied by flow cytometry (see example 7). The results of one representative of 3 experiments (see data FIG. 4) are shown as the specific lysis of CD4+ T cells in the presence of a concentration range of the (partly) de-glycosylated batches (single data points). The curve fitting was performed using 4 parameter logistic fitting, with the bottom fixed to a common value (FIG. 4A). Furthermore, the curve fitting was performed using 4 parameter logistic fitting with constraints on bottom level, top level, and hill slope (FIG. 4B). Using the $EC_{50}$ values of top, bottom, and hill slope-fixed curves, the relative potencies to MRS-CD4-001 were calculated. Furthermore, the relative potencies relative to the parent GMP#3 batch (batch used for preparing de-glycosylated batches and mix batches) were calculated (Table 2). Compared to the MRS-CD4-001 batch, the GMP#3 batch and MOCK-GMP#3-CD4, a sham-de-glycosylated GMP#3 batch has a slightly increased ADCC activity. The M50-GMP#3-CD4, M70-GMP#3-CD4, and M90-GMP#3 mixed batches (mix of de-glycosylated and glycosylated GMP#3 batch), containing 50%, 30%, and 10% de-glycosylated GMP#3 respectively, have relative potencies to GMP#3 of 0.31, 0.59, and 0.87, showing a decreased ADCC activity with decreasing amounts of glycosylated heavy chains. In conclusion, a clear correlation appeared to exist between the level of glycosylated heavy chains and the ability to induce ADCC.

TABLE 2

Ability of de-glycosylated mix batches to induce ADCC

| Zanolimumab batch | Relative potency (ADCC) | | | |
|---|---|---|---|---|
| | Exp 1 | Exp 2 | Exp | Mean ± SD |
| MRS-CD4-001/GMP#1 | 1.00 | 1.00 | 1.00 | 1.00 |
| GMP#3 | 0.98 | 1.30 | 1.45 | 1.24 ± 0.24 (1.00)* |
| MOCK-GMP#3-CD4 | 1.38 | 1.55 | 1.42 | 1.45 ± 0.09 (1.17)* |
| M50-GMP#3-CD4 | 0.14 | 0.64 | 0.39 | 0.39 ± 0.25 (0.31)* |
| M70-GMP#3-CD4 | 0.37 | 1.03 | 0.79 | 0.73 ± 0.33 (0.59)* |
| M90-GMP#3-CD4 | 0.74 | 1.18 | 1.33 | 1.08 ± 0.31 (0.87)* |

*potency relative to batch GMP#3, from which these test batches were derived

The relative potencies (derived from $EC_{50}$ values of curves with constraints set on bottom level, top level, and hill slope) relative to reference batch MRS-CD4-001 and means with SD (stand deviation) are shown. Within brackets the relative potencies related to the parent batch GMP#3 is given.

Example 9

FcγRIIIa176V Binding ELISA and Correlation with ADCC I

Several batches of zanolimumab (see example 6) were tested for binding to FcγRIIIa176V.

Figure 5:
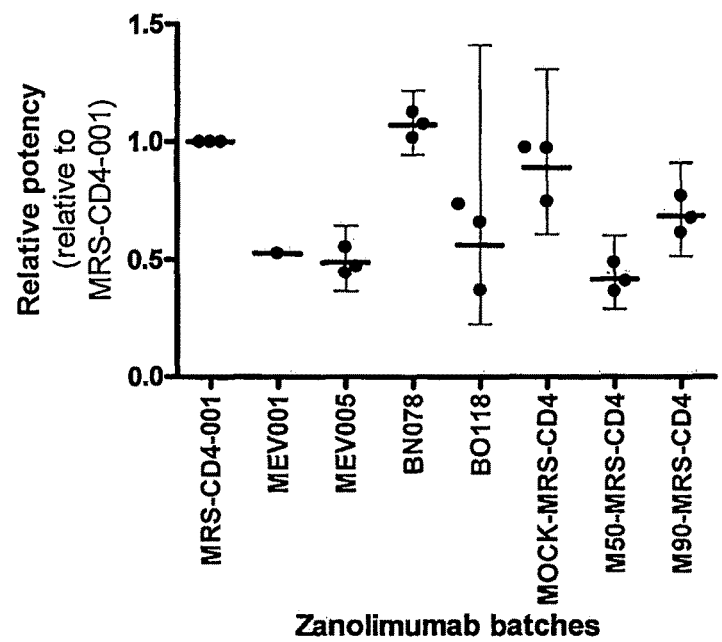
FIG. 5: Binding of zanolimumab batches to plate-bound FcγRIIIaECD176VHis. The relative potencies relative to reference batch MRS-CD4-001 and geometric means with 95% confidence intervals are shown. MEV001, MEV005, BN078 and BO118 are zanolimumab batches with differences in heavy chain glycosylation. MOCK-MRS-CD4 is a sham-deglycosylated batch, and M90-MRS-CD4 and M50-MRS-CD4 are mixed batches (mix of de-glycosylated and fully glycosylated reference batch) with 90% of heavy chains glycosylated and 50% of heavy chains glycosylated, respectively.

A Greiner plate was coated with 100 µl of 2.5 µg/ml FcγRIIIa176V (prepared as described in example 4) and incubated overnight at 4° C. Plates were washed 3 times with 200 µl PBST (PBS containing 0.05% Tween-20 (Sigma-Aldrich Chemie B.V., Zwijndrecht, NL; cat 63158)) and 100 µl of serial diluted zanolimumab samples (concentrations of zanolimumab of 300, 75, 18.75, 4.69, 0.29, 1.17, 0.07, and 0.02 µg/ml). The plates were incubated 60 min at RT, under shaking conditions and were then washed 3 times with 200 µl PBST followed by addition of conjugate 1:4000 diluted peroxidase-conjugated affinipure F(ab')$_2$ Fragment G-a-Hu-IgG, F(ab')$_2$ Fragment specific ((Jackson ImmunoResearch, Brunschwig Chemie B.V., Amsterdam, The Netherlands). The plates were again incubated 60 min at RT under shaking conditions and then washed 3 times with 200 µl PBST. 100 µl ABTS (Roche, cat nr 1112597) was added and the plates were incubated 30 min under shaking conditions. The reaction was stopped with addition of 100 µl 2% oxalic acid and the absorbance at 405 nm was measured. The results are shown in FIG. 5.

As four parameter logistic analysis allowing variable top levels showed that all curves reached a similar top level, potency and relative potency of batches was calculated using the $EC_{50}$ values of curves with fixed bottom levels, top levels and hill slopes.

Batches BN078 and MOCK-MRS-CD4 bound similarly to plate-bound FcγRIIIa176V as reference batch MRS-CD4-001. Batches MEV001, MEV005, BO118, M50-MRS-CD4 and M90-MRS-CD4 appeared to have a lower potency to bind to plate-bound FcγRIIIa176V. Batches MEV001, MEV005, BO118 and M50-MRS-CD4 were comparable regarding binding to plate-bound FcγRIIIa176V, with relative potencies of 0.4-0.5. M90-MRS-CD4 behaved differently than expected, and binds with relative potency of about 0.7 (expected was 0.9).

A clear correlation appeared to exist between the level of glycosylated heavy chains and the ability to bind FcγRIIIa176V from studies with the reference and control batches. The fully glycosylated reference batch showed maximum FcγRIIIa176V binding, whereas batch M50-MRS-CD4 showed a much reduced binding and batch M90-MRS-CD4 showed intermediate binding.

The results with test batches fit into this, in that batches MEV005 and BO118, containing 30% and 10% of unglycosylated heavy chains, showed a much reduced FcγRIIIa176V binding. Unexpected was the finding that batch MEV001 also showed a much reduced FcγIIIa176V binding, although this batch did not appear to contain unglycosylated heavy chains as detected by SDS-PAGE.

Overall can be concluded that a correlation exists between the induction of ADCC (FIG. 3) and the binding to purified FcγRIIIa176V (FIG. 5).

Example 10

FcγRIIIa176V Binding ELISA and Correlation with ADCC II

The ability of several de-glycosylated mix batches of zanolimumab (see example 8) to bind to FcγRIIIa176V was tested.

A Greiner plate was coated with 100 µl of 2.5 µg/ml FcγRIIIa176V (prepared as described in example 4) and incubated overnight at 4° C. Plates were washed 3 times with 200 µl PBST and 100 µl of serial diluted zanolimumab samples (concentrations of zanolimumab of 300, 75, 18.75, 4.69, 0.29, 1.17, 0.07, and 0.02 µg/ml). The plates were incubated 60 min at RT, under shaking conditions and were then washed 3 times with 200 µl PBST followed by addition of conjugate 1:4000 diluted peroxidase-conjugated affinipure F(ab')$_2$ Fragment G-a-Hu-IgG, F(ab')$_2$ Fragment specific (Jackson ImmunoResearch, Brunschwig Chemie B.V., Amsterdam, The Netherlands). The plates were again incubated 60 min at RT under shaking conditions and then washed 3 times with 200 µl PBST. 100 µl ABTS (Roche, cat nr 1112597) was added and the plates were incubated 30 min under shaking conditions. The reaction was stopped with addition of 100 µl 2% oxalic acid and the absorbance at 405 nm was measured. The results are shown in FIG. 6.

Figure 6:
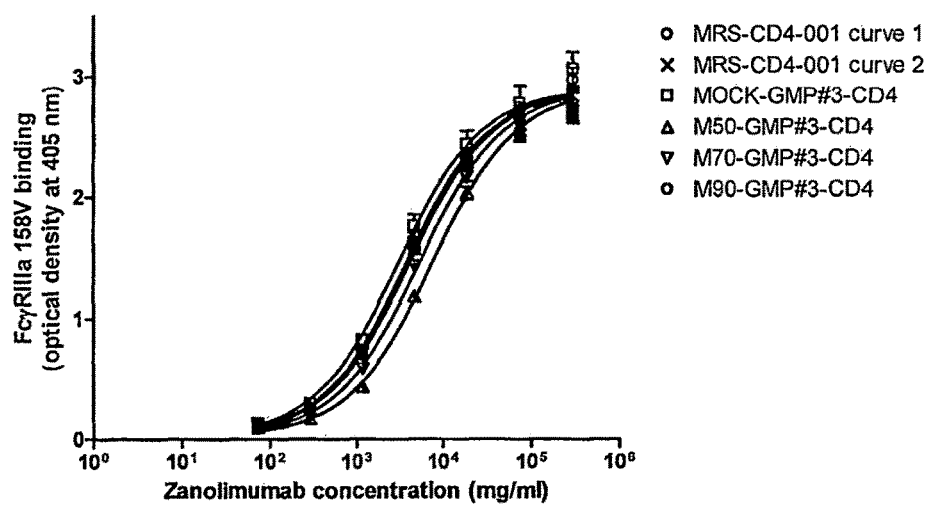
FIG. 6: Binding of de-glycosylated mix batches of zanolimumab to plate-bound FcγRIIIaECD176VHis. Reference batch MRS-CD4-001, MOCK-MRS-CD4 is a sham-deglycosylated batch, M50-GMP#3-CD4, M70-GMP#3-CD4, and M90-GMP#3 are mixed batches (mix of de-glycosylated and glycosylated GMP#3 batch). The results of one representative of 2 experiments (see also data Table 3) are shown as the binding to FcγRIIIa176V in the presence of a concentration range of the (partly) de-glycosylated batches (triplicate data points). The curve fitting was performed using 4 parameter logistic fitting with constraints on bottom level, top level, and hill slope. GMP#3 is the patent batch.

The curve fitting was performed using 4 parameter logistic fitting, with constraints on bottom level, top level, and hill slope (FIG. 6). Using the $EC_{50}$ values of top, bottom, and hill slope-fixed curves, the relative potencies to MRS-CD4-001 were calculated. Furthermore, the relative potencies relative to the parent GMP#3 batch (batch used for preparing de-glycosylated batches and mix batches) were calculated (Table 3).

TABLE 3

Binding of zanolimumab batches to plate-bound FcγRIIIa176V

| Zanolimumab batch | Relative potency (FcγRIIIa176V binding) | | |
|---|---|---|---|
| | Exp 1 | Exp 2 | Mean ± SD |
| MRS-CD4-001/GMP#1 | 1.00 | 1.00 | 1.00 |
| GMP#3 | 1.12 | 1.12 | 1.12 ± 0.00 (1.00)* |
| UNG-GMP#3-CD4 | Nd | Nd | — |
| MOCK-GMP#3-CD4 | 1.23 | 1.23 | 1.23 ± 0.00 (1.09)* |
| M50-GMP#3-CD4 | 0.50 | 0.60 | 0.55 ± 0.07 (0.49)* |
| M70-GMP#3-CD4 | 0.71 | 0.88 | 0.80 ± 0.12 (0.71)* |
| M90-GMP#3-CD4 | 0.91 | 1.16 | 1.04 ± 0.18 (0.93)* |

The relative potencies (derived from $EC_{50}$ values of curves with constraints set on bottom level, top level, and hill slope) relative to reference batch MRS-CD4-001 and means with SD are shown. Within brackets the relative potencies related to the parent batch GMP#3 is given.

Figure 7:
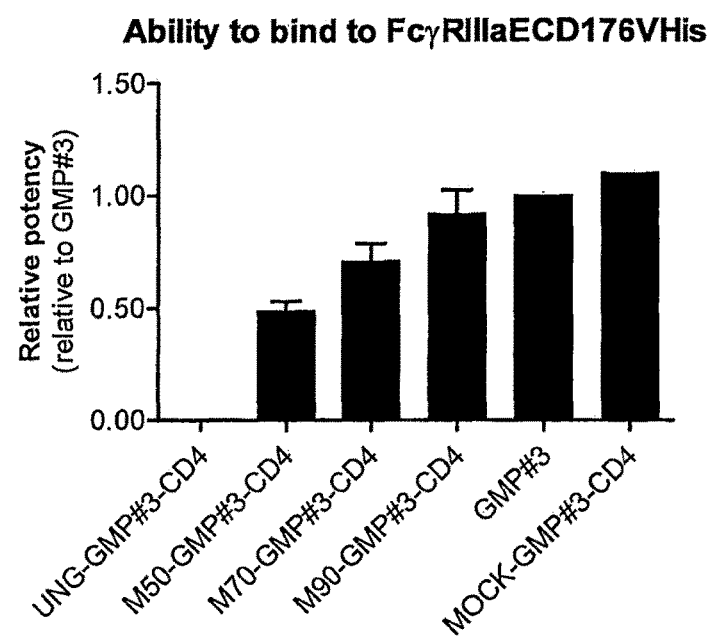
FIG. 7: Relation between heavy chain glycosylation of Zanolimumab batches and ability to bind to FcγRIIIaECD176VHis. Batches described in FIG. 6 and Table 3 were ranked (left to right) according to their content of glycosylated heavy chains. Results are shown as the relative potency to bind to FcγRIIIaECD176VHis relative to parent batch GMP#3 (mean±SD of n=2 experiments).

Compared to the MRS-CD4-001 batch, the GMP#3 batch and MOCK-GMP#3-CD4, a sham-de-glycosylated GMP#3 batch has a slightly increased FcγRIIIa176V binding. The M50-GMP#3-CD4, M70-GMP#3-CD4, and M90-GMP#3 mixed batches (mix of de-glycosylated and glycosylated GMP#3 batch), containing 50%, 30%, and 10% de-glycosylated GMP#3 respectively, have relative potencies to GMP#3 of 0.49, 0.71, and 0.93, showing a decreased FcγRIIIa176V binding with decreasing amounts of glycosylated heavy chains. In conclusion, a clear correlation appeared to exist between the level of glycosylated heavy chains and the ability to bind to FcγRIIIa176V (FIG. 7).

Figure 8:
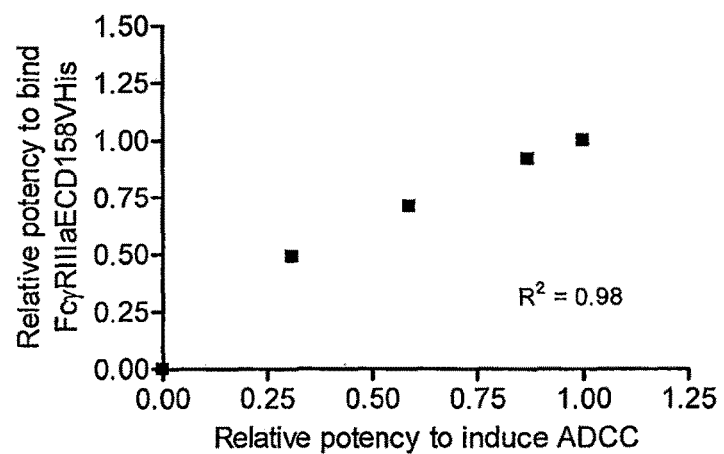
FIG. 8: Correlation between ability of zanolimumab batches to induce ADCC and to bind FcγRIIIaECD176VHis. The relative potency of the zanolimumab batches to induce ADCC described in Table 2, and the relative potency of zanolimumab batches to bind FcγRIIIaECD176VHis described in FIG. 6 and Table 3 were plotted on the x-axis and y-axis (potency relative to parent batch GMP#3). The correlation coefficient is indicated in the plot.

Again, a clear correlation between the ADCC and the FcγRIIIa176V binding does exist (FIG. 8).

Example 11

Binding to Antigen I

Figure 9:
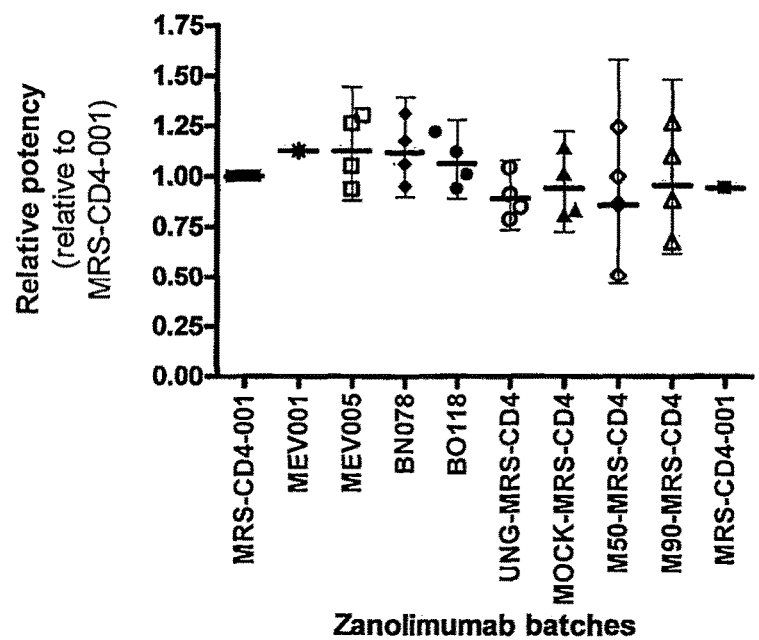
FIG. 9: Binding of zanolimumab batches to plate-bound CD4. The relative potency relative to reference batch MRS-CD4-001 and geometric means with 95% confidence intervals are shown. MEV001, MEV005, BN078 and BO118 are zanolimumab batches with differences in heavy chain glycosylation. UNG-MRS-CD4 is unglycosylated zanolimumab batch, MOCK-MRS-CD4 is a sham-deglycosylated batch, and M90-MRS-CD4 and M50-MRS-CD4 are mixed batches (mix of de-glycosylated and fully glycosylated reference batch) with 90% of heavy chains glycosylated and 50% of heavy chains glycosylated, respectively.

The binding of zanolimumab batches to purified CD4 protein was studied by ELISA (FIG. 9). sCD4 (Immuno Diagnostics, Woburn, Mass., USA, cat nr 7001-10) was coated to flat-bottom 96-well plates (Greiner, Alphen a/d Rijn, NL, cat nr 655092) at 0.5 µg/ml (100 µl/well) in PBS by incubation at 4° C. overnight. Plates were emptied and residual non-specific binding sites were blocked with 200 µl/well PBSC (PBS containing 2% (v/v) chicken serum (Invitrogen, Breda, NL, cat nr 16110-082)) for at RT 1 hour on a shaker. Dilutions of the zanolimumab batches were prepared, ranging from 2000 ng/ml to 0.49 ng/ml, by serial 4-fold dilution in PBSTC (PBS containing 0.05% (v/v) Tween-20 (Sigma-Aldrich Chemie B.V., Zwijndrecht, NL; cat 63158) and 2% (v/v) chicken serum). After emptying the plates, 100 µl of the dilutions were added to the coated plates, and incubate at RT for 2 hours on a shaker. Plates were emptied and washed 3 times with PBST 1× (200 µl/well). The conjugate, goat-anti-HuIgG F(ab')$_2$ spec-HRP (Jackson ImmunoResearch), was diluted 1:10.000 in PBSTC 1× and added at 100 µl per well. The plates were incubated at RT for 1 hour on a shaker. Plates were emptied and washed 3 times with PBST 1× (200 µl/well). Plates were tapped over absorbent paper to remove all residual fluid. One tablet of ABTS substrate (50 mg Roche Diagnostics NL, Almere, NL, cat nr 1122422) was dissolved in 50 ml ABTS buffer (Roche, cat nr 1112597) and 100 µl was added per well. Plates were wrapped in aluminum foil and incubated at RT for 30 minutes on a shaker. The reaction was stopped with 100 µl/well 2% oxalic acid (Sigma-Aldrich Chemie B.V.). The absorbance was read at 405 nm on a spectrophotometer (ELISA-EL808, Beun de Ronde, Abcoude, NL).

As four parameter logistic analysis allowing variable top levels showed that all curves reached a similar top level, potency and relative potency of batches was calculated using the $EC_{60}$ values of curves with fixed bottom levels, top levels and hill slopes.

Compared to reference batch MRS-CD4-001, all other batches bound similarly to plate-bound sCD4, despite clear differences in glycosylation of the batches. It should be noted that the variation in this assay was relatively high.

Example 12

Binding to Antigen II

Figure 10:
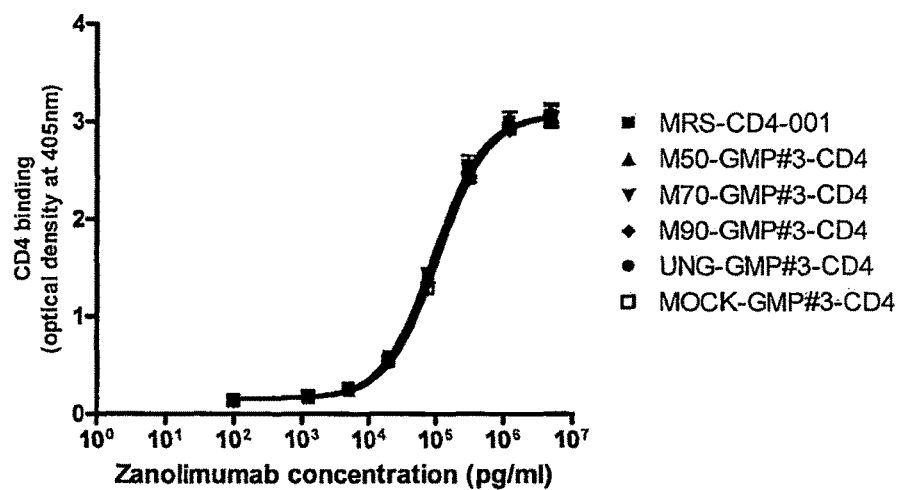
FIG. 10: Binding of de-glycosylated mix batches of zanolimumab to plate-bound CD4. Reference batch MRS-CD4-001, MOCK-MRS-CD4, a sham-de-glycosylated batch, and mixed batches (mix of de-glycosylated and glycosylated GMP#3 batch) M50-GMP#3-CD4 (50% deglycosylated GMP#3), M70-GMP#3-CD4 (30% deglycosylated GMP#3), and M90-GMP#3 (10% deglycosylated GMP#3). The results of one representative of 2 experiments (see also data Table 4) are shown as the binding to CD4 in the presence of a concentration range of the (partly) de-glycosylated batches (triplicate data points). The curve fitting was performed using 4 parameter logistic fitting with constraints on bottom level, top level, and hill slope. GMP#3 is the patent batch.

The binding of zanolimumab mixed batches (see example 8) to purified CD4 protein was studied by ELISA (FIG. 10).

A Greiner plate was coated with 100 µl of 2.0 µg/ml sCD4 (Immuno Diagnostics, Woburn, Mass., USA, product#7001-10) and incubated overnight at 4° C. Plates were washed 3 times with 200 µl PBST and 100 µl of serial diluted zanolimumab samples (concentrations of zanolimumab of 1000, 250, 62.5, 15.62, 3.9, 0.98, 0.24, and 0.06 ng/ml). The plates were incubated 60 min at RT, under shaking conditions and were then washed 3 times with 200 µl PBST followed by addition of conjugate 1:20000 diluted peroxidase-conjugated affinipure G-a-Hu-IgG, F(ab')$_2$ Fragment specific (Jackson ImmunoResearch, Brunschwig Chemie B.V., Amsterdam, The Netherlands). The plates were again incubated 60 min at RT under shaking conditions and then washed 3 times with 200 µl PBST. 100 µl ABTS (Roche, cat nr 1112597) was added and the plates were incubated 30 min under shaking conditions. The reaction was stopped with addition of 100 µl 2% oxalic acid and the absorbance at 405 nm was measured.

As four parameter logistic analysis allowing variable top levels showed that all curves reached a similar top level, potency and relative potency of batches was calculated using the EC50 values of curves with fixed bottom levels, top levels and hill slopes (Table 4).

TABLE 4

Binding of de-glycosylated mix batches of zanolimumab to plate-bound CD4

| Zanolimumab batch | Relative potency (sCD4 binding) | | |
|---|---|---|---|
| | Exp 1 | Exp 2 | Mean ± SD |
| MRS-CD4-001/GMP#1 | 1.00 | 1.00 | 1.00 |
| GMP#3 | 0.91 | 0.92 | 0.92 ± 0.01 |
| UNG-GMP#3-CD4 | 0.96 | 1.01 | 0.99 ± 0.04 |
| MOCK-GMP#3-CD4 | 0.98 | 0.85 | 0.92 ± 0.09 |
| M50-GMP#3-CD4 | 1.03 | 0.90 | 0.97 ± 0.09 |
| M70-GMP#3-CD4 | 0.84 | 0.91 | 0.88 ± 0.05 |
| M90-GMP#3-CD4 | 0.94 | 0.94 | 0.94 ± 0.00 |

The relative potencies (derived from $EC_{50}$ values of curves with constraints set on bottom level, top level, and hill slope) relative to reference batch MRS-CD4-001 and means with SD are shown. GMP#3 is the patent batch Compared to reference batch MRS-CD4-001, all other batches bound similarly to plate-bound sCD4, despite clear differences in glycosylation of the batches.

Example 13

Inhibition of IL-2 Production

The ability of zanolimumab batches (see example 6) to inhibit the production of IL-2 by activated PBMC was studied by a nested assay (T-cell activation assay followed by IL-2 ELISA) using the Human IL-2 cytokine ELISA kit obtained from U-CyTech (Utrecht, The Netherlands; product# CT202) or from BD Biosciences (Alphen aan de Rijn, The Netherlands; product#550611) and following the manufacturer's instructions.

PBMC (105 cells per well) were stimulated in 96-well flat-bottom plates with plate-bound anti-CD3 (100 ng/ml) and soluble anti-CD28 (100 ng/ml) in the presence of a serial dilution (or selected series) of the antibody reference or test sample. Thirty-eight to forty-two hours later, cell-free supernatants were harvested, diluted in dilution buffer and transferred to 96-well ELISA plates. The IL-2 concentration was determined in pg/ml via ELISA using a human IL-2 ELISA kit including an IL-2 standard.

As four parameter logistic analysis allowing variable top levels showed that all curves reached a similar top level, potency and relative potency of batches was calculated using the $EC_{50}$ values of curves with fixed bottom levels, top levels and hill slopes; as the UNG-MRS-CD4 did not reach the same bottom level, this batch was excluded from this analysis. Relative potencies were calculated using the mean $EC_{50}$ of two MRS-CD4-001 curves. Calculations were performed for each individual plate.

Figure 11:
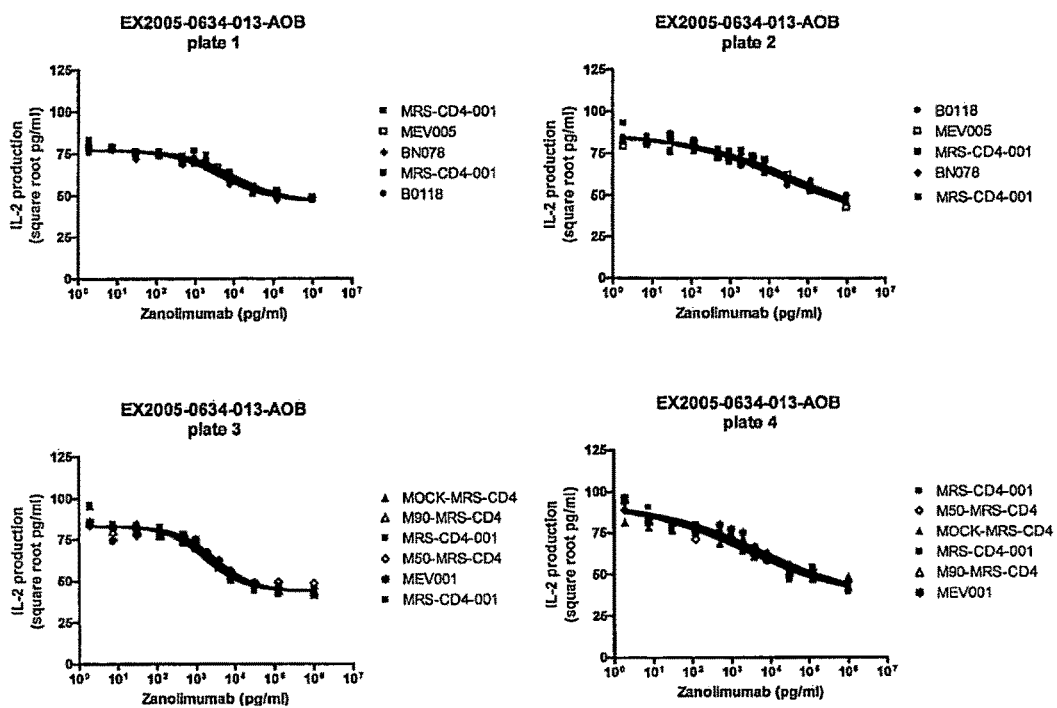
FIG. 11: Ability of zanolimumab to inhibit IL-2 production. MEV001, MEV005, MRS-CD4-001, BN078 and BO118 are zanolimumab batches with differences in heavy chain glycosylation. MOCK-MRS-CD4 is a sham-deglycosylated batch, and M90-MRS-CD4 and M50-MRS-CD4 are mixed batches (mix of de-glycosylated and fully glycosylated reference batch) with 90% of heavy chains glycosylated and 50% of heavy chains glycosylated, respectively.

The ability of zanolimumab batches to inhibit IL-2 production was tested as described above. Results are shown as the level of IL-2 in supernatant of duplicate samples. The whole panel of zanolimumab batches was tested using four plates and was tested twice per experiment. One of two experiments is shown (FIG. 11).

The ability of zanolimumab batches to inhibit IL-2 production was tested as described above. The relative activity (derived from $EC_{50}$ values of bottom-fixed curves) relative to reference batch MRS-CD4-001 (mean $EC_{50}$ of 2 MRS-CD4-001 curves) are shown of the two experiments (Table 5)

TABLE 5

Ability of zanolimumab to inhibit of IL-2 production.

| | | Relative activity to MRS-CD4-001 | | | | | | | | | |
|---|---|---|---|---|---|---|---|---|---|---|---|
| Experiment | Plate# | MRS-CD4-001 | MEV005 | BN078 | BO118 | UNG-MRS-CD4 | MOCK-MRS-CD4 | M90-MRS-CD4 | M50-MRS-CD4 | MEV001 | MRS-CD4-001 |
| EX2005-0634-013-AOB | plate 1 | 0.74 | 0.92 | 1.83 | 1.17 | nt | nt | nt | nt | nt | 1.54 |
| | plate 2 | 1.68 | 1.07 | 1.01 | 0.90 | nt | nt | nt | nt | nt | 0.71 |
| | plate 3 | 1.45 | nt | nt | nt | nt | 1.07 | 1.04 | 0.74 | 0.79 | 0.76 |
| | plate 4 | 0.87 | nt | nt | nt | nt | 1.42* | 0.76 | 0.77 | 0.51 | 1.18 |
| EX2005-0634-014-AOB | plate 1 | 1.57 | nt | nt | 1.82 | nt | nt | 3.17 | 1.47* | nt | 0.73 |
| | plate 2 | 1.03 | nt | nt | 1.69 | nt | nt | 1.10 | 0.55 | nt | 0.98 |
| | plate 3 | 1.10 | 0.84 | 0.69 | nt | nt | 0.94 | nt | nt | 0.35 | 0.92 |
| | plate 4 | 1.10 | 0.58 | 1.10 | nt | nt | 1.32 | nt | nt | 0.69 | 0.92 |
| Geometric mean relative activity | | 1.15 | 0.83 | 1.09 | 1.34 | | 1.10 | 1.29 | 0.68 | 0.56 | 0.94 |

All tested zanolimumab batches, except control batch UNG-MRS-CD4, inhibited IL-2 production. Batches MOCK-MRS-CD4, M90-MRS-CD4, BN078 and MEV005 inhibited in a similar manner as reference batch MRS-CD4-001. Batch BO118 inhibited to a higher extent, and batches M50-MRS-CD4 and MEV001 to a lesser extent. A high variability existed between and within experiments. When studying the results with the reference and control batches, the level of glycosylated heavy chains appeared to correlate to some extent to the ability to inhibit IL-2 production by activated T cells. The fully glycosylated reference batch showed maximum activity, whereas batch M50-MRS-CD4 showed a much reduced ability to inhibit IL-2 production. Batch M90-MRS-CD4 had a similar ability to inhibit IL-2 production as the reference.

Test batch MEV005, containing 30% of unglycosylated heavy chains, showed a reduced ability to inhibit IL-2 production. However, batch MEV001 that did not appear to contain unglycosylated heavy chains, also showed a reduced ability to inhibit IL-2 production, while batch BO118, containing 10% of unglycosylated heavy chains was very well able to inhibit IL-2 production, even to a slightly higher extent than the reference.

Example 14

Screening for FcR Binding and CD4 Binding of Several Zanolimumab Batches by an AlphaScreen™-Based Assay Several batches of zanolimumab (see example 8) were tested for binding to FcγRIIIa176V and to CD4 using a single AlphaScreen™-based assay.

His-tagged-FcγRIIIa176V was coupled to Ni-acceptor beads. Beads were washed to remove unbound His-tagged-FcγRIIIa176V. sCD4-biotine was coupled to SA-donor beads. Beads were washed to remove unbound sCD4-biotine. Dilution ranges of reference batch MRS-CD4-001 and H-IgG were prepared (range: 90, 30, 3, 1, 0.3, 0.03, and 0 µg/ml). A variable volume of His-tagged-FcγRIIIa176V-Ni-acceptor beads was brought into the wells of an 384-well optiplate, followed by addition of a fixed volume zanolimumab or H-IgG and a fixed volume of sCD4-biotine-SA-donor beads. After incubation at room temperature in the dark for 1 hour, the bead/antibody mixes were analyzed using the EnVision™ apparatus with the 'alphascreen label'.

Figure 12:
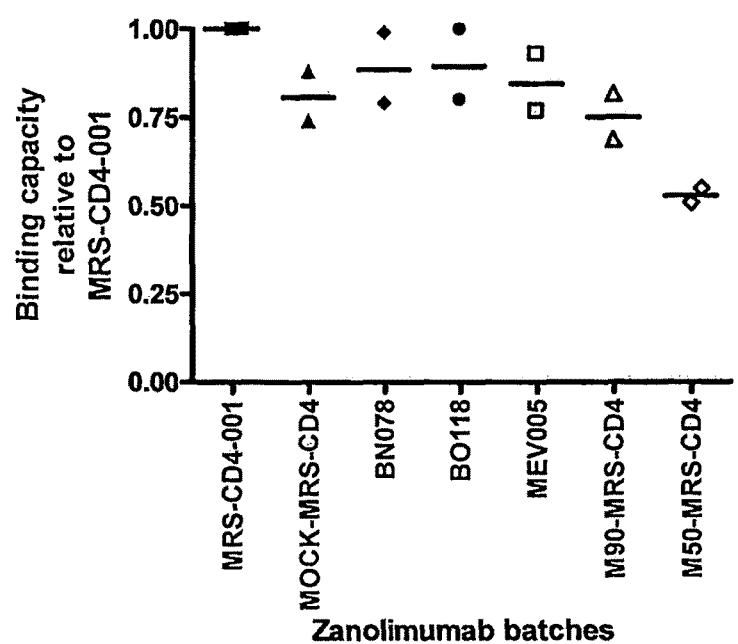
FIG. 12: Screening for FcγRIIIaECD176VHis binding and CD4 binding of several zanolimumab batches by an AlphaScreen™-based assay. The relative potency relative to reference batch MRS-CD4-001 and geometric means with 95% confidence intervals are shown. MEV005, BN078 and BO118 are zanolimumab batches with differences in heavy chain glycosylation. UNG-MRS-CD4 is de-glycosylated Zanolimumab batch, MOCK-MRS-CD4 is a sham-de-glycosylated batch, and M90-MRS-CD4 and M50-MRS-CD4 are mixed batches (mix of de-glycosylated and fully glycosylated reference batch) with 90% of heavy chains glycosylated and 50% of heavy chains glycosylated, respectively.

FIG. 12 confirms that the trend in relative binding capacity is similar for both experiments. The M50-MRS-CD4 batch showed a mean capacity of 53% of the reference batch, according to the expectation. The M90-MRS-CD4 batch showed a capacity of around 75%, which is somewhat lower than expected. Batches BO118 and BN078 showed a similar binding capacity (88% and 89%). Batches MEV005 and MOCK-MRS-CD4 had a slightly lower binding capacity (84% and 81%).

Example 15

Binding to Cell-Bound FcγRI

Several batches of zanolimumab (see example 8) were tested for binding to cell-bound FcγRI.

IIA1.6 and IIA1.6-FcγRI cells (kindly provided by Ms. L. Bevaart, (Dept. of Immunotherapy, University Medical Centre Utrecht, Utrecht, The Netherlands)) were harvested and counted by Trypan blue exclusion. Cells were spun down at RT at 500 g for 5 min, supernatant was discarded, and cells were resuspended in staining buffer (PBS containing 1% v/v BSA (Roche, Almere, NL) and 0.01% v/v azide (Sigma-Aldrich Chemie B.V.)) at $1 \times 10^6$ cells per ml and transferred to 96-well V-bottom plates at 100 µl/well (Greiner, Frickenhausen, Germany, cat #651101). Dilutions of the zanolimumab batches were prepared, ranging from 10000 ng/ml to 9.8 ng/ml, by serial 2-fold dilution in staining buffer. 100 µl of sample, a negative control IgG2 (Binding site, Birmingham, UK, cat #BP080), or staining buffer was added to the cells and incubated at 4° C. for 30 min. Cells were washed 3 times with 150 µl staining buffer per well, and spun down at RT at 500 g for 5 min. 100 µl per well of F(ab')$_2$-Gt-anti-Hu-IgG-F(ab')$_2$-FITC (Jackson, Pa., USA, cat#109-096-097; diluted 1:100 in staining buffer) was added to cell pellets, and incubated at 4° C. for 30 min. Cells were washed 3 times with 150 µl staining buffer, and spun down at RT at 500 g for 5 min. Cells were resuspended in 150 µl staining buffer and transferred to 1.3 ml tubes. Cells were analyzed using the FACSCalibur™ (BD) or FACScan™ (BD).

Figure 13:
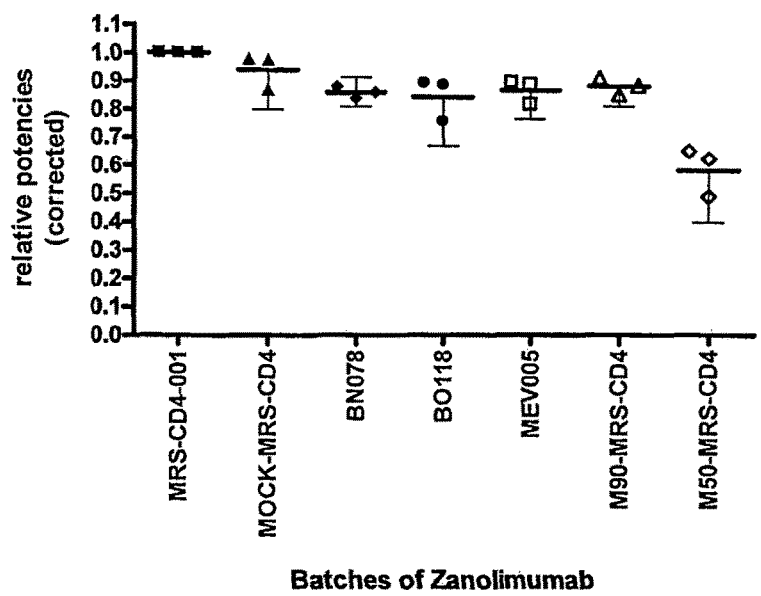
FIG. 13: Ability of zanolimumab to bind cell-bound FcγRI. The relative potency relative to reference batch MRS-CD4-001 and geometric means with 95% confidence intervals are shown. MEV005, BN078 and BO118 are zanolimumab batches with differences in heavy chain glycosylation. UNG-MRS-CD4 is de-glycosylated Zanolimumab batch, MOCK-MRS-CD4 is a sham-de-glycosylated batch, and M90-MRS-CD4 and M50-MRS-CD4 are mixed batches (mix of de-glycosylated and fully glycosylated reference batch) with 90% of heavy chains glycosylated and 50% of heavy chains glycosylated, respectively.

Compared to reference batch MRS-CD4-001, most batches bound to a slightly lower amount to cell-bound FcγRI, despite differences in glycosylation of the batches. It should be noted that the variation in this assay was relatively high. Still, batch M50-MRS-CD4, containing only 50% glycosylated heavy chains had a lower binding capacity. The batch UNG-MRS-CD4 did hardly bind to plate-bound FcγRI (FIG. 13).

Example 16

Binding to Plate-Bound FcγRI

Several batches of zanolimumab (see example 8) were tested for binding to plate-bound FcγRI.

His-tagged recombinant FcγRI (Genmab B.V., Utrecht, NL, batch #EX2005-0403-016-TVE) was coated to flat-bottom 96-well plates (Greiner, Alphen a/d Rijn, NL, cat nr 655092) at 1.5 μg/ml (100 μl) in PBS by incubation at 4° C. overnight. Plates were washed 3 times with PBS, emptied and residual non-specific binding sites were blocked with 200 μl/well PBSC at RT for 1 hour. Dilutions of zanolimumab batches were prepared, ranging from 4000 ng/ml to 31.25 ng/ml, by serially 2-fold dilutions in PBSTC. 100 μl diluted sample was added, and incubated at RT for 2 hours. Plates were emptied, and washed 3 times with PBST 1× (200 μl/well). The conjugate, goat [F(ab')₂ fragments]-anti-Hu-IgG F(ab')₂ spec-HRP (Jackson, cat nr 109-096-097) (in EX2005-0505-008-MVO the conjugate goat-anti-HuIgG F(ab')₂ spec-HRP Jackson cat nr 109-035-097 was used), was diluted 1:10.000 in PBSTC 1×, and 100 μl of conjugate was added per well. Plates were incubated at RT for 1 hour. Plates were emptied, and washed 3 times with PBST 1× (200 μl/well). Plates were tapped over absorbent paper to remove all residual fluid. A tablet of ABTS substrate (50 mg (Roche Diagnostics NL, Almere, NL, cat nr 1122422)) was dissolved in 50 ml ABTS buffer (Roche, cat nr 1112597) and 100 μl was added per well. Plates were wrapped in aluminum foil and incubated at RT for 30 minutes. The reaction was stopped with 100 μl/well 2% oxalic acid [Sigma-Aldrich Chemie B.V.]. The absorbance was read on a spectrophotometer [ELISA-EL808, Beun de Ronde, Abcoude, NL] at 405 nm.

Figure 14:
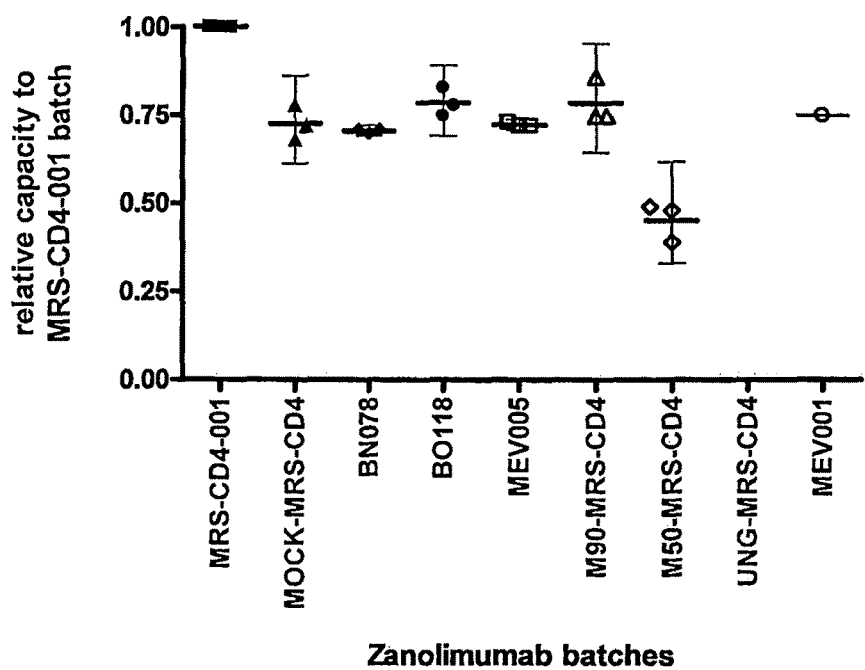
FIG. 14: Ability of zanolimumab to bind plate-bound FcγRI. The relative potency relative to reference batch MRS-CD4-001 and geometric means with 95% confidence intervals are shown. MEV001, MEV005, BN078 and BO118 are zanolimumab batches with differences in heavy chain glycosylation. UNG-MRS-CD4 is de-glycosylated Zanolimumab batch, MOCK-MRS-CD4 is a sham-de-glycosylated batch, and M90-MRS-CD4 and M50-MRS-CD4 are mixed batches (mix of de-glycosylated and fully glycosylated reference batch) with 90% of heavy chains glycosylated and 50% of heavy chains glycosylated, respectively.

Compared to reference batch MRS-CD4-001, most batches bound slightly lower to cell-bound FcγRI, despite differences in glycosylation of the batches. It should be noted that the variation in this assay was relatively high. Still, batch M50-MRS-CD4, containing only 50% glycosylated heavy chains has a significant lower binding capacity. The batch UNG-MRS-CD4 doesn't show much binding to plate-bound FcγRI (FIG. 14).

Example 17

Correlation of the Ability to Induce ADCC of Zanolimumab Batches with Relative Potencies Measured in Binding to CD4, to FcγRI, to FcγRIIIa176V, or the Combination of CD4 and FcγRIIIa176V Binding Several batches of zanolimumab (see example 8) were tested for binding to plate-bound FcγRI.

The reference and zanolimumab mix batches (different in glycosylation of heavy chains) were ranked according to the level of glycosylated heavy chains present and the potential correlation with the several assays.

Compared to reference batch MRS-CD4-001 the batches UNG-MRS-CD4, M50-MRS-CD4, and M90-MRS-CD4 all do bind comparable to CD4 (FIG. 15B; also FIG. 9), however differ in binding to FcγRI (FIG. 15C; also FIGS. 13 and 14) and FcγRIIIa176V (FIG. 15D; also FIG. 5), which is correlated to the level of heavy chain glycosylation. Also in the AlphaScreen™ assay (FIG. 15E; FIG. 12) and the functional ADCC (FIG. 15A; also FIG. 3) this correlation does exist.

These data indicate that binding to the FcγR does correlate with antibody Fc-mediated activities which play a critical role in the mechanism of action.

Example 18

Figure 16:
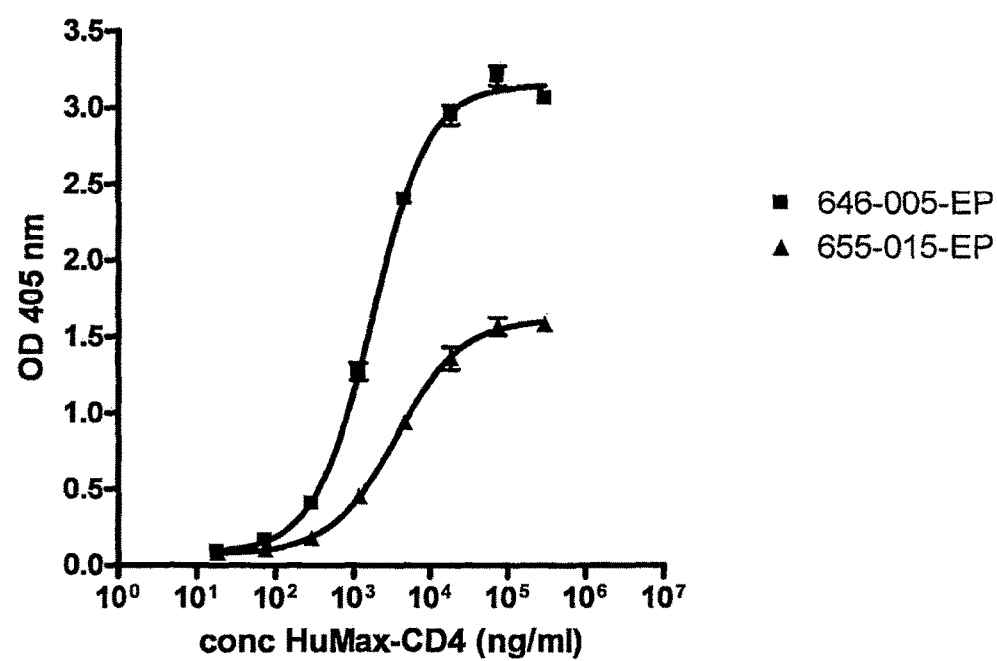
FIG. 16: Comparison of two CHO-K1SV derived FcγRIIIaECD176VHis batches in a plate bound FcγRIIIaECD176VHis binding ELISA. Two different FcγRIIIaECD176VHis batches (646-005-EP and 655-015-EP) were coated to the plate and binding of HuMax-CD4 to these batches was compared.

Desialylation of FcγRIIIa176V Improves the Performance of the FcγRIIIa176V Binding ELISA Two batches of FcγRIIIa176V derived from CHO-K1SV cells were tested for their suitability in a plate bound FcγRIIIa176V binding ELISA (as described above). A Greiner plate was coated with 100 μl of 2.5 μg/ml FcγRIIIa176V batch 646-005-EP or 655-015-EP and incubated overnight at 4° C. Plates were washed 3 times with 200 μl PBST (PBS containing 0.05% Tween-20) and 100 μl of serial diluted zanolimumab samples (concentrations of zanolimumab of 300, 75, 18.75, 4.69, 0.29, 1.17, 0.07, and 0.02 μg/ml). The plates were incubated 60 min at RT, under shaking conditions and were then washed 3 times with 200 μl PBST followed by addition of conjugate 1:4000 diluted peroxidase-conjugated affinipure F(ab')₂ Fragment G-anti-Hu-IgG, F(ab')₂ fragment specific ((Jackson ImmunoResearch, Brunschwig Chemie B.V., Amsterdam, The Netherlands). The plates were again incubated 60 min at RT under shaking conditions and then washed 3 times with 200 μl PBST. 100 μl ABTS (Roche, cat nr 1112597) was added and the plates were incubated 30 min under shaking conditions. The reaction was stopped with addition of 100 μl 2% oxalic acid and the absorbance at 405 nm was measured. The results are shown in FIG. 16.

Figure 17:
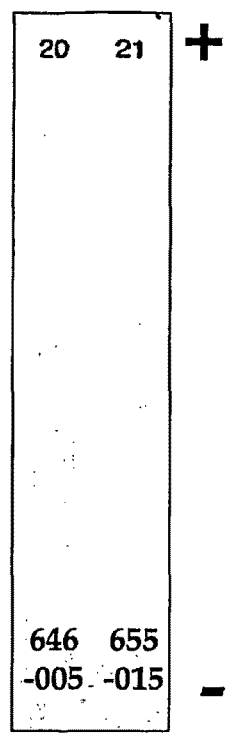
FIG. 17: Native electrophoresis of FcγRIIIaECD176VHis batch 646-005-EP and 655-015-EP as described in Example 18.
Figure 18:
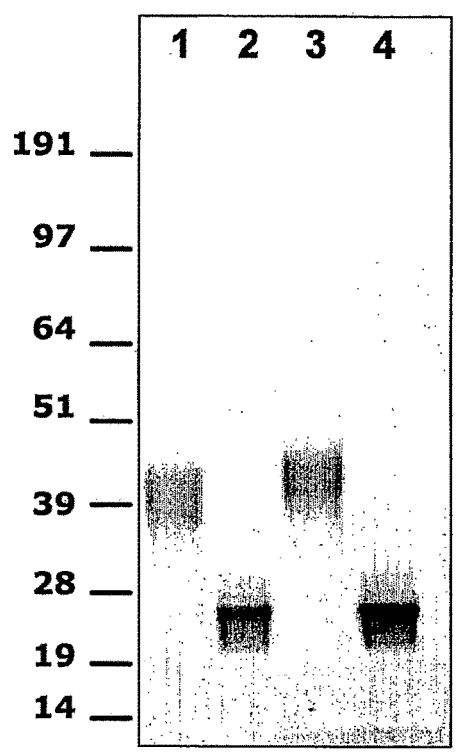
FIG. 18: Reduced 4-10% Nupage Bis-Tris analysis of untreated and deglycosylated FcγRIIIa176V. Lane 1: untreated FcγRIIIaECD176VHis batch 646-005-EP; Lane 2: deglycosylated FcγRIIIaECD176VHis batch 646-005-EP; Lane 3: untreated FcγRIIIaECD176VHis batch 655-015-EP; Lane 4: deglycosylated FcγRIIIaECD176VHis batch 655-015-EP. The migration of the markers (kDa) is indicated on the left.

Batch 646-005-EP gave a nice dose-response curve with high top values, whereas the batch 655-015-EP showed a much more shallower curve with lower top values. Previously, it was noted that these batches also differed in their negative charge as was visualized by native gel-electrophoresis, i.e. batch 655-015-EP appeared to contain more negative charge than batch 646-005-EP (FIG. 17). In addition, the two batches migrated differently on reduced SDS-PAGE, whereas they migrated at the same position after enzymatic deglycosylation (FIG. 18). This indicate that the difference in molecular weight was caused by differences in N-linked glycosylation. Sialic acid was removed from batch 655-015-EP and the desialylated receptor was compared to the untreated receptor in the FcγRIIIa176V binding ELISA.

To remove the sialic acids, batch 655-015-EP (in phosphate buffered saline) was incubated with *Arthrobacter ureafaciens* sialidase (Roche, catalogue number 10269611001; about 1 mg FcγRIIIa176V with 80 mU sialidase) for 72 hours at 37° C. After incubation, the desialylated receptor was purified using TALON™ beads and buffer-exchanged to phosphate buffered saline using PD-10 columns as described in Example 5, yielding 1.2 ml purified desialylated FcγRIIIa176V with a concentration of 0.45 mg/ml (batch 403-041-EP).

Figure 19:
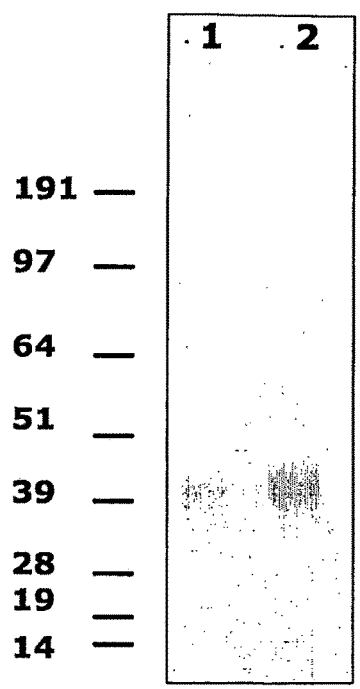
FIG. 19: Reduced 4-10% Nupage Bis-Tris analysis of untreated and desialylated FcγRIIIaECD176VHis. Lane 1: untreated FcγRIIIaECD176VHis batch 655-015-EP; Lane 2: desialylated FcγRIIIaECD176VHis batch 403-041-EP. The migration of the markers (kDa) is indicated on the left.
Figure 20:
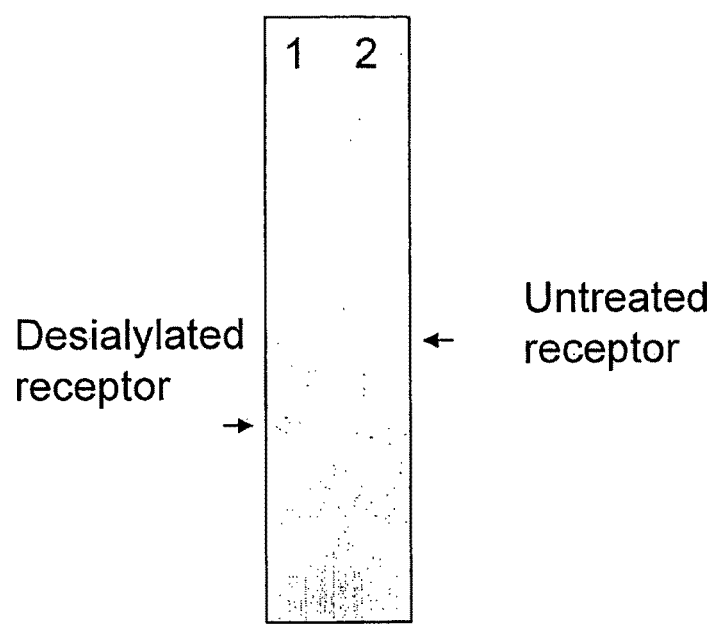
FIG. 20: Native electrophoresis of untreated and desialylated FcγRIIIaECD176FHis. Lane 1: desialylated FcγRIIIaECD176VHis batch 655-015-EP; Lane 2: untreated FcγRIIIaECD176VHis batch 403-041-EP. The migration of the markers (kDa) is indicated on the left.

Next, untreated batch 655-015-EP and desialylated batch 403-041-EP were analyzed by SDS-PAGE (FIG. 19) and native gel-electrophoresis (FIG. 20). The negative charge of the desialylated batch was much less compared to the untreated FcγRIIIa176V, and also the molecular weight seemed to be slightly smaller compared to untreated FcγRIIIa176V. This suggested that desialylation of the receptor had been successful.

Figure 21:
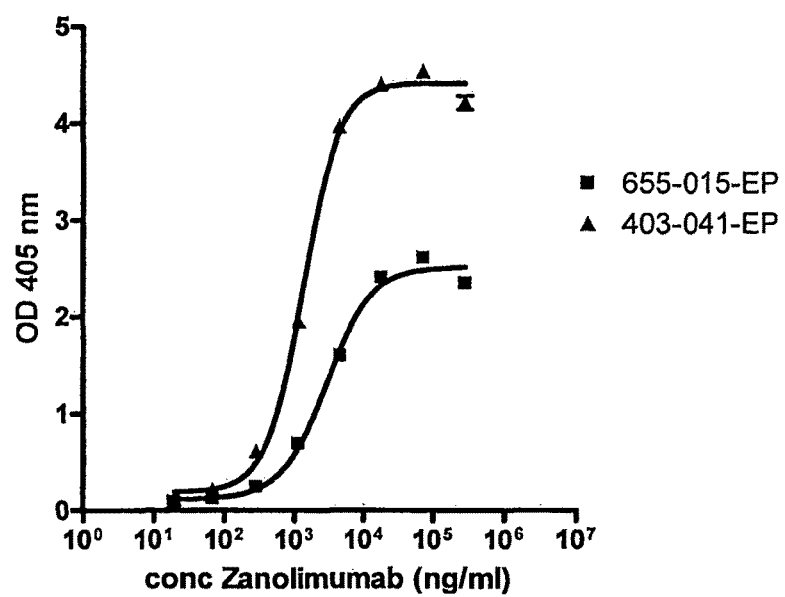
FIG. 21: Comparison of desialylated and untreated FcγRIIIaECD176VHis in a plate bound FcγRIIIaECD176VHis binding ELISA. Desialylated FcγRIIIaECD176VHis (batch 403-041-EP) and untreated FcγRIIIaECD176VHis (655-015-EP) were coated to the plate at the same concentration and binding of zanolimumab to these batches was compared.

Desialylated and untreated FcγRIIIa176V were compared in the plate bound FcγRIIIa176V binding ELISA. Both preparations were coated to the plate at a concentration of 2.5 μg/ml and binding with zanolimumab was performed as described above. FIG. 21 clearly shows that desialylation of the receptor improved the performance of the plate bound binding assay significantly.

Figure 22:
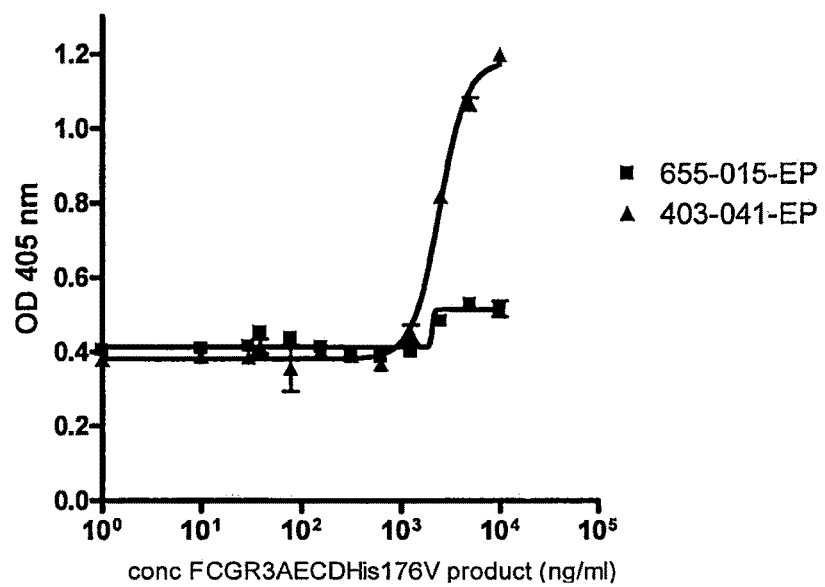
FIG. 22: Comparison of coating efficiency of desialylated and untreated FcγRIIIa176V. Serial dilutions of desialylated and untreated FcγRIIIa176V were coated to the plate and bound receptor was detected with a mouse-anti-CD16.

To determine whether this is explained by improved binding of desialylated FcγRIIIa176V to the plate, two-fold serial dilutions of desialylated FcγRIIIa176V (batch 403-041-EP) and untreated FcγRIIIa176V (655-015-EP) were coated to the plate. Starting concentration was 10 µg/ml. Plates were washed with PBTS and bound FcγRIIIa176V was detected with mouse-anti-CD16-FITC (BD Biosciences, catalogue number 555406), followed by Sheep-anti-FITC-HRP (Roche, catalogue number 11426356910). Plates were developed with ABTS. FIG. 22 shows that indeed desialylated FcγRIIIa176V showed improved binding to the plate, when compared to untreated FcγRIIIa176V.

Example 19

Capture of His-Tagged FcγRIIIa176V Via His-Capturing Antibody Coated on the ELISA Plate Increases the Sensitivity of the ELISA Capturing of his-tagged FcγRIIIaECD176VHis via a his-capturing antibody was compared to direct coating of his-tagged FcγRIIIaECD176VHis to the ELISA plate.

Greiner plates were coated with 100 µl of 1 µg/ml FcγRIIIa176V batch #0646-005-EP or with anti-polyhistidine mAb (mouse-anti-polyhistidine, IgG1 mAb clone AD1.1.10, R&D, product# MAB050, 0.5 mg/ml in PBS/5% trehalose, lot# AEJ 175031) and incubated overnight at 4° C. Plates were washed 3 times with 200 µl PBST (PBS containing 0.05% Tween-20), and blocked for 60 min with 1% BSA in PBS. The anti-polyhistidine mAb coated plates were further incubated with 100 µl of 1 µg/ml FcγRIIIa158V batch for 60 min at RT, under shaking conditions, and subsequently washed 3 times with 200 µl PBST. Both types of coated plates were incubated with 100 µl of serially diluted HuMax-EGFr samples (concentrations of HuMax-EGFr of 300, 75, 18.75, 4.69, 0.29, 1.17, 0.07, and 0.02 µg/ml; batch1 #095-03-01F and batch 2 # P247740) for 60 min at RT, under shaking conditions, and subsequently 3 times with 200 µl PBST followed by addition of conjugate, 1:10,000 diluted peroxidase-conjugated affinipure F(ab')₂ Fragment G-anti-Hu-IgG, F(ab')₂ fragment specific (Jackson ImmunoResearch, Brunschwig Chemie B.V., Amsterdam, The Netherlands). The plates were incubated 60 min at RT under shaking conditions, and washed 3 times with 200 µl PBST. 100 µl ABTS was added and the plates were incubated approximately 20 min under shaking conditions. The reaction was stopped with addition of 100 µl 2% oxalic acid, and the absorbance at 405 nm was measured.

Figure 23:
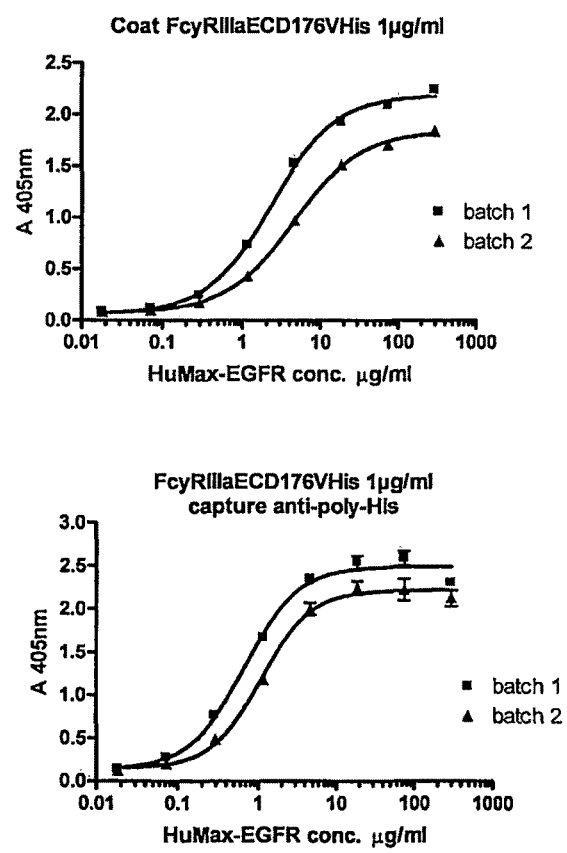
FIG. 23, binding curves of two batches of antibody HuMax-EGFr to FcγRIIIaECD176VHis, coated either directly (A) (upper panel) or via his-capturing (anti-polyhistidine) antibody (B) (lower panel), are given (data are mean±SD, n=3).

In FIG. 23, binding curves of the two batches of antibody HuMax-EGFr to FcγRIIIa 176V, coated either directly (upper panel) or via his-capturing mAb (lower panel), are given (data are mean±SD, n=3). Coating via his-capture results in a higher affinity for the HuMax-EGFr-FcγRIIIa 176V interaction, about a 4 times higher affinity compared to directly coated FcγRIIIa176V. Higher affinity is also favorable because of slower dissociation. Thus, capture of his-tagged FcγRIIIa176V via his-capturing antibody increases the sensitivity of the binding ELISA. Notably, the EC50 ratios of the two tested HuMax-EGFr batches were the same for both ELISA formats (on average about 2), which indicates that the assay formats are comparable for determining relative potency.

Example 20

Fc-Dependent Down-Modulation of CD4 Receptor of CD4+ Tcells by Zanolimumab

The capacity of zanolimumab to down-regulate CD4 in the presence of effector cells was studied with PBMC-derived CD4+ T-cells (isolation see example 7), or SUP-T1 cells and with or without the addition of PBMC-derived monocytes (isolation according to protocol of Dynal® monocyte Negative Isolation Kit) or TPH-1 cells. PBMC or SUP-T1 cells were incubated with a concentration range of zanolimumab, zanolimumab-F(ab')2 fragments (SUP-T1), zanolimumab-Fab (SUP-T1) or the negative control HuMab-KLH. When appropriate, effector cells were added to an effector cell:target cell ratio of 10:1, 5:1 or 4:1. IFN-γ (concentration ranging from 125 to 1000 µg/ml) was added and cells were incubated overnight. Thereafter, cells were stained for CD4 with fluorochrome-labeled M-T477 (non-competitive Ab from BD) and for a target cell selection marker (to distinguish target cells from other cells). Cell-associated fluorescence was assessed by flow cytometry.

Figure 24A:
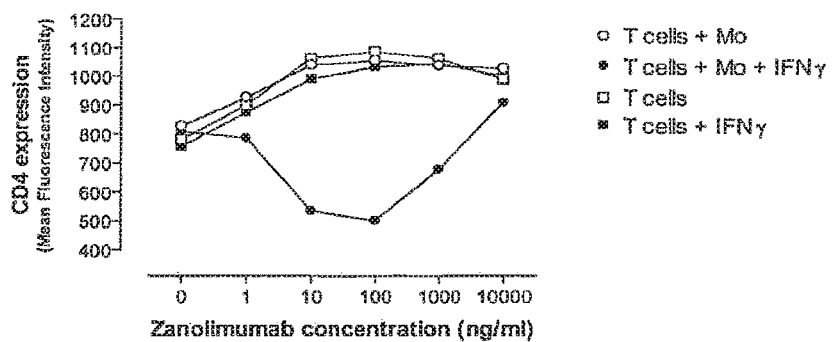
FIGS. 24A and 24B, Zanolimumab down-modulates CD4 expression on CD4+ T cells.
Figure 24B:
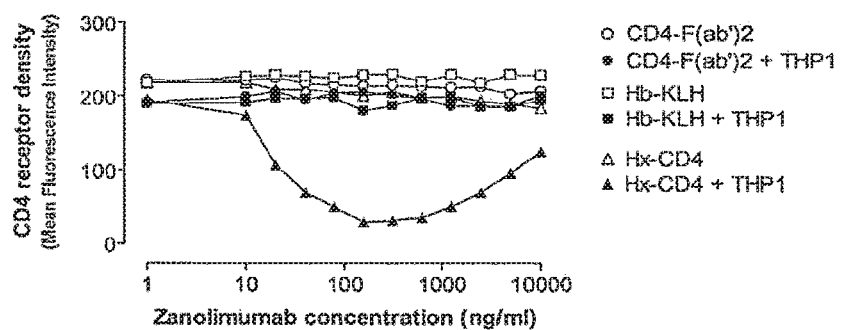

In FIG. 24, The capacity of zanolimumab to induce CD4 down-regulation is shown by flow cytometry with a non-competing CD4 monoclonal antibody using freshly isolated CD4+ T cells or SUP-T1 T cells. Zanotimumab dose-dependently down-regulated CD4 from purified primary CD4+ T-cells (FIG. 4A) or SUP-T1 T cells (FIG. 4B), requiring the presence of monocytes, or a monocytic cell line, respectively. The results showed that after 18-24 h the level of CD4 expression was reduced by 50-80%. Down-modulation appeared to be Fc-dependent as incubation with F(ab')2 fragments did not result in a reduction in CD4 expression either in the presence or absence of accessory cells (FIG. 4B). At high mAb concentrations, soluble zanolimumab failed to down-regulate CD4, possible due to monomeric binding, resulting in a reduction of cross-linking. Cross-Linking via immobilized zanolimumab or plate-bound IgG-cross-linking Ab in combination with soluble zanolimumab pre-incubation also down-regulated CD4 (data not shown).

All references, including publications, patent applications, and patents, cited herein are hereby incorporated by reference to the same extent as if each reference were individually and specifically indicated to be incorporated by reference and were set forth in its entirety herein.

All headings and sub-headings are used herein for convenience only and should not be construed as limiting the present invention in any way.

Any combination of the above-described elements in all possible variations thereof is encompassed by the present invention unless otherwise indicated herein or otherwise clearly contradicted by context.

The use of the terms "a" and "an" and "the" and similar referents in the context of describing the present invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the present invention and does not pose a limitation on the scope of the present invention unless otherwise indicated. No language in the specification should be construed as indicating any element is essential to the practice of the present invention unless as much is explicitly stated.

The citation and incorporation of patent documents herein is done for convenience only and does not reflect any view of the validity, patentability, and/or enforceability of such patent documents.

The description herein of any embodiment of the present invention using terms such as "comprising", "having," "including," or "containing" with reference to an element or elements is intended to provide support for a similar embodiment of the present invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The present invention includes all modifications and equivalents of the subject matter recited in the embodiments presented herein to the maximum extent permitted by applicable law.

All patents, pending patent applications and other publications cited herein are hereby incorporated by reference in their entirety.

The invention claimed is:

1. A method for analyzing and selecting at least one batch of a drug product, wherein the batch comprises an antibody or antibody fragment having an Fc receptor (FcR)-binding moiety, and wherein at least one mechanism of action of the antibody or antibody fragment of the drug product is mediated through the binding of the antibody or antibody fragment of the drug product to an Fc receptor, the method comprising the steps of:
   (a) providing an antibody or antibody fragment of the drug product and a reference standard antibody or antibody fragment,
   (b) contacting the antibody or antibody fragment of the drug product with an FcγRIII receptor, wherein the FcγRIII receptor has been modified such that it has a reduced amount of sialic acid on the N-linked glycosylation as compared to the same FcγRIII receptor in unmodified form,
   (c) contacting the reference standard to the FcγRIII receptor,
   (d) measuring the binding of the antibody or antibody fragment to the FcγRIII receptor,
   (e) measuring the binding of the reference standard to the FcγRIII receptor,
   (f) comparing the FcR binding of the antibody or antibody fragment to the FcR binding of the reference standard, and
   (g) selecting the antibody or antibody fragment that has equal to or greater binding to the FcγRIII receptor compared to the reference standard, wherein the reference standard and the antibody or antibody fragment of the drug product are two different batches of the same antibody or antibody fragment.

2. A method according to claim 1, wherein the binding of the antibody or antibody fragment to the FcγRIII receptor is determined by (i) bringing a sample of the drug product into contact with the FcγRIII for a time period sufficient for allowing the antibody or antibody fragment to bind to the FcγRIII receptor, and (ii) detecting the amount of antibody or antibody fragment bound to the FcγRIII receptor.

3. A method according to claim 2, wherein the detecting step comprises adding a detecting antibody directed at the antibody or antibody fragment.

4. A method according to claim 3, wherein the detecting antibody is a labeled antibody.

5. A method according to claim 1, wherein the binding of the antibody or antibody fragment to the FcγRIII receptor is determined by use of an enzyme-linked immunosorbent assay (ELISA).

6. A method according to claim 1, wherein the binding of the FcR binding peptide to the FcγRIII receptor is determined by an AlphaScreen™ assay.

7. A method according to claim 1, wherein the binding of the FcR binding peptide to the FcγRIII receptor is determined by a radioimmunoassay.

8. A method according to claim 1, wherein the binding of the FcR binding peptide to the FcγRIII receptor is determined by a Biacore assay.

9. A method according to claim 1, wherein the binding of the FcR binding peptide to the FcγRIII receptor is determined by a fluorometric microvolume assay technology (FMAT).

10. A method according to claim 1, wherein the binding of the FcR binding peptide to the FcγRIII receptor is determined by a dissociation-enhanced lanthanide fluorescent immunoassay (DELFIA).

11. A method according to claim 1, wherein at least one mechanism of action of the antibody or antibody fragment is mediated through antibody dependent cell-mediated cytotoxicity (ADCC).

12. A method according to claim 1, wherein at least one mechanism of action of the antibody or antibody fragment is mediated through down modulation of target receptors.

13. A method according to claim 1, wherein at least one mechanism of action of the antibody or antibody fragment is mediated through the recruitment of natural killer cells.

14. A method according to claim 1, wherein at least one mechanism of action of the antibody or antibody fragment is mediated through ADCC by natural killer cells.

15. A method according to claim 1, wherein the Fc receptor to which the antibody or antibody fragment binds is expressed on natural killer cells.

16. A method according to claim 12, wherein the Fc receptor is an FcγRIIIa receptor which retains the ability to bind an Fc region.

17. A method according to claim 16, wherein the FcγRIII receptor is an FcγRIIIa176V receptor which retains the ability to bind an Fc region.

18. A method according to claim 1, wherein at least one mechanism of action of the antibody or antibody fragment is mediated through the recruitment of polymorphonuclear leukocytes.

19. A method according to claim 1, wherein at least one mechanism of action of the antibody or antibody fragment is mediated through the induction of ADCC by polymorphonuclear leukocytes.

20. A method according to claim 1, wherein at least one mechanism of action of the antibody or antibody fragment is mediated through the induction of PMN degranulation.

21. A method according to claim 1, wherein at least one mechanism of action of the antibody or antibody fragment is mediated through the induction of phagocytosis by polymorphonuclear leukocytes.

22. A method according claim 1, wherein the Fc receptor to which the antibody or antibody fragment binds is expressed on polymorphonuclear leukocytes.

23. A method according to claim 1, wherein at least one mechanism of action of the antibody or antibody fragment is mediated through the induction of ADCC by monocytes or macrophages.

24. A method according claim 1, wherein the Fc receptors to which the antibody or antibody fragment binds is expressed on monocytes and/or macrophages.

25. A method according to claim 1, wherein at least one mechanism of action of the antibody or antibody fragment is further mediated through the recruitment of platelets.

26. A method according to claim 1 or claim 25, wherein the antibody or the antibody fragment also binds FcγRII receptor expressed on platelets.

27. A method according to claim 1, wherein at least one mechanism of action of the antibody or antibody fragment is to induce cytokine production.

28. A method according to claim 27, wherein the Fc receptor to which the antibody or antibody fragment binds is expressed on natural killer cells.

29. A method according to claim 1, wherein at least one mechanism of action of the antibody or antibody fragment is to induce clearance of immune complexes.

30. A method according to claim 1, wherein at least one mechanism of action of the antibody or antibody fragment is mediated through the recruitment of monocytes and/or macrophages.

31. A method according to claim 1, wherein the Fc receptor is an FcγRIII which retains the ability to bind an Fc region.

32. A method according to claim 1, wherein the Fc receptor is an FcγRIIIb which retains the ability to bind an Fc region.

33. A method according to claim 1, wherein at least one mechanism of action of the antibody or antibody fragment is to induce down-regulation of antibody responses.

34. A method according to claim 1, wherein at least one mechanism of action of the antibody or antibody fragment is mediated through the recruitment of B cells.

35. A method according to claim 1, wherein the antibody or the antibody fragment also binds FcγRII receptor expressed on B cells.

36. A method according to claim 1, wherein at least one mechanism of action of the antibody or antibody fragment is to induce monocyte and macrophage effector function inhibition.

37. A method according to claim 1, wherein at least one mechanism of action of the antibody or antibody fragment is to induce phagocytosis.

38. A method according to claim 1, wherein at least one mechanism of action of the antibody or antibody fragment is mediated through the recruitment of polymorphonuclear leukocytes, macrophages and/or dendritic cells.

39. A method according to claim 1, wherein the Fc receptor to which the antibody or antibody fragment binds is expressed on polymorphonuclear leukocytes, macrophages and/or dendritic cells.

40. A method according to claim 1, wherein at least one mechanism of action of the antibody or antibody fragment is mediated through the induction of phagocytosis by monocytes or macrophages.

41. A method according to claim 1, wherein at least one mechanism of action of the antibody or antibody fragment is mediated through cross-linking of cells and/or antibodies.

42. A method according to claim 1, wherein at least one mechanism of action of the antibody or antibody fragment is to induce positive signaling via an immunoreceptor tyrosine-based activation motif.

43. A method according to claim 1, wherein at least one mechanism of action of the antibody or antibody fragment is further mediated through the recruitment of myeloid cells and/or platelets.

44. A method according to claim 1, wherein the antibody or antibody fragment binds FcγRII receptor expressed on myeloid cells and/or platelets.

45. A method according to claim 1, wherein a mechanism of action of the antibody or antibody fragment is to induce positive signaling via common γ, β, ζ chains.

46. A method according to claim 1, wherein at least one mechanism of action of the antibody or antibody fragment is mediated through the recruitment of myeloid cells, polymorphonuclear leukocytes or natural killer cells.

47. A method according to claim 1, wherein the Fc receptor to which the antibody or antibody fragment binds is expressed on myeloid cells, polymorphonuclear leukocytes or natural killer cells.

48. A method according to claim 1, wherein at least one mechanism of action of the antibody or antibody fragment is to induce negative signaling through an immunoreceptor tyrosine-based inhibition motif.

49. A method according to claim 1, wherein at least one mechanism of action of the antibody or antibody fragment is mediated through the recruitment of B cells, macrophages and/or monocytes.

50. A method according to claim 1, wherein the antibody or antibody fragment further binds an Fc receptor is expressed on B cells, macrophages and/or monocytes.

51. A method according to claim 1, wherein the FcγRIII receptor has been expressed in a host cell defective in the mechanisms responsible for sialylation.

52. A method according to claim 1, wherein the FcγRIII receptor has been treated with sialidase.

53. A method according to claim 1, wherein the antibody or antibody fragment is a monoclonal antibody.

54. A method according to claim 1, wherein the antibody or antibody fragment is a human antibody.

55. A method according to claim 1, wherein the antibody or antibody fragment is a humanized antibody.

56. A method according to claim 1, wherein the antibody or antibody fragment is a chimeric antibody.

57. A method according to claim 1, wherein the antibody or antibody fragment is an IgG1 antibody.

58. A method according to claim 57, wherein the antibody or antibody fragment is an IgG1,A antibody.

59. A method according to claim 57, wherein the antibody or antibody fragment is an IgG1,K antibody.

60. A method according to claim 1, wherein the measuring of the binding of the antibody to an FcγRIII receptor is combined with a method of determining the binding of the antibody to its antigen.

61. A method according to claim 60, wherein the binding of the antibody to its antigen is determined by (i) bringing a sample of the antibody into contact with the antigen for a time period sufficient for allowing the antibody to bind to the antigen, and (ii) detecting the amount of antibody bound to the antigen.

62. A method according to claim 61, wherein the detection involves adding a detecting antibody directed at the antibody of the drug product.

63. A method according to claim 62, wherein the detecting antibody is a labeled antibody.

64. A method according to 60, wherein the binding of the antibody to its antigen is determined by ELISA.

65. A method according to claim 64, wherein binding of the antibody to the Fc receptor is determined with the same ELISA.

66. A method according to claim 60, wherein the binding of the antibody to its antigen is determined by an AlphaScreen™ assay.

67. A method according to claim 66, wherein the binding of the antibody to the Fc receptor is also determined by the AlphaScreen™ assay.

68. A method according to claim 60, wherein the binding of the antibody to its antigen is determined by a radioimmunoassay.

69. A method according to claim 68, wherein the binding of the antibody to the FcγRIII receptor is also determined by a radioimmunoassay.

70. A method according to claim 69, wherein the radioimmunoassay comprises beads conjugated with FcγRIII receptor and radioiodonated antigen.

71. A method according to claim 1, wherein the antibody or antibody fragment is an antibody binding to human CD4.

72. A method according to claim 1, wherein the antibody is zanolimumab.

73. A method according to claim 71, wherein the antibody is keliximab.

74. A method according to claim 71, wherein the antibody is clenoliximab.

75. A method according to claim 1, wherein the antibody is an antibody that binds to human EGFR.

76. A method according to claim 75, wherein the antibody is cetuximab.

77. A method according to claim 75, wherein the antibody is zalutumumab.

78. A method according to claim 1, wherein the antibody is an antibody binding to human CD20.

79. A method according to claim 78, wherein the antibody is rituximab.

80. A method according to claim 78, wherein the antibody is ibritumomab tiuxetan.

81. A method according to claim 78, wherein the antibody is tositumomab.

82. A method according to claim 78, wherein the antibody is ofatumumab.

83. A method according to claim 1, wherein the antibody is an antibody binding to human CD25.

84. A method according to claim 1, wherein the antibody is an antibody binding to human CD3.

85. A method according to claim 84, wherein the antibody is muromonab.

86. A method according to claim 1, wherein the antibody is an antibody that binds to human GPIIb/IIIa.

87. A method according to claim 83, wherein the antibody is daclizumab.

88. A method according to claim 83, wherein the antibody is basiliximab.

89. A method according to claim 1, wherein the antibody is an antibody that binds to human TNF-α.

90. A method according to claim 89, wherein the antibody is infliximab.

91. A method according to claim 89, wherein the antibody is adalimumab.

92. A method according to claim 1, wherein the antibody is an antibody that binds to human RSV.

93. A method according to claim 92, wherein the antibody is palivizumab.

94. A method according to claim 1, wherein the antibody is an antibody binding to human HER-2/neu.

95. A method according to claim 94, wherein the antibody is trastuzumab.

96. A method according to claim 94, wherein the antibody is pertuzumab.

97. A method according to claim 1, wherein the antibody is an antibody that binds to human CD33.

98. A method according to claim 1, wherein the antibody is an antibody that binds to human CD52.

99. A method according to claim 98, wherein the antibody is alemtuzumab.

100. A method according to claim 1, wherein the antibody is an antibody that binds to human VEGF.

101. A method according to claim 100, wherein the antibody is bevacizumab.

102. A method according to claim 1, wherein the antibody is an antibody binding to human CTLA4.

103. A method according to claim 102, wherein the antibody is ipilimumab.

104. A method according to claim 5, wherein the FcγRIII receptor is his-tagged, and a his-capturing antibody coated on the ELISA plate captures the his-tagged FcγRIII receptor.

* * * * *

UNITED STATES PATENT AND TRADEMARK OFFICE
CERTIFICATE OF CORRECTION

PATENT NO. : 9,580,506 B2
APPLICATION NO. : 11/989064
DATED : February 28, 2017
INVENTOR(S) : Catharina Emanuele Gerarda Havenith et al.

It is certified that error appears in the above-identified patent and that said Letters Patent is hereby corrected as shown below:

In the Claims

Column 67, Claim 22, Line 65, delete "A method according claim 1," and insert -- A method according to claim 1, --.

Column 68, Claim 24, Line 5, delete "A method according claim 1," and insert -- A method according to claim 1, --.

Column 69, Claim 64, Line 66, delete "A method according to 60," and insert -- A method according to claim 60, --.

Signed and Sealed this
Twentieth Day of February, 2018

Andrei Iancu
*Director of the United States Patent and Trademark Office*